United States Patent
McGowan et al.

(10) Patent No.: US 11,230,547 B2
(45) Date of Patent: Jan. 25, 2022

(54) PURINE INHIBITORS OF HUMAN PHOSPHATIDYLINOSITOL 3-KINASE DELTA

(71) Applicant: Merck Sharp & Dohme Corp., Rahway, NJ (US)

(72) Inventors: Meredeth A. McGowan, Boston, MA (US); Jason D. Katz, Newton Highlands, MA (US); Matthew Christopher, Brookline, MA (US); Hua Zhou, Acton, MA (US); David James Witter, Norfolk, MA (US); Chaomin Li, Boston, MA (US); John Lampe, Norfolk, MA (US); Joey L. Methot, Westwood, MA (US); Abdelghani A. Achab, Melrose, MA (US); Xavier Fradera, Boston, MA (US); Shimin Xu, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/764,448

(22) PCT Filed: Dec. 12, 2018

(86) PCT No.: PCT/US2018/065059
§ 371 (c)(1),
(2) Date: May 15, 2020

(87) PCT Pub. No.: WO2019/125838
PCT Pub. Date: Jun. 27, 2019

(65) Prior Publication Data
US 2020/0392144 A1 Dec. 17, 2020

(30) Foreign Application Priority Data
Dec. 18, 2017 (WO) ................ PCT/CN2017/116917

(51) Int. Cl.
*C07D 487/08* (2006.01)
*C07D 519/00* (2006.01)
*C07D 403/14* (2006.01)

(52) U.S. Cl.
CPC ......... *C07D 487/08* (2013.01); *C07D 403/14* (2013.01); *C07D 519/00* (2013.01)

(58) Field of Classification Search
CPC ... C07D 487/08; C07D 403/14; C07D 519/00
See application file for complete search history.

(56) References Cited

U.S. PATENT DOCUMENTS

| | | | |
|---|---|---|---|
| 2009/0036475 A1 | 2/2009 | Eriksen et al. | |
| 2011/0123434 A1 | 5/2011 | Lamb et al. | |
| 2011/0152519 A1 | 6/2011 | Nagata et al. | |
| 2014/0323435 A1 | 10/2014 | Dorsey et al. | |
| 2017/0190689 A1 | 7/2017 | Sparks et al. | |

FOREIGN PATENT DOCUMENTS

| | | | |
|---|---|---|---|
| CN | 102046609 | * | 5/2011 |
| CN | 102046609 A | | 5/2011 |
| CN | 105541803 A | | 5/2016 |
| WO | 2005007646 A1 | | 1/2005 |
| WO | WO2006/065872 | * | 6/2006 |
| WO | 2008070661 A1 | | 6/2008 |

OTHER PUBLICATIONS

Norcross et al. Journal of Medicial Chemistry 59, 6101-6120 (2016) (Year: 2016).*
International Search Report and Written Opinion for PCT/CN2017/116917, dated Sep. 7, 2018, 16 pages.
Norcross, R. et al., Trisubstituted Pyrimidines as Efficacious and Fast-Acting Antimalarials, Journal of Medicinal Chemistry, 2016, 6101-6120, 59.
Database Registry [Online] Chemical Abstracts Service, Columbus, Ohio, US; Sep. 17, 2009 (Sep. 17, 2009), Database accession No. 1185505-44-5, 1 page.
Database Registry [Online] Chemical Abstracts Service, Columbus, Ohio, US; Sep. 18, 2009 (Sep. 18, 2009), Database accession No. 1185700-41-7, 1 page.

(Continued)

*Primary Examiner* — Dennis Heyer
(74) *Attorney, Agent, or Firm* — Patricia A. Shatynski; John C. Todaro

(57) ABSTRACT

The instant invention provides compounds of formulas Ia and Ib which are PI3K-delta inhibitors, and as such are useful for the treatment of PI3K-delta-mediated diseases such as inflammation, asthma, COPD and cancer.

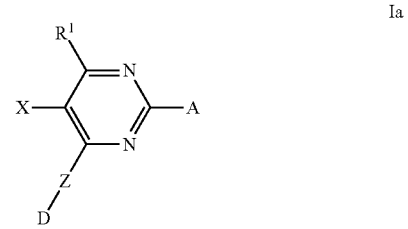

Ia

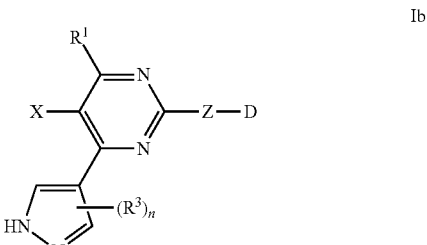

Ib

3 Claims, No Drawings

(56) References Cited

OTHER PUBLICATIONS

Database Registry [Online] Chemical Abstracts Service, Columbus, Ohio, US; May 23, 2013 (May 23, 2013), Database accession No. 1432419-49-2, 1 page.
Zhang, Wei, Fluorous Synthesis of Disubstituted Pyrimidines, Organic Letters, American Chemical Society, 2003, 1011-1013, 5(7).

* cited by examiner

PURINE INHIBITORS OF HUMAN PHOSPHATIDYLINOSITOL 3-KINASE DELTA

CROSS-REFERENCE TO RELATED APPLICATIONS

This application is a U.S. National Phase application under 35 U.S.C. § 371 of PCT Application No. PCT/US2018/065059, filed on Dec. 12, 2018, which claims foreign priority of PCT Application No. PCT/CN2017/116917, filed on Dec. 18, 2017.

BACKGROUND OF THE INVENTION

Compounds are provided that inhibit phosphatidylinositol 3-kinase delta isoform (PI3K-delta) activity, including compounds that selectively inhibit PI3K-delta activity. The invention provides methods of using PI3K-delta inhibitory compounds to inhibit PI3K-delta mediated processes in vitro and in vivo.

SUMMARY OF THE INVENTION

The present invention provides novel compounds which are inhibitors of phosphoinosititde 3-kinases delta (PI3K-delta). The invention also provides a method for the treatment and prevention of PI3K-delta-mediated diseases and disorders using the novel compounds, as well as pharmaceutical compositions containing the compounds.

Methods of inhibiting PI3K-delta activity, and methods of treating diseases, such as disorders of immunity and inflammation, in which PI3K-delta plays a role in leukocyte function are disclosed. Methods of using PI3K-delta inhibitory compounds to inhibit cancer cell growth or proliferation are also provided.

DETAILED DESCRIPTION OF THE INVENTION

The present invention provides compounds of Formulas (Ia) and (Ib):

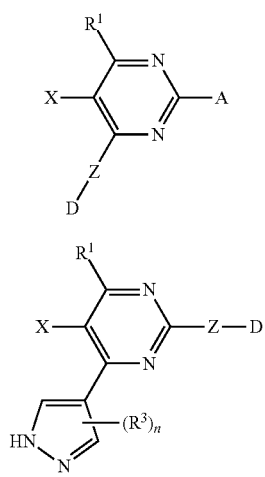

or a pharmaceutically acceptable salt thereof, wherein n is 0, 1, 3 or 3;
A is selected from: pyrazolyl, pyridinyl,

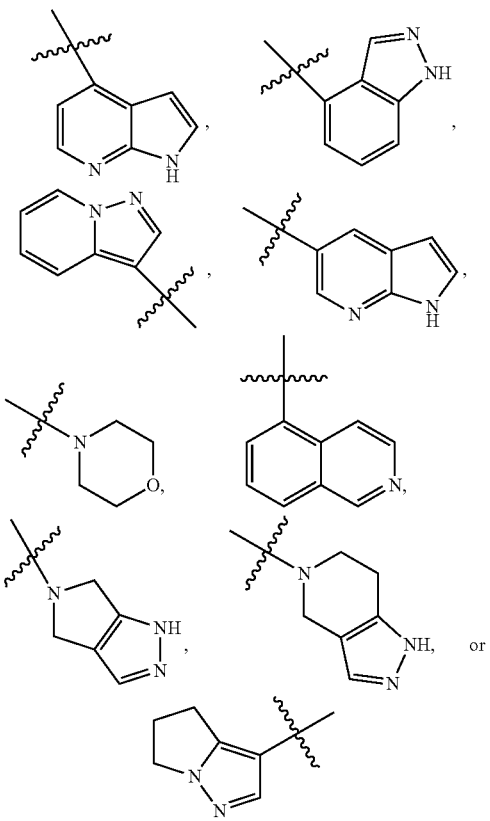

wherein A is substituted with 0, 1, 2, or 3 $R^2$ each independently selected from $C_1$-$C_6$ alkyl, amino, $C_1$-$C_6$ haloalkyl, and cyano;

each $R^1$ is independently selected from hydrogen, chloro, amino, cyano, $C_{1-6}$ alkyl, $C_{1-6}$ haloalkyl, $C_{3-12}$ heterocycloalkyl($C_{1-6}$ alkyl)$_{0-1}$, $C_{3-12}$ cycloalkyl($C_{1-6}$ alkyl)$_{0-1}$, $C_{1-6}$ alkyl(amino)$_{0-1}$ carbonylamino, $C_{1-6}$ haloalkyl (amino)$_{0-1}$ carbonylamino, $C_{3-12}$ cycloalkyl(amino)$_{0-1}$ carbonylamino, $C_{3-12}$ heterocycloalkyl(amino)$_{0-1}$ carbonylamino, $C_{1-6}$ alkylamino, $C_{1-6}$ haloalkylamino, $C_{3-12}$ cycloalkyl($C_{1-6}$ alkyl)$_{0-1}$ amino, $C_{3-12}$ heterocycloalkyl ($C_{1-6}$ alkyl)$_{0-1}$amino, $C_{5-7}$aryl ($C_{1-6}$ alkyl)$_{0-1}$amino, $C_{1-6}$ alkyloxy($C_{0-6}$ alkyl), $C_{1-6}$ haloalkyl oxy($C_{0-6}$ alkyl), $C_{3-12}$ cycloalkyloxy($C_{0-6}$ alkyl), and $C_{3-12}$ heterocycloalkyl oxy ($C_{0-6}$ alkyl) wherein $R^1$ is independently substituted by 0, 1, 2, or 3 $R^8$ independently selected from amino, hydroxy, $C_{1-6}$ alkyl, $C_{1-6}$ haloalkyl, and $C_{1-6}$ alkyloxy;

each $R^3$ is independently selected from hydrogen, $C_{1-6}$ alkyl, cyano, and amino;

each Z is independently selected from 2,5-diazabicyclo [2.2.1]hept-2-yl, piperazinyl, and 3,8-diazabicyclo[3.2.1] octyl, wherein each Z is substituted with 0, 1 or 2 $R^4$ each independently selected from $C_1$-$C_6$ alkyl, and —($C_1$-$C_6$ alkyl)OH;

each D is independently selected from phenyl, pyridinyl, cyclopropylcarbonyl, tert-butylcarbonyl, oxetanylcarbonyl, cyclobutylcarbonyl, thiophenylcarbonyl, cyclopentylsulfonyl, cyclopropylmethyl, propyl, ethylaminocarbonyl, oxazolylcarbonyl, oxetanylmethylcarbonyl, cyclopropylsulfonyl, isopropylsulfonyl, propylsulfonyl, ethylcarbonyl, cyclopentylcarbonyl, and spiro[2.4]heptyl-carbonyl, where each D is independently substituted with 0, 1, 2, or 3 $R^5$ each independently selected from cyano, $C_{1-6}$ haloalkyl, fluoro, $C_{1-6}$ alkyl, —($C_{1-6}$ alkyl)OH, $C_{1-6}$ alkoxy, $C_{1-6}$ alkoxy$C_{1-6}$ alkyl, pyrrolyl, nitro, $C_{3-12}$cycloalkyl, $C_{1-4}$ alkyl aminocarbonyl, and $C_{1-4}$ alkylsufonyl and wherein each $R^5$ is independently substituted with 0, 1, or 2, $R^6$ each independently selected from fluoro, hydroxy, methyl, and methoxy; and each X independently selected from cyano, chloro, hydrogen, propynol, 3-methylbutynyl, ethynyl, methylsulfanyl, difluoromethyl, ethylcarboxy, and oxazolyl; wherein said propynol, 3-methylbutynyl, ethynyl, methylsulfanyl, difluoromethyl, ethylcarboxy, or oxazolyl is substituted with 0, 1 or 2 $R^7$ each independently selected from $C_{1-4}$ alkyl, fluoro, hydroxy, and $C_{1-6}$ alkoxy.

Representative compounds of the instant invention include, but are not limited to, the following compounds and their pharmaceutically acceptable salts thereof.

4-[(1S,4R)-5-(3-cyanophenyl)-2,5-diazabicyclo[2.2.1]hept-2-yl]-2-(1-methyl-1H-pyrazol-4-yl)pyrimidine-5-carbonitrile;

4-[(1R,4S)-5-(3-fluorophenyl)-2,5-diazabicyclo[2.2.1]hept-2-yl]-2-pyrazolo[1,5-a]pyridin-3-ylpyrimidine-5-carbonitrile;

2-(4,6-dihydropyrrolo[3,4-c]pyrazol-5(1H)-yl)-4-[(1S,4R)-5-(3-fluorophenyl)-2,5-diazabicyclo[2.2.1]hept-2-yl]pyrimidine-5-carbonitrile;

4-{(1S,4R)-5-[6-(difluoromethyl)pyridin-3-yl]-2,5-diazabicyclo[2.2.1]hept-2-yl}-2-(1-methyl-1H-pyrazol-4-yl)pyrimidine-5-carbonitrile;

4-{(1S,4R)-5-[3-(1-hydroxy-1-methylethyl)phenyl]-2,5-diazabicyclo[2.2.1]hept-2-yl}-2-(1-methyl-1H-pyrazol-4-yl)pyrimidine-5-carbonitrile;

2-(1-methyl-1H-pyrazol-4-yl)-4-[(1S,4R)-5-pyridin-3-yl-2,5-diazabicyclo[2.2.1]hept-2-yl]pyrimidine-5-carbonitrile;

4-[(1S,4S)-5-(3-fluorophenyl)-2,5-diazabicyclo[2.2.1]hept-2-yl]-2-(1H-pyrazol-4-yl)pyrimidine-5-carbonitrile;

4-{(1S,4R)-5-[3-(2-fluoroethoxy)phenyl]-2,5-diazabicyclo[2.2.1]hept-2-yl}-2-(1-methyl-H-pyrazol-4-yl)pyrimidine-5-carbonitrile;

2-(1-methyl-1H-pyrazol-4-yl)-4-{(1S,4R)-5-[3-(1H-pyrrol-1-yl)phenyl]-2,5-diazabicyclo[2.2.1]hept-2-yl}pyrimidine-5-carbonitrile;

2-(1-methyl-1H-pyrazol-4-yl)-4-[(1S,4R)-5-(3-nitrophenyl)-2,5-diazabicyclo[2.2.1]hept-2-yl]pyrimidine-5-carbonitrile;

4-[(1S,4R)-5-(3-cyclopropylphenyl)-2,5-diazabicyclo[2.2.1]hept-2-yl]-2-(1-methyl-1H-pyrazol-4-yl)pyrimidine-5-carbonitrile;

4-{(1S,4R)-5-[3-(1-methylcyclopropyl)phenyl]-2,5-diazabicyclo[2.2.1]hept-2-yl}-2-(1-methyl-1H-pyrazol-4-yl)pyrimidine-5-carbonitrile;

3-{(1R,4S)-5-[5-cyano-2-(1-methyl-1H-pyrazol-4-yl)pyrimidin-4-yl]-2,5-diazabicyclo[2.2.1]hept-2-yl}-N-methylbenzamide;

4-[(1S,4R)-5-(3-methoxyphenyl)-2,5-diazabicyclo[2.2.1]hept-2-yl]-2-(1-methyl-1H-pyrazol-4-yl)pyrimidine-5-carbonitrile;

2-(1-methyl-1H-pyrazol-4-yl)-4-{(1S,4R)-5-[3-(methylsulfonyl)phenyl]-2,5-diazabicyclo[2.2.1]hept-2-yl}pyrimidine-5-carbonitrile;

4-[(1S,4S)-5-(3-fluorophenyl)-2,5-diazabicyclo[2.2.1]hept-2-yl]-2-(1-methyl-1H-pyrazol-4-yl)pyrimidine-5-carbonitrile;

4-[(1R,4S)-5-(3-fluorophenyl)-2,5-diazabicyclo[2.2.1]hept-2-yl]-2-(1H-pyrrolo[2,3-b]pyridin-4-yl)pyrimidine-5-carbonitrile;

4-[(1R,4S)-5-(3-fluorophenyl)-2,5-diazabicyclo[2.2.1]hept-2-yl]-2-(1H-pyrrolo[2,3-b]pyridin-5-yl)pyrimidine-5-carbonitrile;

4-[(1R,4S)-5-(3-fluorophenyl)-2,5-diazabicyclo[2.2.1]hept-2-yl]-2-(5-methylpyridin-3-yl)pyrimidine-5-carbonitrile;

4-[(1R,4S)-5-(3-fluorophenyl)-2,5-diazabicyclo[2.2.1]hept-2-yl]-2-(1H-indazol-4-yl)pyrimidine-5-carbonitrile;

4-[(1R,4S)-5-(3-fluorophenyl)-2,5-diazabicyclo[2.2.1]hept-2-yl]-2-isoquinolin-5-ylpyrimidine-5-carbonitrile;

4-[(1S,4R)-5-(3-fluorophenyl)-2,5-diazabicyclo[2.2.1]hept-2-yl]-2-(1,4,6,7-tetrahydro-5H-pyrazolo[4,3-c]pyridin-5-yl)pyrimidine-5-carbonitrile;

4-[(1S,4R)-5-(3-fluorophenyl)-2,5-diazabicyclo[2.2.1]hept-2-yl]-2-morpholin-4-ylpyrimidine-5-carbonitrile;

4-[(1S,4R)-5-(cyclopropylcarbonyl)-2,5-diazabicyclo[2.2.1]hept-2-yl]-2-(1-methyl-1H-pyrazol-4-yl)pyrimidine-5-carbonitrile;

4-[(1S,4R)-5-(cyclopropylsulfonyl)-2,5-diazabicyclo[2.2.1]hept-2-yl]-2-(1-methyl-1H-pyrazol-4-yl)pyrimidine-5-carbonitrile;

4-[(1S,4R)-5-(cyclopropylmethyl)-2,5-diazabicyclo[2.2.1]hept-2-yl]-2-(1-methyl-1H-pyrazol-4-yl)pyrimidine-5-carbonitrile;

(1R,4S)-5-[5-cyano-2-(1-methyl-1H-pyrazol-4-yl)pyrimidin-4-yl]-N-ethyl-2,5-diazabicyclo[2.2.1]heptane-2-carboxamide;

4-[(1S,4R)-5-(2,2-dimethylpropanoyl)-2,5-diazabicyclo[2.2.1]hept-2-yl]-2-(1-methyl-1H-pyrazol-4-yl)pyrimidine-5-carbonitrile;

4-[(1S,4R)-5-(3-fluoro-2,2-dimethylpropanoyl)-2,5-diazabicyclo[2.2.1]hept-2-yl]-2-(1-methyl-1H-pyrazol-4-yl)pyrimidine-5-carbonitrile;

4-{(1S,4R)-5-[(3-methyloxetan-3-yl)carbonyl]-2,5-diazabicyclo[2.2.1]hept-2-yl}-2-(1-methyl-1H-pyrazol-4-yl)pyrimidine-5-carbonitrile;

4-[(1S,4R)-5-{[1-(methoxymethyl)cyclopropyl]carbonyl}-2,5-diazabicyclo[2.2.1]hept-2-yl]-2-(1-methyl-1H-pyrazol-4-yl)pyrimidine-5-carbonitrile;

4-[(1S,4R)-5-(cyclobutylcarbonyl)-2,5-diazabicyclo[2.2.1]hept-2-yl]-2-(1-methyl-1H-pyrazol-4-yl)pyrimidine-5-carbonitrile;

2-(1-methyl-1H-pyrazol-4-yl)-4-[(1S,4R)-5-(thiophen-2-ylcarbonyl)-2,5-diazabicyclo[2.2.1]hept-2-yl]pyrimidine-5-carbonitrile;

2-(1-methyl-1H-pyrazol-4-yl)-4-[(1S,4R)-5-(1,3-oxazol-4-ylcarbonyl)-2,5-diazabicyclo[2.2.1]hept-2-yl]pyrimidine-5-carbonitrile;

2-(1-methyl-1H-pyrazol-4-yl)-4-[(1S,4R)-5-(oxetan-3-ylacetyl)-2,5-diazabicyclo[2.2.1]hept-2-yl]pyrimidine-5-carbonitrile;

4-{(1S,4R)-5-[(1-methylethyl)sulfonyl]-2,5-diazabicyclo[2.2.1]hept-2-yl}-2-(1-methyl-H-pyrazol-4-yl)pyrimidine-5-carbonitrile;

2-(1-methyl-1H-pyrazol-4-yl)-4-[(1S,4R)-5-(propylsulfonyl)-2,5-diazabicyclo[2.2.1]hept-2-yl]pyrimidine-5-carbonitrile;

4-[(1S,4R)-5-(cyclopentylsulfonyl)-2,5-diazabicyclo[2.2.1]hept-2-yl]-2-(1-methyl-1H-pyrazol-4-yl)pyrimidine-5-carbonitrile;

4-[(1S,4R)-5-(3-fluoropropyl)-2,5-diazabicyclo[2.2.1]hept-2-yl]-2-(1-methyl-1H-pyrazol-4-yl)pyrimidine-5-carbonitrile;

4-[4-(3-fluorophenyl)-3,3-dimethylpiperazin-1-yl]-2-(1-methyl-H-pyrazol-4-yl)pyrimidine-5-carbonitrile;

4-[4-(3-fluorophenyl)piperazin-1-yl]-2-(1-methyl-1H-pyrazol-4-yl)pyrimidine-5-carbonitrile;

4-[(3R)-4-(3-fluorophenyl)-3-methylpiperazin-1-yl]-2-(1-methyl-1H-pyrazol-4-yl)pyrimidine-5-carbonitrile;

4-[8-(3-fluorophenyl)-3,8-diazabicyclo[3.2.1]oct-3-yl]-2-(1-methyl-1H-pyrazol-4-yl)pyrimidine-5-carbonitrile;

4-[(3R)-4-(cyclopropylcarbonyl)-3-methylpiperazin-1-yl]-2-(1-methyl-1H-pyrazol-4-yl)pyrimidine-5-carbonitrile;

4-[(3R)-3-methyl-4-propanoylpiperazin-1-yl]-2-(1-methyl-1H-pyrazol-4-yl)pyrimidine-5-carbonitrile;

4-[(3R)-4-(cyclobutylcarbonyl)-3-methylpiperazin-1-yl]-2-(1-methyl-1H-pyrazol-4-yl)pyrimidine-5-carbonitrile;

4-{(3R)-3-methyl-4-[(1-methylcyclopropyl)carbonyl]piperazin-1-yl}-2-(1-methyl-1H-pyrazol-4-yl)pyrimidine-5-carbonitrile;

4-{(3R)-4-[(2,2-difluorocyclobutyl)carbonyl]-3-methylpiperazin-1-yl}-2-(1-methyl-1H-pyrazol-4-yl)pyrimidine-5-carbonitrile;

4-[(3R)-4-(cyclopentylcarbonyl)-3-methylpiperazin-1-yl]-2-(1-methyl-H-pyrazol-4-yl)pyrimidine-5-carbonitrile;

2-(1-methyl-1H-pyrazol-4-yl)-4-[(3R)-3-methyl-4-(spiro[2.4]hept-1-ylcarbonyl)piperazin-1-yl]pyrimidine-5-carbonitrile;

4-[(3R)-3-methyl-4-{[(1R,2R)-2-methylcyclopropyl]carbonyl}piperazin-1-yl]-2-(1-methyl-1H-pyrazol-4-yl)pyrimidine-5-carbonitrile;

4-[(3R)-3-methyl-4-{[(1S,2R)-2-methylcyclopropyl]carbonyl}piperazin-1-yl]-2-(1-methyl-1H-pyrazol-4-yl)pyrimidine-5-carbonitrile;

4-[(3R)-4-(3-fluorophenyl)-3-methylpiperazin-1-yl]-2-(1-methyl-1H-pyrazol-4-yl)pyrimidine-5-carbonitrile;

4-[(3R)-3-methyl-4-(3-nitrophenyl)piperazin-1-yl]-2-(1-methyl-H-pyrazol-4-yl)pyrimidine-5-carbonitrile;

4-[(3R)-4-(3-cyanophenyl)-3-methylpiperazin-1-yl]-2-(1-methyl-1H-pyrazol-4-yl)pyrimidine-5-carbonitrile;

4-{(3R)-3-methyl-4-[3-(methylsulfonyl)phenyl]piperazin-1-yl}-2-(1-methyl-H-pyrazol-4-yl)pyrimidine-5-carbonitrile;

3-{2-[(3R)-4-(cyclopropylcarbonyl)-3-methylpiperazin-1-yl]-4-(1-methyl-1H-pyrazol-4-yl)pyrimidin-5-yl}prop-2-yn-1-ol;

2-[(3R)-4-(cyclopropylcarbonyl)-3-methylpiperazin-1-yl]-6-(1-methyl-1H-pyrazol-4-yl)pyrimidine-4-carbonitrile;

6-[(3R)-4-(cyclopropylcarbonyl)-3-methylpiperazin-1-yl]-2-(1-methyl-1H-pyrazol-4-yl)pyrimidine-4-carbonitrile;

2-[(3R)-4-(cyclopropylcarbonyl)-3-methylpiperazin-1-yl]-4-(1-methyl-1H-pyrazol-4-yl)pyrimidine-5-carbonitrile;

2-[(3R)-4-(cyclopropylcarbonyl)-3-methylpiperazin-1-yl]-5-[5-(1-methylethyl)-1,3-oxazol-2-yl]-4-(1-methyl-1H-pyrazol-4-yl)pyrimidine;

4-[(3R)-4-(cyclopropylcarbonyl)-3-(2-methylpropyl)piperazin-1-yl]-2-(1-methyl-1H-pyrazol-4-yl)pyrimidine-5-carbonitrile;

4-[(3S)-4-(cyclopropylcarbonyl)-3-(hydroxymethyl)piperazin-1-yl]-2-(1-methyl-1H-pyrazol-4-yl)pyrimidine-5-carbonitrile;

2-[(3R)-4-(cyclopropylcarbonyl)-3-methylpiperazin-1-yl]-5-(3-methylbut-1-yn-1-yl)-4-(1-methyl-1H-pyrazol-4-yl)pyrimidine;

2-[(3R)-4-(cyclopropylcarbonyl)-3-methylpiperazin-1-yl]-5-ethynyl-4-(1-methyl-1H-pyrazol-4-yl)pyrimidine;

2-[(3R)-4-(cyclopropylcarbonyl)-3-methylpiperazin-1-yl]-4-(1-methyl-1H-pyrazol-4-yl)-5-(methylsulfanyl)pyrimidine;

2-[(3R)-4-(cyclopropylcarbonyl)-3-methylpiperazin-1-yl]-5-(difluoromethyl)-4-(1-methyl-1H-pyrazol-4-yl)pyrimidine;

ethyl 2-[(3R)-4-(cyclopropylcarbonyl)-3-methylpiperazin-1-yl]-4-(1-methyl-H-pyrazol-4-yl)pyrimidine-5-carboxylate;

5-chloro-4-[(3R)-4-(cyclopropylcarbonyl)-3-methylpiperazin-1-yl]-2-(1-methyl-1H-pyrazol-4-yl)pyrimidine;

4-amino-6-[(3R)-4-(cyclopropylcarbonyl)-3-methylpiperazin-1-yl]-2-(1-methyl-1H-pyrazol-4-yl)pyrimidine-5-carbonitrile;

1-{5-cyano-6-[(3R)-4-(cyclopropylcarbonyl)-3-methylpiperazin-1-yl]-2-(1-methyl-H-pyrazol-4-yl)pyrimidin-4-yl}-3-(1-methylethyl)urea;

N-{5-cyano-6-[(3R)-4-(cyclopropylcarbonyl)-3-methylpiperazin-1-yl]-2-(1-methyl-H-pyrazol-4-yl)pyrimidin-4-yl}acetamide;

4-[(3R)-4-(cyclopropylcarbonyl)-3-methylpiperazin-1-yl]-2-(1-methyl-1H-pyrazol-4-yl)-6-[(2,2,2-trifluoroethyl)amino]pyrimidine-5-carbonitrile;

4-chloro-6-[(3R)-4-(cyclopropylcarbonyl)-3-methylpiperazin-1-yl]-2-(1-methyl-1H-pyrazol-4-yl)pyrimidine-5-carbonitrile;

4-[(3R)-4-(cyclopropylcarbonyl)-3-methylpiperazin-1-yl]-6-ethyl-2-(1-methyl-1H-pyrazol-4-yl)pyrimidine-5-carbonitrile;

4-(cyclobutylamino)-6-[(3R)-4-(cyclopropylcarbonyl)-3-methylpiperazin-1-yl]-2-(1-methyl-1H-pyrazol-4-yl)pyrimidine-5-carbonitrile;

4-[(3R)-4-(cyclopropylcarbonyl)-3-methylpiperazin-1-yl]-2-(1-methyl-1H-pyrazol-4-yl)-6-(phenylamino)pyrimidine-5-carbonitrile;

4-chloro-2-[(3R)-4-(cyclopropylcarbonyl)-3-methylpiperazin-1-yl]-6-(1-methyl-1H-pyrazol-4-yl)pyrimidine-5-carbonitrile;

4-[(3R)-4-(cyclopropylcarbonyl)-3-methylpiperazin-1-yl]-6-methyl-2-(1-methyl-1H-pyrazol-4-yl)pyrimidine-5-carbonitrile;

4-[(3R)-4-(cyclopropylcarbonyl)-3-methylpiperazin-1-yl]-2-[1-methyl-5-(3,3,3-trifluoropropyl)-1H-pyrazol-4-yl]pyrimidine-5-carbonitrile;

2-[(3R)-4-(cyclopropylcarbonyl)-3-methylpiperazin-1-yl]-4-(2-methoxyethyl)-6-(1-methyl-1H-pyrazol-4-yl)pyrimidine-5-carbonitrile;

4-(3-cyano-1-methyl-1H-pyrazol-4-yl)-2-[(3R)-4-(cyclopropylcarbonyl)-3-methylpiperazin-1-yl]pyrimidine-5-carbonitrile;

4-(3-amino-1-methyl-1H-pyrazol-4-yl)-2-[(3R)-4-(cyclopropylcarbonyl)-3-methylpiperazin-1-yl]pyrimidine-5-carbonitrile;

4-[(3R)-4-(cyclopropylcarbonyl)-3-methylpiperazin-1-yl]-2-(5,6-dihydro-4H-pyrrolo[1,2-b]pyrazol-3-yl)pyrimidine-5-carbonitrile;

1-{5-cyano-6-[(3R)-4-(cyclopropylcarbonyl)-3-methylpiperazin-1-yl]-2-(1-methyl-1H-pyrazol-4-yl)pyrimidin-4-yl}-3-(2,2,2-trifluoroethyl)urea;

1-{5-cyano-6-[(3R)-4-(cyclopropylcarbonyl)-3-methylpiperazin-1-yl]-2-(1-methyl-H-pyrazol-4-yl)pyrimidin-4-yl}-3-cyclobutylurea;

4-[(3R)-4-(cyclopropylcarbonyl)-3-methylpiperazin-1-yl]-2-(1-methyl-H-pyrazol-4-yl)-6-[(oxetan-3-ylmethyl)amino]pyrimidine-5-carbonitrile;

4-[(3R)-4-(cyclopropylcarbonyl)-3-methylpiperazin-1-yl]-2-(1-methyl-H-pyrazol-4-yl)-6-[(3,3,3-trifluoropropyl)amino]pyrimidine-5-carbonitrile;

4-[(3R)-4-(cyclopropylcarbonyl)-3-methylpiperazin-1-yl]-6-[(1-methylethyl)amino]-2-(1-methyl-1H-pyrazol-4-yl)pyrimidine-5-carbonitrile;

4-[(3R)-4-(cyclopropylcarbonyl)-3-methylpiperazin-1-yl]-6-[(2-methylpropyl)amino]-2-(1-methyl-1H-pyrazol-4-yl)pyrimidine-5-carbonitrile;
4-[(3R)-4-(cyclopropylcarbonyl)-3-methylpiperazin-1-yl]-2-(1-methyl-H-pyrazol-4-yl)-6-(2,2,2-trifluoroethoxy)pyrimidine-5-carbonitrile;
4-[(3R)-4-(cyclopropylcarbonyl)-3-methylpiperazin-1-yl]-2-(1-methyl-1H-pyrazol-4-yl)-6-[3-(trifluoromethyl)azetidin-1-yl]pyrimidine-5-carbonitrile;
4-[(3R)-4-(cyclopropylcarbonyl)-3-methylpiperazin-1-yl]-2-(1-methyl-1H-pyrazol-4-yl)-6-propylpyrimidine-5-carbonitrile;
2-[(3R)-4-(cyclopropylcarbonyl)-3-methylpiperazin-1-yl]-4-(1-methyl-H-pyrazol-4-yl)-6-propylpyrimidine-5-carbonitrile;
2-[(3R)-4-(cyclopropylcarbonyl)-3-methylpiperazin-1-yl]-4-(1-methyl-1H-pyrazol-4-yl)-6-(3,3,3-trifluoropropyl)pyrimidine-5-carbonitrile;
4-cyclopropyl-2-[(3R)-4-(cyclopropylcarbonyl)-3-methylpiperazin-1-yl]-6-(1-methyl-1H-pyrazol-4-yl)pyrimidine-5-carbonitrile;
4-[(3R)-4-(cyclopropylcarbonyl)-3-methylpiperazin-1-yl]-2-(1,3-dimethyl-1H-pyrazol-4-yl)pyrimidine-5-carbonitrile;
4-[(3R)-4-(cyclopropylcarbonyl)-3-methylpiperazin-1-yl]-2-(1,5-dimethyl-1H-pyrazol-4-yl)pyrimidine-5-carbonitrile; or
4-[(3R)-4-(cyclopropylcarbonyl)-3-methylpiperazin-1-yl]-2-[1-(difluoromethyl)-1H-pyrazol-4-yl]pyrimidine-5-carbonitrile.

In a first embodiment of the invention, A is selected from: pyrazolyl,

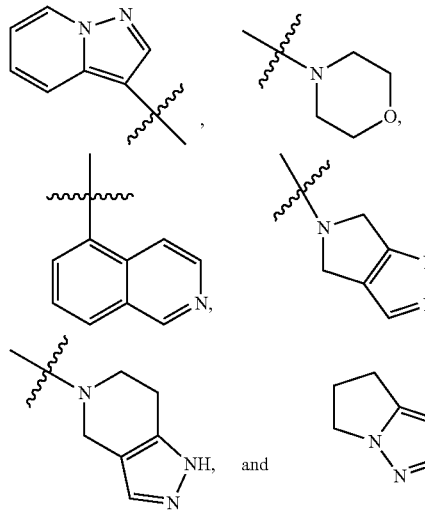

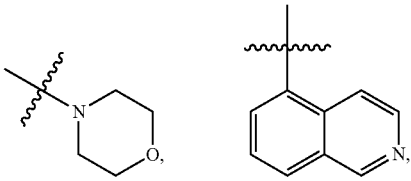

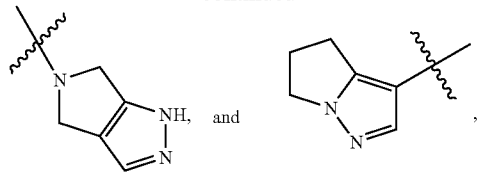

and the other groups are provided in the general formulas Ia and Ib.

In a second embodiment of the invention, A is selected from: pyrazolyl, and the other groups are provided in the general formulas Ia and Ib above or as in the first embodiment.

In a third embodiment of the invention, A is pyrazolyl, and the other groups are provided in the general formulas Ia and Ib above or as in the first and second embodiments.

In a fourth embodiment of the invention, A is selected from pyridinyl,

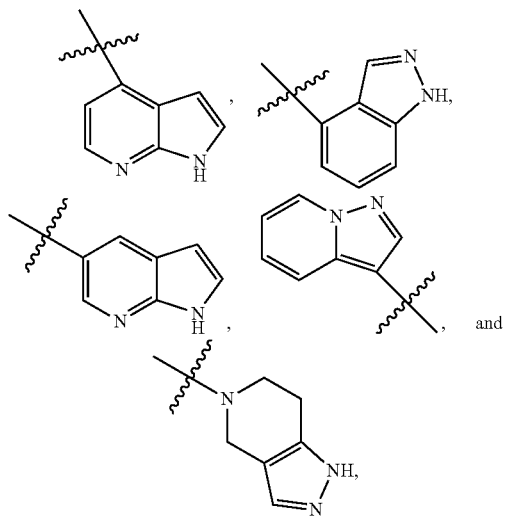

and the other groups are provided in the general formulas Ia and Ib above or as in the first through third embodiments.

In a fifth embodiment of the invention, A is selected from pyridinyl,

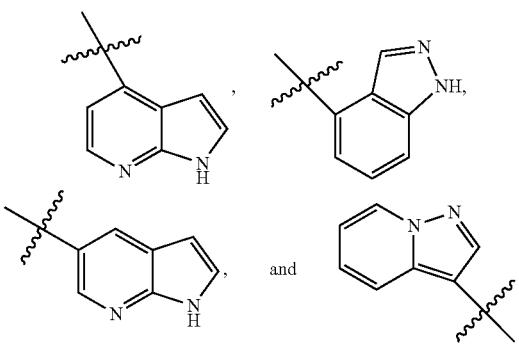

and the other groups are provided in the general formulas Ia and Ib above or as in the first through fourth embodiments.

In a sixth embodiment, each $R^2$ is independently selected from methyl, amino, difluoromethyl, 3,3,3-trifluoropropyl, and cyano, and the other groups are provided in the general formulas Ia and Ib above or as in the first through fifth embodiments. In a variant of this embodiment, each $R^2$ is independently selected from methyl, difluoromethyl, and 3,3,3-trifluoropropyl, and the other groups are provided in the general formulas Ia and Ib above or as in the first through fifth embodiments.

In a seventh embodiment, each $R^1$ is independently selected from hydrogen, chloro, amino, cyano, $C_{1-6}$ alkyl, $C_{1-6}$ haloalkyl, $C_{3-12}$ heterocycloalkyl($C_{1-6}$ alkyl)$_{0-1}$, $C_{3-12}$ cycloalkyl($C_{1-6}$ alkyl)$_{0-1}$, $C_{1-6}$ alkyl(amino)$_{0-1}$ carbonylamino, $C_{1-6}$ haloalkyl(amino)$_{0-1}$ carbonylamino, $C_{3-12}$ cycloalkyl(amino)$_{0-1}$ carbonylamino, $C_{1-6}$ alkylamino, $C_{1-6}$ haloalkylamino, $C_{3-12}$ cycloalkyl($C_{1-6}$ alkyl)$_{0-1}$ amino, $C_{3-12}$ heterocycloalkyl($C_{1-6}$ alkyl)$_{0-1}$amino, $C_{5-7}$aryl ($C_{1-6}$ alkyl)$_{0-1}$amino, $C_{1-6}$ alkyloxy($C_{0-6}$ alkyl), and $C_{1-6}$ haloalkyl oxy ($C_{0-6}$ alkyl), and the other groups are provided in the general formulas Ia and Ib above or as in the first through sixth embodiments.

In a variant of this embodiment, each R is independently selected from hydrogen, chloro, amino, cyano, $C_{1-6}$ alkyl, $C_{1-6}$ haloalkyl, $C_{3-12}$ heterocycloalkyl($C_{1-6}$ alkyl)$_{0-1}$, $C_{3-12}$ cycloalkyl($C_{1-6}$ alkyl)$_{0-1}$, $C_{1-6}$ alkyl(amino)$_{0-1}$ carbonylamino, $C_{1-6}$ haloalkyl(amino)$_{0-1}$ carbonylamino, $C_{3-12}$ cycloalkyl(amino)$_{0-1}$ carbonylamino, $C_{3-12}$ heterocycloalkyl (amino)$_{0-1}$carbonylamino, $C_{1-6}$ alkylamino, $C_{1-6}$ haloalkylamino, $C_{3-12}$ cycloalkyl($C_{1-6}$ alkyl)$_{0-1}$ amino, $C_{3-12}$ heterocycloalkyl($C_{1-6}$ alkyl)$_{0-1}$amino, $C_{5-7}$aryl ($C_{1-6}$ alkyl)$_{0-1}$amino, $C_{1-6}$ alkyloxy($C_{0-6}$ alkyl), $C_{1-6}$ haloalkyl oxy($C_{0-6}$ alkyl), $C_{3-12}$ cycloalkyloxy($C_{0-6}$ alkyl), or $C_{3-12}$ heterocycloalkyl oxy($C_{0-6}$ alkyl); wherein said amino, $C_{1-6}$ alkyl, $C_{1-6}$ haloalkyl, $C_{3-12}$ heterocycloalkyl($C_{1-6}$ alkyl)$_{0-1}$, $C_{3-12}$ cycloalkyl($C_{1-6}$ alkyl)$_{0-1}$, $C_{1-6}$ alkyl(amino)$_{0-1}$ carbonylamino, $C_{1-6}$ haloalkyl(amino)$_{0-1}$ carbonylamino, $C_{3-12}$ cycloalkyl(amino)$_{0-1}$ carbonylamino, $C_{1-6}$ alkylamino, $C_{1-6}$ haloalkylamino, $C_{3-12}$ cycloalkyl($C_{1-6}$ alkyl)$_{0-1}$ amino, $C_{3-12}$ heterocycloalkyl($C_{1-6}$ alkyl)$_{0-1}$amino, $C_{5-7}$aryl ($C_{1-6}$ alkyl)$_{0-1}$amino, $C_{1-6}$ alkyloxy($C_{0-6}$ alkyl), and $C_{1-6}$ haloalkyl oxy ($C_{0-6}$ alkyl), is independently substituted by 0, 1, 2, or 3 $R^8$ independently selected from amino, hydroxy, $C_{1-6}$ alkyl, $C_{1-6}$ haloalkyl, and $C_{1-6}$ alkyloxy and and the other groups are provided in the general formulas Ia and Ib above or as in the first through sixth embodiments.

In a eighth embodiment, each $R^1$ is independently selected from hydrogen, chloro, amino, cyano, isopropylaminocarbonylamino, methylcarbonylamino, (2,2,2-trifluoroethyl)amino, cyclobutylaminocarbonylamino, ethyl, cyclobutylamino, phenylamino, methyl, methyloxyethyl, methoxyethyl, (2,2,2-trifluoroethyl)aminocarbonylamino, (oxetanylmethyl)amino, (3,3,3-trifluoropropyl)amino, isopropylamino, (2-methylpropyl)amino, 2,2,2,-trifluoroethoxy, azetidinyl, propyl, 3,3,3-trifluoropropyl, and cycloproyl, and the other groups are provided in the general formulas Ia and Ib above or as in the first through seventh embodiments. In a variant of this embodiment, each R is independently selected from hydrogen, chloro, amino, cyano, isopropylaminocarbonylamino, methylcarbonylamino, (2,2,2-trifluoroethyl)amino, cyclobutylaminocarbonylamino, ethyl, cyclobutylamino, phenylamino, methyl, methyloxyethyl, methoxyethyl, (2,2,2-trifluoroethyl)aminocarbonylamino, (oxetanylmethyl)amino, (3,3,3-trifluoropropyl)amino, isopropylamino, (2-methylpropyl)amino, 2,2,2-trifluoroethoxy, azetidinyl, propyl, and cycloproyl, and the other groups are provided in the general formulas Ia and Ib above or as in the first through seventh embodiments.

In a variant of this embodiment, each R is independently selected from hydrogen, chloro, amino, cyano, isopropylaminocarbonylamino, methylcarbonylamino, (2,2,2-trifluoroethyl)amino, cyclobutylaminocarbonylamino, ethyl, cyclobutylamino, phenylamino, methyl, methyloxyethyl, methoxyethyl, (2,2,2-trifluoroethyl)aminocarbonylamino, (oxetanylmethyl)amino, (3,3,3-trifluoropropyl)amino, isopropylamino, (2-methylpropyl)amino, 2,2,2,-trifluoroethoxy, azetidinyl, propyl, 3,3,3-trifluoropropyl, and cycloproyl, wherein said amino, isopropylaminocarbonylamino, methylcarbonylamino, (2,2,2-trifluoroethyl)amino, cyclobutylaminocarbonylamino, ethyl, cyclobutylamino, phenylamino, methyl, methyloxyethyl, methoxyethyl, (2,2,2-trifluoroethyl)aminocarbonylamino, (oxetanylmethyl) amino, (3,3,3-trifluoropropyl)amino, isopropylamino, (2-methylpropyl)amino, 2,2,2,-trifluoroethoxy, azetidinyl, propyl, 3,3,3-trifluoropropyl, or cycloproyl, is independently substituted by 0, 1, 2, or 3 $R^8$ independently selected from amino, hydroxy, $C_{1-6}$ alkyl, $C_{1-6}$ haloalkyl, and $C_{1-6}$ alkyloxy and the other groups are provided in the general formulas Ia and Ib above or as in the first through seventh embodiments.

In an ninth embodiment of the invention, each $R^8$ is independently selected from amino, $C_{1-6}$ alkyl, and $C_{1-6}$ haloalkyl, and the other groups are provided in the general formulas Ia and Ib above or as in the first through eighth embodiments.

In a tenth embodiment of the invention, each $R^8$ is independently selected from methyl, amino and trifluoromethyl, and the other groups are provided in the general formulas Ia and Ib above or as in the first through ninth embodiments. In a variant of this embodiment, each $R^8$ is independently methyl or trifluoromethyl, and the other groups are provided in the general formulas Ia and Ib above or as in the first through ninth embodiments In a eleventh embodiment, each $R^4$ is independently selected from methyl, 2-methylpropyl, and hydroxymethyl, and the other groups are provided in the general formulas Ia and Ib above or as in the first through tenth embodiments.

In the twelfth embodiment, each $R^5$ is independently selected from cyano, $C_{1-6}$ haloalkyl, fluoro, $C_{1-6}$ alkyl, —($C_{1-6}$ alkyl)OH, $C_{1-6}$ alkoxy, $C_{1-6}$ alkoxy$C_{1-6}$ alkyl, pyrrolyl, nitro, $C_{3-12}$cycloalkyl, $C_{1-4}$ alkyl aminocarbonyl, and $C_{1-4}$ alkylsufonyl, and other groups are provided in the general formulas Ia and Ib above or as in the first through eleventh embodiments.

In a thirteenth embodiment, each $R^5$ is independently selected from cyano, difluoromethyl, fluoro, isopropyl, ethoxy, pyrrolyl, nitro, cyclopropyl, methylaminocarbonyl, methoxy, methylsulfonyl, methoxymethyl and methyl, and other groups are provided in the general formulas Ia and Ib above or as in the first through twelfth embodiments. In a variant of this embodiment, each $R^5$ is independently selected from cyano, difluoromethyl, fluoro, isopropyl, pyrrolyl, nitro, cyclopropyl, methylaminocarbonyl, methoxy, methylsulfonyl, and methoxymethyl, and other groups are provided in the general formulas Ia and Ib above or as in the first through twelfth embodiments.

In a fourteenth embodiment of the invention, each $R^6$ is independently selected from fluoro, hydroxy, and methyl, and other groups are provided in the general formulas Ia and Ib above or as in the first through thirteenth embodiments. In a variant of this embodiment, each $R^6$ is independently hydroxy, or methyl, and other groups are provided in the general formulas Ia and Ib above or as in the first through thirteenth embodiments.

In a fifteenth embodiment, each R is independently selected from methyl, ethyl, methylethyl, fluoro, hydroxy, and $C_{1-6}$ alkoxy, and other groups are provided in the general formulas Ia and Ib above or as in the first through fourteenth embodiments.

In a sixteenth embodiment, each $R^7$ is methylethyl and other groups are provided in the general formulas Ia and Ib above or as in the first through fifteenth embodiments.

In a seventeenth embodiment, each $R^3$ is hydrogen, methyl, cyano or amino and other groups are provided in the general formulas Ia and Ib above or as in the first through sixteenth embodiments.

The invention also encompasses pharmaceutical compositions containing a compound of formulas Ia or Ib, and methods for treatment or prevention of PI3K-delta mediated diseases using compounds of formulas Ia and Ib. It should be noted that here, the compounds of formulas Ia or Ib also include the compounds of embodiments 1-17.

One aspect of the present invention is to provide compounds that can inhibit the biological activity of human PI3K-delta. Another aspect of the invention is to provide methods of selectively modulating human PI3K-delta activity and thereby promoting medical treatment of diseases mediated by PI3K-delta dysfunction.

In one embodiment of the invention, the compounds of formulas Ia and Ib inhibit PI3K-delta activity in biochemical and cell-based assays and exhibit therapeutic activity in medical conditions in which PI3K-delta activity is excessive or undesirable.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "-O-alkyl," etc. The invention is described using the following definitions unless otherwise indicated.

When any variable (e.g. aryl, heteroaryl, $R^1$, $R^5$, etc.) occurs more than one time in any constituent, its definition on each occurrence is independent at every other occurrence.

Also, combinations of substituents/or variables are permissible only if such combinations result in stable compounds.

The wavy line ∿∿∿ as used herein, indicates a point of attachment to the rest of the compound.

The term "$C_{1-6}$" includes alkyls containing 6, 5, 4, 3, 2, or 1 carbon atoms.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

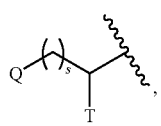

wherein s is an integer equal to zero, 1 or 2, the structure is

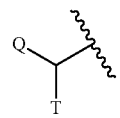

when s is zero.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to

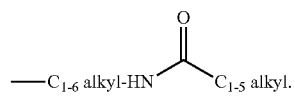

Lines drawn into the ring systems, such as, for example:

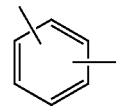

indicate that the indicated line (bond) may be attached to any of the substitutable ring carbon atoms.

The term "alkyl," as used herein, refers to an aliphatic hydrocarbon group having one of its hydrogen atoms replaced with a bond. An alkyl group may be straight or branched and contain from about 1 to about 10 carbon atoms. In different embodiments, an alkyl group contains from 1 to 6 carbon atoms ($C_{1-6}$ alkyl) or from about 1 to about 3 carbon atoms ($C_{1-3}$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "alkanoyl" has the general formulas of RC=O, where R may be aliphatic alicyclic or aromatic.

The term "alkoxy" represents a linear or branched alkyl group of indicated number of carbon atoms attached through an oxygen bridge.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "aryl," as used herein, refers to an aromatic monocyclic or multicyclic ring system comprising from about 6 to about 14 carbon atoms. In one embodiment, an aryl group contains from about 6 to about 10 carbon atoms. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

"Carboxy" refers to the functional group —C(O)OR, for example: ethylcarboxy is

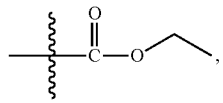 [SMILES: *C(=O)OCC]

phenylcarboxy is

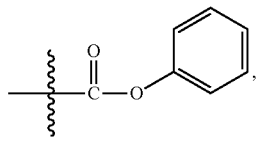

and cyclopropycarboxy is

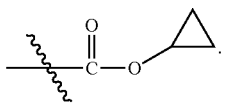 [SMILES: *C(=O)OC1CC1]

"Celite®" (Fluka) diatomite is diatomaceous earth, and can be referred to as "celite".

"Cycloalkyl" means a carbocyclic ring system having 3 to 12 ring carbon atoms; said ring system may be (a) a monocyclic saturated carbocycle or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.4]heptane, spiro[2.2]pentane), or are bridged groups (e.g., norbomane). Additional examples within the above meaning include, but are not limited to, cyclopropane, cyclobutane, cyclopentane, cyclohexane, cyclooctyl, decalin, spiro[4.5]decane, spiro[2.5]oxtyl, bicyclo[2.2.2]octane, and the like.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "heteroaryl," as used herein, refers to an aromatic monocyclic or multicyclic ring system having at least one aromatic ring comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. In another embodiment, a heteroaryl group is bicyclic and has 9 or 10 ring atoms. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, pyrrolyl, triazolyl, 1,2,4-thiadiazolyl, indazolyl, pyridinyl, pyrazinyl, pyridazinyl, quinoxalinyl, phthalazinyl, oxindolyl, 4,6-dihydropyrrolo[3,4-c]pyrazolyl, pyrarazolo[1,5-a]pyridinyl, pyrrolo[2,3-b]pyrindinyl, imidazo[1,2-a]pyridinyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl, 1,4,6,7-tetrahydro-pyrazolo[4,3-c]pyridinyl, and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, or N, and the remainder of the ring atoms are carbon atoms. A heterocycloalkyl group can be joined via a ring carbon, ring silicon atom or ring nitrogen atom. Said ring system may be (a) a saturated monocyclic ring or a partially unsaturated ring, or (b) a bicyclic saturated carbocycle. For a bicyclic system, within either (a) or (b), the rings are fused across two adjacent ring carbon atoms (e.g., decahydroisoquinoline), at one ring carbon atom (e.g., spiro[2.4]heptyl, spiro[2.2]pentane), or are bridged groups (e.g., 2,5-diazabicyclo[2.2.1]heptyl).

In one embodiment, a heterocycloalkyl group is monocyclic and has from about 3 to about 7 ring atoms. In another embodiment, a heterocycloalkyl group is monocyclic has from about 5 to about 8 ring atoms. In another embodiment, a heterocycloalkyl group is bicyclic and has from about 8 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

"Hydroxyalkyl" refers to an alkyl group as described above in which one or more (in particular 1 to 3) hydrogen atoms have been replaced by hydroxy groups. Examples include CH$_2$OH, CH$_2$CHOH and CHOHCH$_3$.

"Sufanyl" refers to mercapto radical, —SH. For example, methylsulfanyl is —SCH$_3$.

Unless expressly stated to the contrary, an "unsaturated" ring is a partially or fully unsaturated ring. For example, an "unsaturated monocyclic C$_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "oxy" means an oxygen (O) atom. The term "thio" means a sulfur (S) atom. The term "oxo" means "=O". The term "carbonyl" means "C=O." Structural representations of compounds having substituents terminating with a methyl group may display the terminal methyl group either using the characters "CH₃", e.g. "—CH₃" or using a straight line representing the presence of the methyl group, e.g. " —— ", i.e.,

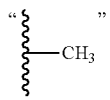

and

have equivalent meanings.

For variable definitions containing terms having repeated terms, e.g., $(CR_iR_j)_r$, where r is the integer 2, Ri is a defined variable, and Rj is a defined variable, the value of Ri may differ in each instance in which it occurs, and the value of Rj may differ in each instance in which it occurs. For example, if Ri and Rj are independently selected from the group consisting of methyl, ethyl, propyl and butyl, then $(CR_iR_j)_2$ can be

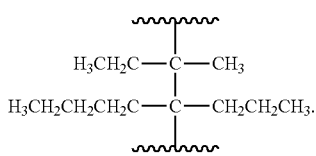

"Patient" for the purposes of the present invention includes humans and other animals, particularly mammals and other organisms. Thus the methods are applicable to both human therapy and veterinary applications.

A "subject" is a human or non-human mammal. In one embodiment, a subject is a human. In one embodiment the subject is a cat or dog. In another embodiment, a subject is a primate. In another embodiment, a subject is a monkey. In another embodiment, a subject is a chimpanzee. In still another embodiment, a subject is a rhesus monkey.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula Ia or Ib, and pharmaceutically acceptable excipients.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —(CR³R³)₂—, each occurrence of the two R³ groups may be the same or different.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

Optical Isomers—Diastereomers—Geometric Isomers—Tautomers

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. (For example, if a compound of formulas Ia and Ib incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, for example, (R and S)-2-Chloro-4-(4-(cyclopropanecarbonyl)-3-methylpiperazin-1-yl)pyrimidine-5-carbonitrile, the "and" indicates a racemic mixture of the enantiomers. That is, the individual enantiomers were not individually isolated.

When the stereomeric nomenclature includes "or", for example, (R or S)-2-Chloro-4-(4-(cyclopropanecarbonyl)-3-methylpiperazin-1-yl)pyrimidine-5-carbonitrile, the "or" indicates that chiral resolution of racemate into individual enantiomers was accomplished but the actual optical activity of the specific enantiomer was not determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

Diastereomeric mixtures can be separated into their individual diastereomers on the basis of their physical chemical differences by methods well known to those skilled in the art, such as, for example, by chromatography (e.g., chiral HPLC column) and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formulas Ia and Ib, subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention.

Prodrugs and Solvates

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of formula Ia or Ib or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "*Prodrugs as Novel Delivery Systems*," Vol. 14 of the A.C.S. Symposium Series, and in *Bioreversible Carriers in Drug Design*, ed. Edward B. Roche, American Pharmaceutical Association and Pergamon Press, 1987.

For example, if a compound of Formula Ia or Ib or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl) amino)ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as 0-dimethylamino-ethyl), carbamoyl-$(C_1$-$C_2)$alkyl, N,N-di $(C_1$-$C_2)$alkylcarbamoyl-(C1-C2)alkyl and piperidino-, pyrrolidino- or morpholino($C_2$-$C_3$)alkyl, and the like.

Similarly, if a compound of Formula Ia or Ib contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate), and the like.

If a compound of Formula Ia or Ib incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$) cycloalkyl, benzyl, or R-carbonyl is a natural α-aminoacyl or natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$)alkyl, carboxy ($C_1$-$C_6$)alkyl, amino($C_1$-$C_4$)alkyl or mono-N- or di-N,N—($C_1$-$C_6$)alkylaminoalkyl, —C($Y^4$)$Y^5$ wherein $Y^4$ is H or methyl and $Y^5$ is mono-N- or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Labelled Compounds

In the compounds of generic Formula Ia or Ib, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula Ia or Ib. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. For example, a methyl group with 3 deuterium forms of hydrogen is depicted as $CD_3$. Isotopically-enriched compounds within generic Formulas Ia and Ib can be prepared without undue experimentation by conventional techniques well known to those skilled in the art or by processes analogous to those described in the Schemes and examples herein using appropriate isotopically-enriched reagents and/or intermediates.

Utilities

Compounds of the Invention have activity for PI3K-delta. Compounds of this invention have been tested using the those skilled in the art or by processes analogous to those described in the Schemes and Examples herein using appropriate isotopically-enriched reagents and/or intermediates.

Suitable in vitro assays for measuring PI3K-delta activity and the inhibition thereof by compounds are known in the art. For further details of an in vitro assay for measuring PI3K-delta, see the Biological Examples herein. Cell-based assays for measurement of in vitro efficacy in treatment of cancer are known in the art. In addition, assays are described in the Biological Examples provided herein.

Suitable in vivo models for cancer are known to those of ordinary skill in the art. See for example, international patent application published as WO 2012/037226 for further details of in vivo models for prostate adenocarcinoma, glioblastoma, lung carcinoma, and melanoma. Following the examples disclosed herein, as well as that disclosed in the art, a person of ordinary skill in the art can determine the activity of a compound of this invention.

Compounds of Formula Ia or Ib may be useful for treating diseases, including autoimmune disorders, inflammatory diseases, and cancers, which are listed below.

Cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adeno-carcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblast-oma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplasia syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Autoimmune diseases: Hashimoto's thyroiditis, systemic lupus erythematosus (SLE), Goodpasture's syndrome, pemphigus, receptor autoimmune diseases, Basedow's disease (Graves' disease), myasthernia gravis, insulin resistant diseases, autoimmune hemolytic anemia, autoimmune thrombocytopenic purpura, autoimmune encephalomyelitis, rheumatism, rheumatoid arthritis, scleroderma, mixed connective tissue disease, polymyositis, pernicious anemia, idiopathic Addison's disease, some types of infertility, glomerulonephritis, bullous pemphigus, Sjogren's syndrome, some types of diabetes, adrenergic agent resistance, chronic active hepatitis, primary biliary cirrhosis, endocrine failure, vitiligo, angiitis, post-cardiac surgery syndrome, urticaria, atopic dermatiti and multiple sclerosis, autoimmune polyglandular disease (also known as autoimmune polyglandular syndrome), autoimmune alopecia; pernicious anemia; vitiligo; autoimmune hypopituatarism, and Guillain-Barre syndrome.

Inflammatory Diseases: asthma, allergic rhinitis, psoriasis, inflammatory arthritis, rheumatoid arthritis, psoriatic arthritis or osteoarthritis, irritable bowel syndrome, ulcerative colitis, Crohn's disease, respiratory allergies (asthma, hay fever, allergic rhinitis) or skin allergies, scleracierma, mycosis fungoides, acute inflammatory responses (such as acute respiratory distress syndrome and ishchemia/reperfusion injury), dermatomyositis, alopecia greata, chronic actinic dermatitis, eczema, Behcet's disease, Pustulosis palmoplanteris, Pyoderma gangrenum, Sezary's syndrome, atopic dermatitis, systemic sclerosis, and morphea.

Central Nervous System Disorders: multiple sclerosis, schizophrenia

Thus, in one embodiment, the invention provides a method of inhibiting PI3K-delta comprising contacting the PI3K-delta with an effective amount of a compound as disclosed herein.

In another embodiment, the invention provides a method of treating a PI3K-delta modulated disease comprising administering to a mammal in need of such treatment a therapeutically effective amount of a compound as disclosed herein.

In another embodiment, the invention provides a method of treating cancer disease mediated by PI3K-delta comprising administering to a mammal in need of such treatment a therapeutically effective amount of a compound as disclosed herein.

Compounds of the invention are also useful as inhibitors of PI3K-delta in vivo for studying the in vivo role of PI3K-delta in biological processes, including the diseases described herein. Accordingly, the invention also comprises a method of inhibiting PI3K-delta in vivo comprising administering a compound or composition of the invention to a mammal.

Accordingly, another aspect of the present invention provides a method for the treatment or prevention of a PI3K-delta mediated disease or disorder comprising administering to a mammal in need thereof a therapeutically effective amount of a compound of formula Ia or Ib. In one embodiment such diseases include asthma and rheumatoid arthritis.

Another aspect of the present invention provides for the use of a compound of formula Ia or Ib in the manufacture of a medicament for the treatment or prevention of a PI3K-delta mediated diseases or disorders.

Dose Ranges

The magnitude of prophylactic or therapeutic dose of a compound of formula Ia or Ib will, of course, vary with the nature and the severity of the condition to be treated and with the particular compound of formula Ia or Ib and its route of administration. It will also vary according to a variety of factors including the age, weight, general health, sex, diet, time of administration, rate of excretion, drug combination and response of the individual patient. In general, the daily dose from about 0.001 milligram of active agent per kilogram body weight of a mammal (mg/kg) to about 100 mg/kg, typically, between 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration to humans may contain from 0.01 mg to 10 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, 400 mg, or 500 mg.

The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of the disease state. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be preferred for continuous infusion.

Pharmaceutical Compositions

Another aspect of the present invention provides pharmaceutical compositions comprising a compound of formula Ia or Ib with a pharmaceutically acceptable carrier. For the treatment of any of the prostanoid mediated diseases compounds of Formula Ia or Ib may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrastemal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or *arachis* oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 m to about 10 m; however, for effective delivery to the distal lung, at least 95 percent of the active agent particles are 5 m or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of Formula Ia or Ib may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula Ia or Ib are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

In certain embodiments, a compound of Formula Ia or Ib is combined in a pharmaceutical combination formulation, or dosing regimen as combination therapy, with one or more other therapeutic agents that has anti-inflammatory or anti-hyperproliferative properties or that is useful for treating an inflammation, immune-response disorder, or hyperproliferative disorder (e.g., cancer). The other therapeutic agent of the pharmaceutical combination formulation or dosing regimen preferably has complementary activities to the compound of Formula Ia or Ib such that they do not adversely affect each other. Such agents are suitably present in combination in amounts that are effective for the purpose intended.

In one embodiment of the invention, the compound of Formula Ia or Ib, or a stereoisomer, tautomer, or pharmaceutically acceptable salt or prodrug thereof, may be co-administered with one or more other therapeutic agents for the treatment and prevention of PI3Kdelta mediated diseases. Thus in another aspect the present invention provides pharmaceutical compositions for treating PI3Kdelta mediated diseases comprising a therapeutically effective amount of a compound of formula Ia or Ib and one or more other therapeutic agents.

In one embodiment for example, for the treatment of the inflammatory diseases rheumatoid arthritis, psoriasis, inflammatory bowel disease, COPD, asthma and allergic rhinitis a compound of Formula Ia or Ib may be combined with other therapeutic agents such as: (1) TNF-α inhibitors such as Remicade® and Enbrel®); (2) non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

In another embodiment of the invention, the compounds of Formula Ia or Ib, or a stereoisomer, tautomer, or pharmaceutically acceptable salt or prodrug thereof, may be employed alone or in combination with other therapeutic agents for the treatment of hyperproliferative disorders (e.g., cancer) including standard chemotherapy regimens, and anti-CD20 monoclonal antibodies, rituximab, bendamustine, ofatumumab, fludarabine, lenalidomide, and/or bortezomib.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active therapeutic agents simultaneously exert their biological activities.

Kits

In one aspect, the present invention provides a kit comprising a therapeutically effective amount of at least one compounds of Formula Ia or Ib, or a pharmaceutically acceptable salt or prodrug of said compound and a pharmaceutically acceptable carrier, vehicle or diluent.

In another aspect the present invention provides a kit comprising an amount of at least one compounds of Formula Ia or Ib, or a pharmaceutically acceptable salt or prodrug of said compound and an amount of at least one additional therapeutic agent listed above, wherein the amounts of the two or more active ingredients result in a desired therapeutic effect. In one embodiment, the one or more compounds of Formula Ia or Ib and the one or more additional therapeutic agents are provided in the same container. In one embodiment, the one or more compounds of Formula Ia or Ib and the one or more additional therapeutic agents are provided in separate containers.

The present invention is not to be limited by the specific embodiments disclosed in the examples that are intended as illustrations of few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

SCHEMES AND EXAMPLES

The abbreviations used herein have the following tabulated meanings. Abbreviations not tabulated below have their meanings as commonly used unless specifically stated otherwise.

| Abbreviations Used in the Description of Compound Preparation | |
|---|---|
| Ac | acetyl |
| BINAP | (2,2'-bis(diphenylphosphino)-1,1'-binaphthyl) |
| Boc | tert-butoxycarbamate |
| DAST | (diethylamino)sulfur trifluoride |
| dba | dibenzylideneacetone |
| DCM | dichloromethane |
| DEA | diethylamine |
| DIEA, DIPEA | N,N-diisopropylethylamine |
| DMAP | dimethylaminopyridine |
| DME | 1,2 dimethoxyethane |
| DMF | dimethylformamide |
| DMSO | dimethyl sulfoxide |
| dppf | 1,1'-bis(diphenylphosphino)ferrocene |
| dtbpf | (di-tert-butylphosphino)ferrocene |
| EDC | N-(3-dimethylaminopropyl)-N'-ethylcarbodiimide hydrochloride |
| EI | electron ionization |

| Abbreviations Used in the Description of Compound Preparation | |
|---|---|
| ESI | electrospray ionization |
| EtOH | ethanol |
| EtOAc | ethyl acetate |
| GST | Glutathione S-transferase |
| h, hr | hour |
| HATU | 1-[bis(dimethylarnino)methylene]-1H-1,2,3-triazolo[4,5-b]pyridinium 3-oxid-hexafluorophosphate |
| HOBT | 1-hydroxybenzotriazole hydrate |
| HPLC | high performance liquid chromatography |
| HTRF | Homogeneous Time Resolved Fluorescence |
| IPA | 2-propanol |
| (Ir[dF(CF$_3$)ppy]$_2$(dtbpy))PF$_6$ | [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate |
| LC/MS | liquid chromatography coupled to mass spectrometer |
| mCPBA | 3-chloroperoxybenzoic acid |
| min | minute(s) |
| MeCN | acetonitrile |
| MeOH | methanol |
| MS | mass spectrum (data) |
| NMR | nuclear magnetic resonance (data) |
| (Pd$_2$(dba)$_3$.CHCl$_3$ | tris(dibenzylideneacetone)palladium-chloroform adduct |
| Pd(dppf) | [1,1'-bis(diphenylphosphino)ferrocene]dichloropalladium(II) |
| PdCl$_2$(dppf)-CH$_2$Cl$_2$ adduct | tris(dibenzylideneacetone)palladium-methylene chloride adduct |
| Pd(PPh$_3$)$_2$Cl$_2$ | bis(triphenylphosphine)palladium(II) dichloride |
| PMB | 4-methoxybenzyl |
| Pr | propyl |
| RT | room temperature |
| SFC | supercritical fluidic chromatography |
| tBuXPhos Pd G1 | Chloro[2-(di-tert-butylphosphino)-2',4',6'-triisopropyl-1,1'-biphenyl] [2-(2-aminoethyl)phenyl)]palladium(II) |
| tBu | tert-butyl |
| t-BuOH | tert-butanol |
| TBAF | tetrabutylammonium fluoride |
| TEA | triethylamine |
| TFA | trifluoroacetic acid |
| THF | tetrahydrofuran |
| Xphos Pd G2 | Chloro(2-dicyclohexylphosphino-2',4',6'-triisopropyl-1,1'-biphenyl)[2-(2'-amino-1,1'-biphenyl)]palladium(II) |

General Synthetic Schemes

The compounds of Formulas Ia and Ib may be prepared from known or readily prepared starting materials, following methods known to one skilled in the art of organic synthesis. Methods useful for making the compounds of Formulas Ia and Ib are set forth in the Examples below and generalized in Schemes 1 through 8 presented below. Alternative synthetic pathways and analogous structures will be apparent to those skilled in the art of organic synthesis.

The substituents illustrated in the following Schemes correspond to those reflected in Formulas Ia and Ib. In Schemes 1 through 8, PG represents a protecting group, such as tert-butoxycarbamate (Boc). For ease of illustration, substituent Z is shown as a piperazinyl group, however 2,5-diazabicyclo[2.2.1]hept-2-yl or 3,8-diazabicyclo[3.2.1]octyl may replace the illustrated piperazinyl.

Scheme 1

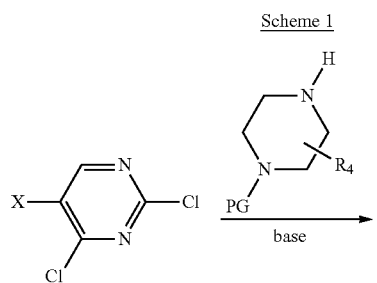

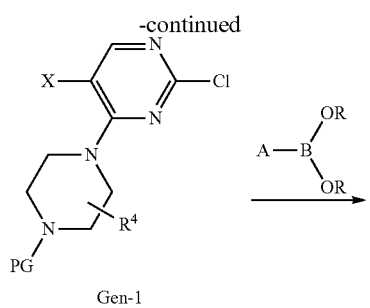

Gen-1

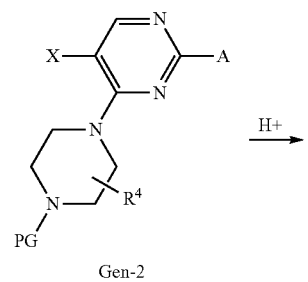

Gen-2

-continued

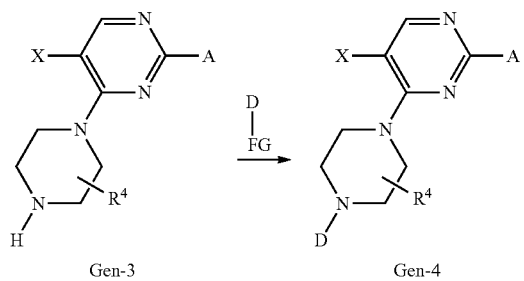

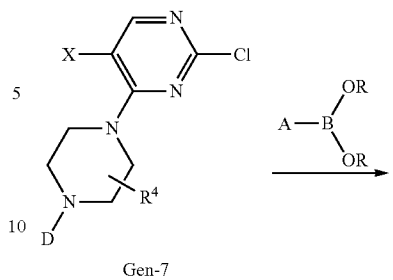

Several synthetic routes were employed in the syntheses of the compounds described herein. One such route is illustrated in Scheme 1. In this approach, a commercially-available substituted 2,4-dichloropyrimidine, such as, for example, 2,4-dichloropyrimidine-5-carbonitrile, is elaborated to Gen-1 via a nucleophilic aromatic substitution reaction using a protecting diamine with the addition of a base (for example DIEA). This substitution generally occurs at the 4-position. Gen-1 can then be elaborated to Gen-2 via a cross-coupling with an appropriately substituted boronate ester or boronic acid, for example 1-methyl-4-(4,4,5,5-tetramethyl-1,3,2-dioxaborolan-2-yl)-1H-pyrazole. The diamine is then deprotected, for example with the use of an acid like TFA to remove a Boc protecting group, to afford Gen-3. Gen-3 is then elaborated to Gen-4 by reacting the free amine with an appropriate reactive functional group, such as for example; an acid (via an amide coupling reaction), an acid chloride (via direct acylation), a sulfonyl chloride, an isocyanate, or an alkyl halide. Occasionally, when D is an aryl or heteroaryl group, Gen-3 may be engaged in a C—N cross-coupling reaction with an aryl halide under palladium-catalyzed conditions. In some cases, where A is connected to the pyrimidine ring via a C—N linkage, an amine is used in a second nucleophilic aromatic substitution reaction to form Gen-2 from Gen-1. The Gen-2 may be elaborated to the final Gen-4 as described above.

In another approach shown in Scheme 2, a commercially-available protected diamine, such as tert-butyl (1S,4S)-2,5-diazabicyclo[2.2.1]heptane-2-carboxylate, is elaborated to Gen-5 by reacting the free amine with an appropriate reactive functional group, such as, for example; an acid (via an amide coupling reaction), an acid chloride (via direct acylation), a sulfonyl chloride, an isocyanate, or an alkyl halide. Occasionally, when D is an aryl or heteroaryl group, the amine may be engaged in a C—N cross-coupling reaction with an aryl halide under palladium-catalyzed conditions. Gen-5 is then deprotected to free-amine Gen-6 using standard conditions (for example, acidic conditions to remove a Boc group). Gen-6 then can undergo a nucleophilic aromatic substitution reaction, via the addition of base, with a substituted 2,4-dichloropyrimidine to afford Gen-7. Gen-7 is then elaborated to Gen-4 via a cross-coupling with an appropriately-substituted boronate ester or boronic acid, such as, for example, 1-methyl-4-(4,4,5,5-tetramethyl-1,3,2-dioxaborolan-2-yl)-1H-pyrazole.

Scheme 2

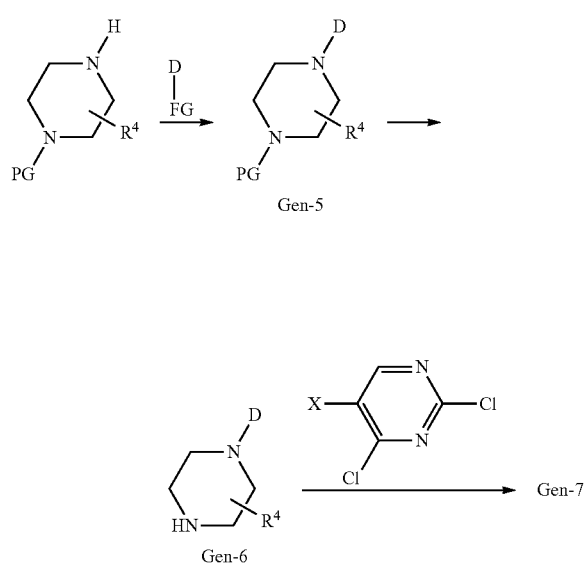

Scheme 3

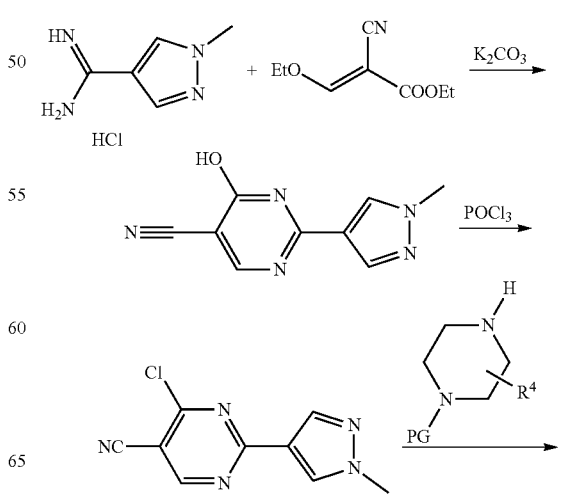

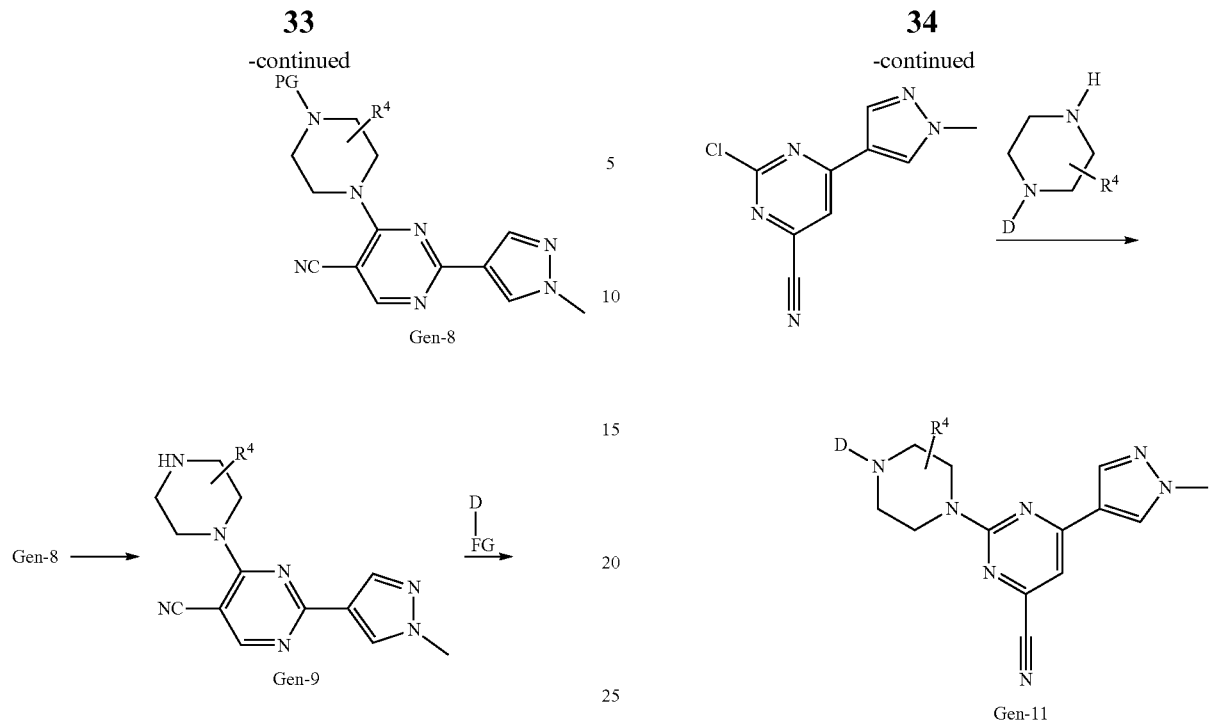

In another approach, the pyrimidine ring is formed with the A group already in place. For example, 1-methyl-1H-pyrazole-4-carboximidamide is condensed with ethyl (E)-2-cyano-3-ethoxyacrylate to afford 4-hydroxy-2-(1-methyl-H-pyrazol-4-yl)pyrimidine-5-carbonitrile under basic conditions, which is then converted to 4-chloro-2-(1-methyl-1H-pyrazol-4-yl)pyrimidine-5-carbonitrile with phosphorus oxychloride. A protected diamine is then added to afford Gen-8 under basic conditions, which is then depotected and functionlized with substitution of D as described in Scheme 1 above to afford Gen-10.

In another approach, 2,6-dichloropyrimidine-4-carbonitrile can be converted to 2-chloro-6-(1-methyl-1H-pyrazol-4-yl)pyrimidine-4-carbonitrile via a palladium-catalyzed cross-coupling reaction with 1-methyl-4-(4,4,5,5-tetramethyl-1,3,2-dioxaborolan-2-yl)-1H-pyrazole. This compound is then converted to Gen-11 via the addition of a diamine via a nucleophilic aromatic substitution reaction using a protecting diamine and with the addition of a base (for example DIEA).

Scheme 5

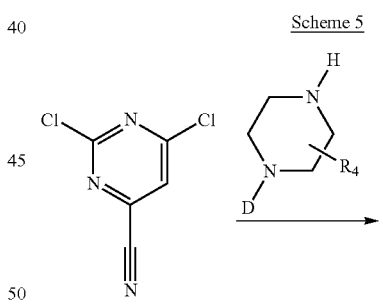

Scheme 4

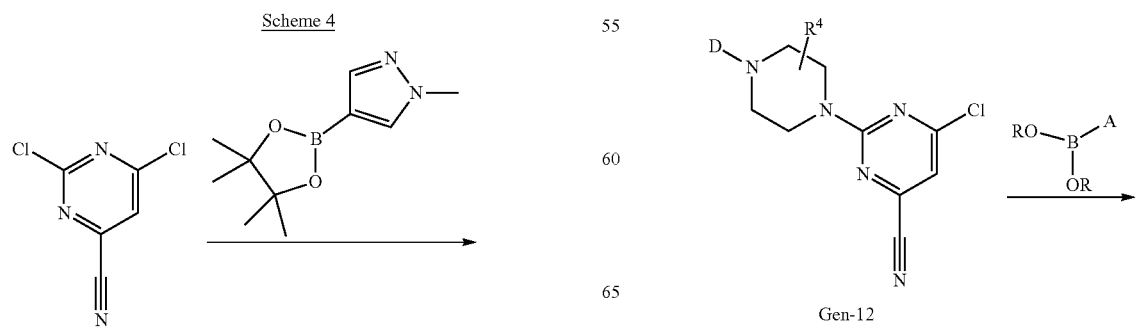

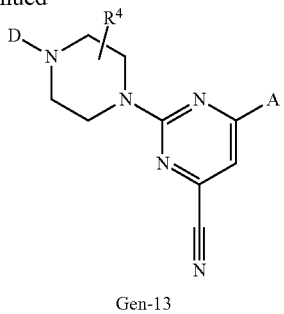

Gen-13

In a similar approach to that shown in Scheme 4, the order of steps may be reversed from the procedure described above and 2,6-dichloropyrimidine-4-carbonitrile may be converted to Gen-12 via a nucleophilic aromatic substitution reaction using a substituted diamine and with the addition of a base (for example DIEA). Gen-12 could then be converted to Gen-13 via a palladium catalyzed cross-coupling of a boronate ester or boronic acid (for example 1-methyl-4-(4,4,5,5-tetramethyl-1,3,2-dioxaborolan-2-yl)-1H-pyrazole).

Scheme 6 illustrates another approach, where 2,6-dichloro-4-iodopyrimidine is converted to Gen-14 via a cross-coupling reaction (for example, a Sonagashira reaction, Schilz, M. et al. "A Guide to Sonogashira Cross-Coupling Reactions: The Influence of Substituents in Aryl Bromides, Acetylenes, and Phosphines"; J. Org. Chem., 2012, 77 (6), pp 2798-2807) with a substituted terminal alkyne. Gen-14 is then elaborated to Gen-15 via a palladium-catalyzed cross-coupling reaction with 1-methyl-4-(4,4,5,5-tetramethyl-1,3,2-dioxaborolan-2-yl)-1H-pyrazole. Gen-15 could then engage with a substituted diamine in a nucleophilic aromatic substitution reaction as described above to afford Gen-16.

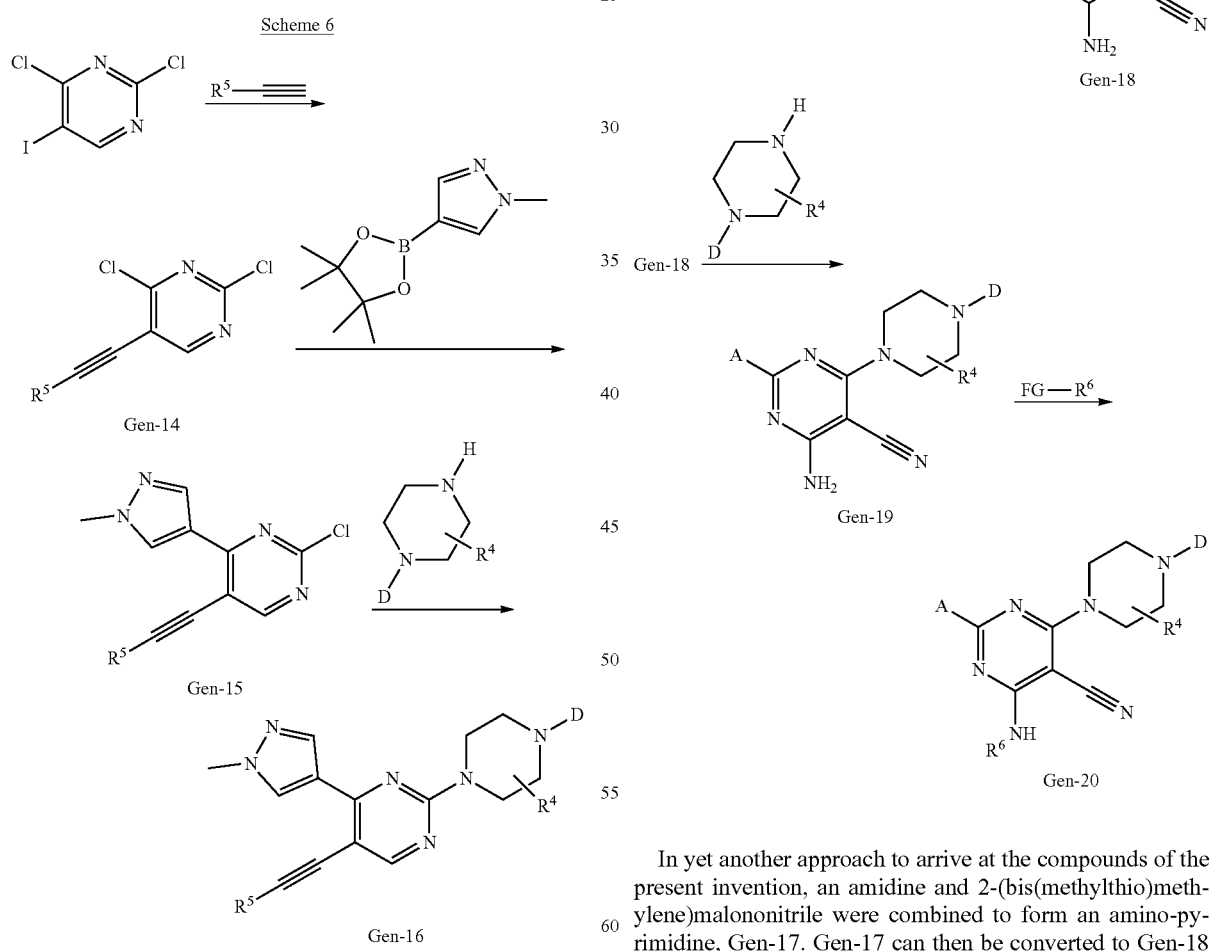

In yet another approach to arrive at the compounds of the present invention, an amidine and 2-(bis(methylthio)methylene)malononitrile were combined to form an amino-pyrimidine, Gen-17. Gen-17 can then be converted to Gen-18 via a standard oxidation reaction, after which the sulfone may be displaced in a nucleophilic aromatic substitution reaction with a substituted diamine and an appropriate base (for example DIEA) to afford Gen-19. The free amine can then be functionalized via a variety of reactions with appropriately substituted electrophiles such as, for example, isocyanates (to form ureas), alkyl halides (to form secondary amines), or acid chlorides (to form amides) under standard conditions.

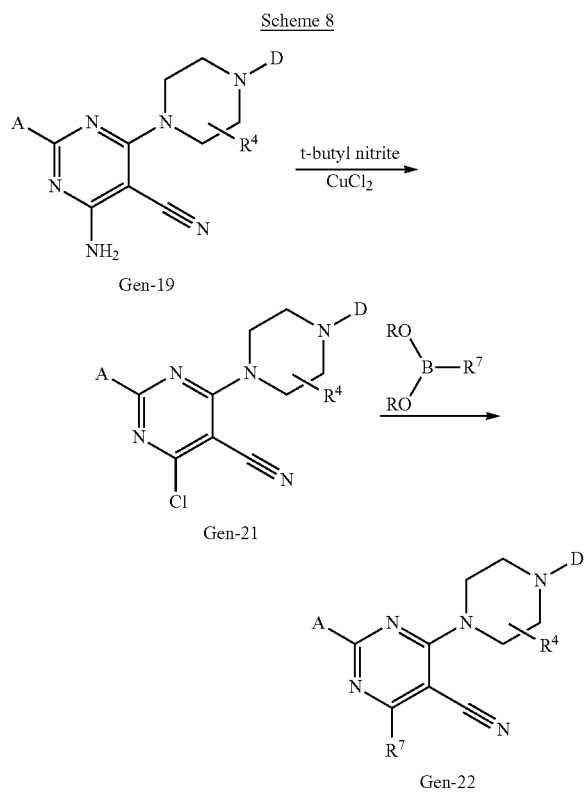

In a related approach to realizing the compounds of the current invention, Gen-19 may be converted to the aryl chloride Gen-21 through the use of t-butyl nitrite and copper chloride. Gen-21 may then be converted to Gen-22 via a palladium-catalyzed cross-coupling reaction with boronic ester or boronic acid (for example 2-ethyl-4,4,5,5-tetramethyl-1,3,2-dioxaborolane).

Compound Examples for Table 1

Example 1

4-((1S,4S)-5-(3-cyanophenyl)-2,5-diazabicyclo[2.2.1]heptan-2-yl)-2-(1-methyl-1H-pyrazol-4-yl)pyrimidine-5-carbonitrile (1-1)

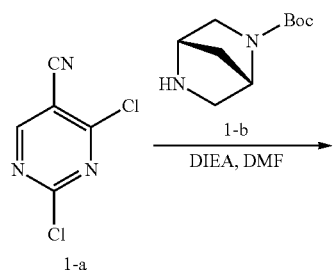

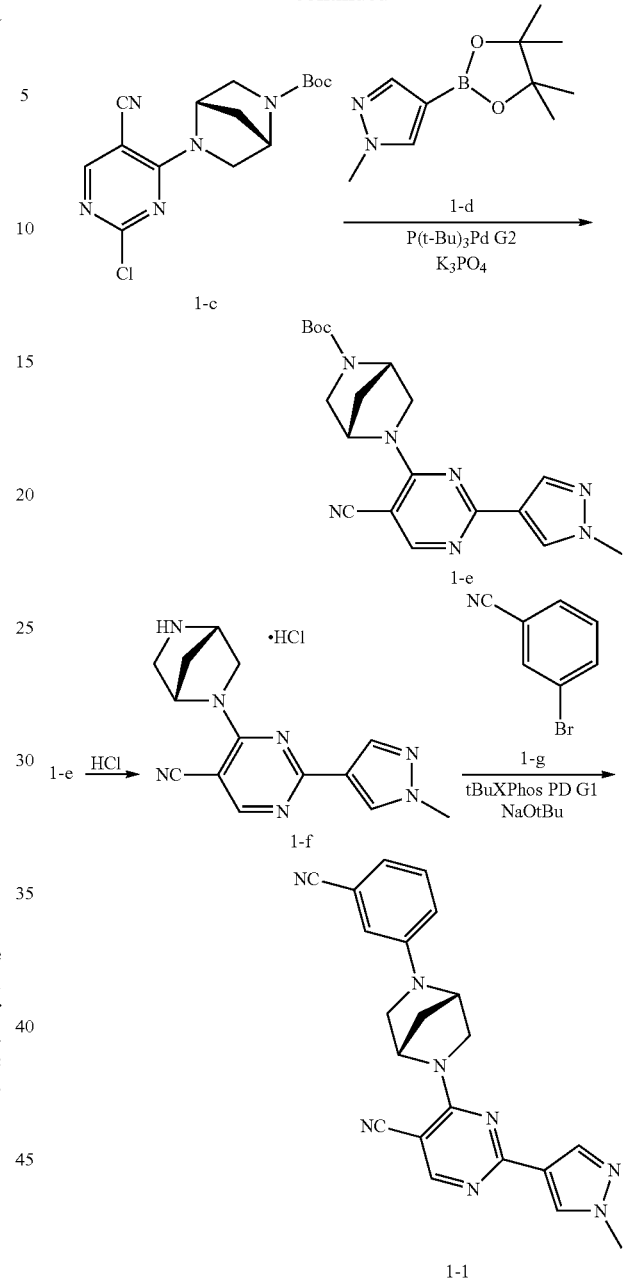

Step 1 tert-butyl (1S,4S)-5-(2-chloro-5-cyanopyrimidin-4-yl)-2,5-diazabicyclo[2.2.1]heptane-2-carboxylate (1-c)

To a flask were added (S,4S)-tert-butyl 2,5-diazabicyclo[2.2.1]heptane-2-carboxylate (3.0 g, 15.13 mmol) (1-b), 2,4-dichloropyrimidine-5-carbonitrile (3.30 g, 18.97 mmol, commercially available from Ark Pharm, Inc., Libertyville, Ill., USA) (1-a), DMF (100 ml) and DIPEA (8 ml, 45.8 mmol). The mixture was stirred at RT for 2 h, after which the solvent was removed in vacuo. The residue was dissolved into DCM and purified by column chromatography (silica gel, eluting with DCM) to afford tert-butyl (1S,4S)-5-(2-chloro-5-cyanopyrimidin-4-yl)-2,5-diazabicyclo[2.2.]heptane-2-carboxylate (1-c). MS (ESI) Calc'd for $C_{15}H_{19}ClN_5O_2$ [M+H]$^+$, 336; found, 336.

Step 2 tert-butyl (1S,4S)-5-(5-cyano-2-(1-methyl-1H-pyrazol-4-yl)pyrimidin-4-yl)-2,5-diazabicyclo[2.2.1]heptane-2-carboxylate (1-e)

To a flask were added (S,4S)-tert-butyl 5-(2-chloro-5-cyanopyrimidin-4-yl)-2,5-diazabicyclo[2.2.1]heptane-2-carboxylate (1.23 g, 3.66 mmol) (1-c), 1-methyl-4-(4,4,5,5-tetramethyl-1,3,2-dioxaborolan-2-yl)-1H-pyrazole (1.143 g, 5.49 mmol) (1-d) and chloro[(tri-tert-butylphosphine)-2-(2-aminobiphenyl)]palladium(II) (P(t-Bu)3Pd G2) (0.188 g, 0.366 mmol). This mixture was evacuated and backfilled with N$_2$ (3 times). Degassed THF (25 ml) and K$_3$PO$_4$ (tripotassium phosphate) (8 ml, 8.00 mmol, 1M) were then added to this flask, and the resulting mixture was heated to 60° C. for 18 h. The solution was then cooled and water was added, and the organic phase was separated and concentrated in vacuo. The resulting residue was purified by chromatography (silica gel, eluting with a gradient of 0-100% EtOAc in hexanes) to afford tert-butyl (1S,4S)-5-(5-cyano-2-(1-methyl-1H-pyrazol-4-yl)pyrimidin-4-yl)-2,5-diazabicyclo[2.2.1]heptane-2-carboxylate (1-e). MS (ESI) Calc'd for $C_{19}H_{24}N_7O_2$ [M+1]$^+$, 382; found, 382.

Step 3 4-((1S,4S)-2,5-diazabicyclo[2.2.1]heptan-2-yl)-2-(1-methyl-H-pyrazol-4-yl)pyrimidine-5-carbonitrile (1-f)

To a flask containing tert-butyl (1S,4S)-5-(5-cyano-2-(1-methyl-H-pyrazol-4-yl)pyrimidin-4-yl)-2,5-diazabicyclo[2.2.1]heptane-2-carboxylate (2.1 g, 5.51 mmol)(1-e) were added dioxane (55 ml) and HCl (15 ml, 60.0 mmol, 4M in dioxane). The reaction mixture was stirred at RT for 20 h. The mixture was then concentrated to afford 4-((1S,4S)-2,5-diazabicyclo[2.2.1]heptan-2-yl)-2-(1-methyl-1H-pyrazol-4-yl)pyrimidine-5-carbonitrile as the HCl salt (1-f). MS (ESI) Calc'd for $C_{14}H_{16}N_7$ [M+1]$^+$, 282; found, 282.

Step 4 4-((1S,4S)-5-(3-cyanophenyl)-2,5-diazabicyclo[2.2.1]heptan-2-yl)-2-(1-methyl-1H-pyrazol-4-yl)pyrimidine-5-carbonitrile (1-1)

To the vial were added 3-bromobenzonitrile (1-g) (21.95 mg, 0.103 mmol), compound (1-f) (22 mg, 0.052 mmol), tBuXPhos Pd G1 (5.31 mg, 7.73 µmol), NaOtBu (29.7 mg, 0.309 mmol) and THF (350 µl). The mixture was evacuated and back filled with N$_2$ for a total of 3 times and heated at 90° C. for 16 h. After cooling down, metal scavenger, QuandraPure® TU (Sigma Aldrich, St. Louis, Mo., USA) were added to the mixture and stirred for 3 h. The mixture was filtered and purified on reversed phase HPLC (ACN/water, 0.1% TFA) to afford 4-((1S,4S)-5-(3-cyanophenyl)-2,5-diazabicyclo[2.2.1]heptan-2-yl)-2-(1-methyl-1H-pyrazol-4-yl)pyrimidine-5-carbonitrile (1-1) as a TFA salt. $^1$H NMR (500 MHz, DMSO-d$_6$) δ 8.55 (s, 1H), 8.38 (s, 1H), 8.01 (s, 1H), 7.31 (t, J=7.9 Hz, 1H), 7.07 (s, 1H), 6.97 (dd, J=15.4, 8.0 Hz, 2H), 4.10-3.85 (m, 3H), 3.88 (s, 3H), 3.75-3.56 (m, 3H), 2.50-2.45 (m, 2H). MS (ESI) Calc'd for $C_{21}H_{19}N_8$ [M+1]$^+$, 383; found, 383.

Example 2

4-[(1R,4S)-5-(3-fluorophenyl)-2,5-diazabicyclo[2.2.1]hept-2-yl]-2-pyrazolo[1,5-a]pyridin-3-ylpyrimidine-5-carbonitrile (1-2)

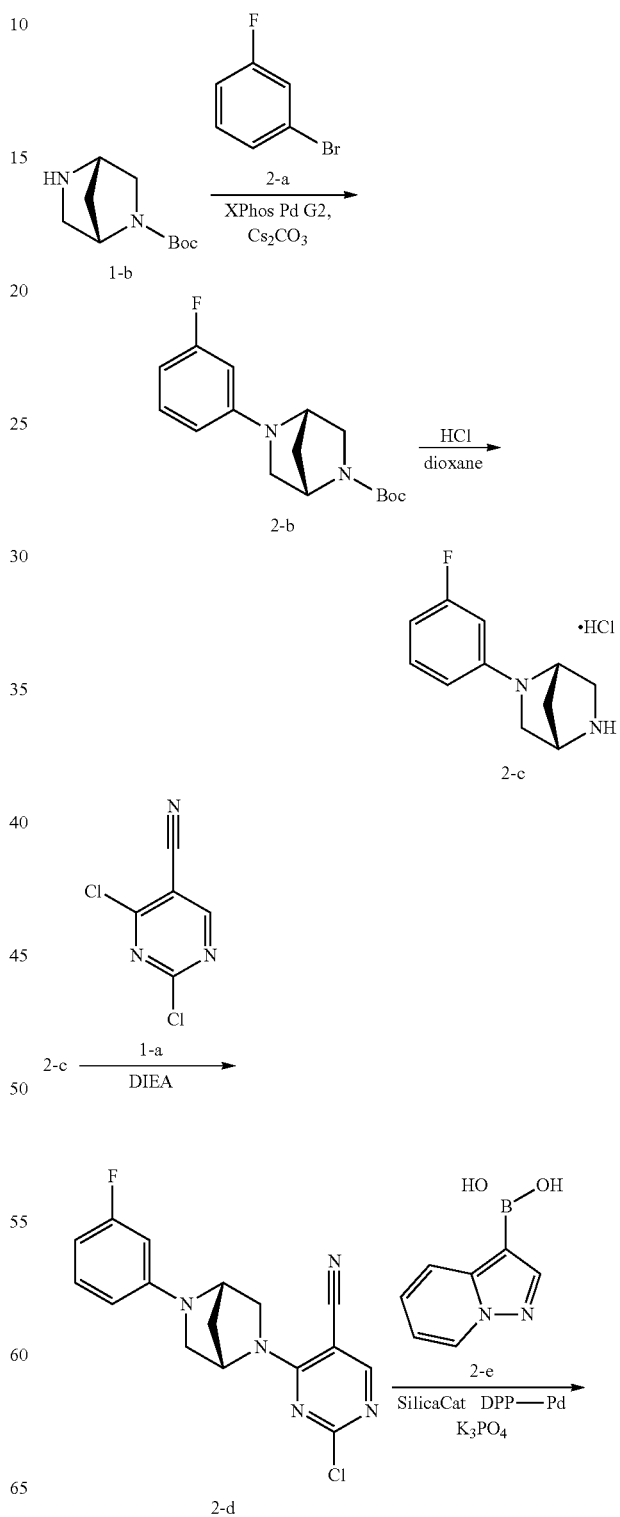

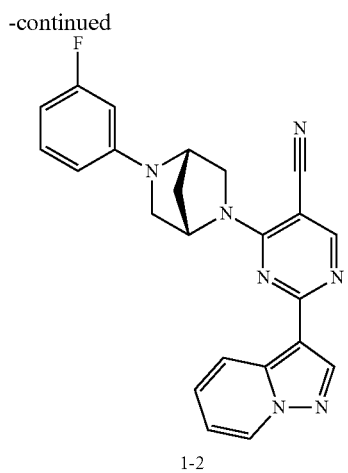

1-2

Step 1 (1S,4S)-tert-butyl 5-(3-fluorophenyl)-2,5-diazabicyclo[2.2.1]heptane-2-carboxylate (2-b)

To a sealed pressure vessel was added XPhos Pd G2 (0.36 g, 0.45 mmol), (1S,4S)-tert-butyl 2,5-diazabicyclo[2.2.1]heptane-2-carboxylate (1-b) (1.8 g, 9.1 mmol), cesium carbonate ($Cs_2CO_3$) (8.9 g, 27 mmol), dioxane (60 mL) and 1-bromo-3-fluorobenzene (2-a) (2.0 g, 11 mmol). The reaction vessel was sparged with $N_2$, sealed and warmed to 90° C. for 8 hours. The completed reaction was diluted with 50 mL EtOAc and was passed over a Celite® filter cake prepared in a fritted glass funnel. The Celite® cake was washed with an additional portion of EtOAc and the collected organics were concentrated in vacuo to afford (S,4S)-tert-butyl 5-(3-fluorophenyl)-2,5-diazabicyclo[2.2.1]heptane-2-carboxylate (2-b) as a crude residue. MS ESI calc'd. for $C_{16}H_{21}FN_2O_2$ [M+H]$^+$ 293, found 293.

Step 2 (1S,4S)-2-(3-fluorophenyl)-2,5-diazabicyclo[2.2.1]heptane, HCl (2-c)

To round bottom flask containing the crude residue of (1S,4S)-tert-butyl 5-(3-fluorophenyl)-2,5-diazabicyclo[2.2.1]heptane-2-carboxylate (2-b) (2.7 g, 9.0 mmol) suspended in Dioxane (20 mL) was added HCl in Dioxane (30 mL, 120 mmol, 4.0 M). The reaction was allowed to stir at RT for 4 hours. The completed reaction was concentrated in vacuo to afford (1S,4S)-2-(3-fluorophenyl)-2,5-diazabicyclo[2.2.1]heptane as a crude HCl salt (2-c) which was used without further purification. MS ESI calc'd. for $C_{11}H_{13}FN_2$ [M+H]$^+$ 193, found 193.

Step 3 2-chloro-4-((1S,4S)-5-(3-fluorophenyl)-2,5-diazabicyclo[2.2.1]heptan-2-yl)pyrimidine-5-carbonitrile (2-d)

To round bottom flask containing (1S,4S)-2-(3-fluorophenyl)-2,5-diazabicyclo[2.2.1]heptane, HCl (2-c)(2.07 g, 9.05 mmol) taken up in 1,4-Dioxane (90 mL, 0.1 M) was added 2,4-dichloropyrimidine-5-carbonitrile (1-a)(1.65 g, 9.50 mmol) and DIEA (4.74 ml, 27.2 mmol). The reaction was allowed to stir at RT for 4 hours. The completed reaction was diluted with EtOAc and was washed with water. The reaction mixture was then partitioned in a separatory funnel and the organics were collected and dried over magnesium sulfate. The organics were filtered and concentrated onto silica gel. The resulting adsorbed crude reaction mixture was purified via column chromatography (silica gel, eluting EtOAc:Hexanes (0-100%)) to afford 2-chloro-4-((1S,4S)-5-(3-fluorophenyl)-2,5-diazabicyclo[2.2.1]heptan-2-yl)pyrimidine-5-carbonitrile (2-d). MS ESI calc'd. for $C_{16}H_{13}ClFN_5$ [M+H]$^+$ 330, found 330.

Step 4 4-[(1R,4S)-5-(3-fluorophenyl)-2,5-diazabicyclo[2.2.1]hept-2-yl]-2-pyrazolo[1,5-a]pyridin-3-ylpyrimidine-5-carbonitrile (1-2)

To a microwave reaction vessel was added 2-chloro-4-((1S,4S)-5-(3-fluorophenyl)-2,5-diazabicyclo[2.2.1]heptan-2-yl)pyrimidine-5-carbonitrile (2-d) (0.020 g, 0.061 mmol), pyrazolo[1,5-a]pyridin-3-ylboronic acid (2-e)(0.010 g, 0.061 mmol), potassium phosphate tribasic (0.039 g, 0.18 mmol), SilicaCat® DPP-Pd (SiliCycle, Inc., Quebec City, Canada)(0.047 g, 0.012 mmol, 0.26 mmol/g), followed by dioxane:water (3:1 v/v, 0.047 M total reaction concentration). The reaction was sealed and irradiated in the microwave for 30 minutes at 160° C. The completed reaction was diluted with water and extracted with DCM (4.0 mL) and was partitioned with an Isolute® SPE phase separator cartridge (Biotage®, Charlotte, N.C., USA). The collected organics were concentrated in vacuo using a Genevac HT4 evaporator (Genevac Ltd, Ipswich, Suffolk UK), the crude residues were taken up in DMSO (1.0 mL), were passed through a syringe filter and the filtrate was purified by reverse phase preparative HPLC (5:95 to 95:5 acetonitrile:water: 0.1% v/v TFA modifier) to afford compound 1-2 as the TFA salt. $^1$H NMR (500 MHz, DMSO-d$_6$): δ 8.83 (d, J=6.5 Hz, 1H), 8.73-8.63 (m, 1H), 8.59 (s, 1H), 8.46-8.31 (m, 1H), 7.59-7.49 (m, 1H), 7.15-7.04 (m, 2H), 6.52-6.39 (m, 2H), 6.39-6.25 (m, 1H), 5.44 (s, 1H), 4.74 (s, 1H), 4.04-3.88 (m, 1H), 3.70 (d, J=9.3 Hz, 2H), 2.10 (s, 2H), 1.20 (s, 1H). MS ESI calc'd. for $C_{23}H_{18}FN_7$ [M+H]$^+$ 412, found 412.

Example 3

2-(4,6-dihydropyrrolo[3,4-c]pyrazol-5(1H)-yl)-4-[(1S,4R)-5-(3-fluorophenyl)-2,5-diazabicyclo[2.2.1]hept-2-yl]pyrimidine-5-carbonitrile (1-3)

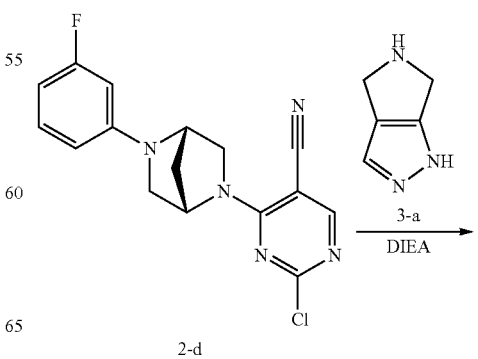

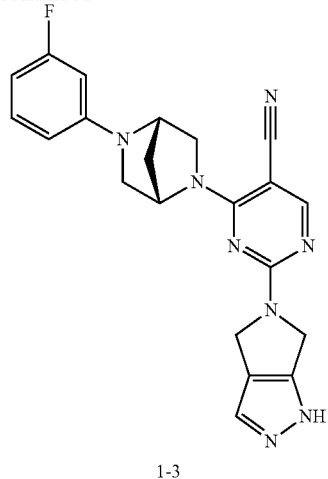

1-3

To a sealed tube reaction vessel was added 2-chloro-4-((1S,4S)-5-(3-fluorophenyl)-2,5-diazabicyclo[2.2.1]heptan-2-yl)pyrimidine-5-carbonitrile (2-d) (0.020 g, 0.061 mmol), 1,4,5,6-tetrahydropyrrolo[3,4-c]pyrazole (3-a) (0.013 g, 0.12 mmol), DMA (dimethylacetamide) (1.0 mL, 0.06 M), and DIEA (0.050 mL, 0.29 mmol). The reaction was sealed and warmed to 75° C. for 8 hours. The completed reaction was passed through a syringe filter and the filtrate was purified by reverse phase preparative HPLC (5:95 to 95:5 acetonitrile:water: 0.1% v/v TFA modifier) to afford compound 1-3 as the TFA salt. $^1$H NMR (500 MHz, DMSO-$d_6$): 1H NMR (500 MHz, DMSO-d6) δ 12.70 (d, J=10.1 Hz, 1H), 8.29 (d, J=2.5 Hz, 1H), 7.55 (s, 1H), 7.11 (q, J=8.1 Hz, 1H), 6.48-6.38 (m, 2H), 6.38-6.30 (m, 1H), 5.23 (s, 1H), 4.67 (s, 1H), 4.53 (s, 4H), 3.84 (s, 1H), 3.65-3.50 (m, 2H), 2.02 (s, 2H), 1.27-1.15 (m, 1H). MS ESI calc'd. for $C_{21}H_{19}FN_8$ [M+H]$^+$ 403, found 403.

Compounds 1-4 through 1-6 and 1-8 through 1-15 found in Table 1 were prepared in a similar manner to Example 1, using the corresponding aryl bromides in step 4 of Example 1.

Compounds 1-7 and 1-16 through 1-21 found in Table 1 were prepared in a similar manner to Example 2, using the corresponding boronic acids or boronic esters in step 4.

Compounds 1-22 through 1-23 found in Table 1 were prepared in a similar manner to Example 3, using the corresponding amines.

TABLE 1

| Compound | Structure | Name | Exact Mass [M + H]+ |
|---|---|---|---|
| 1-1 | 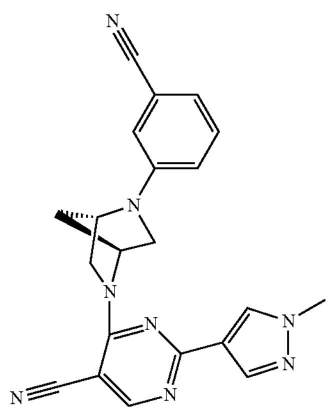 [SMILES: Cn1cc(-c2ncc(C#N)c(N3C[C@@H]4C[C@H]3CN4c3cccc(C#N)c3)n2)cn1] | 4-[(1S,4R)-5-(3-cyanophenyl)-2,5-diazabicyclo[2.2.1]hept-2-yl]-2-(1-methyl-1H-pyrazol-4-yl)pyrimidine-5-carbonitrile | Calc'd 383, found |
| 1-2 | 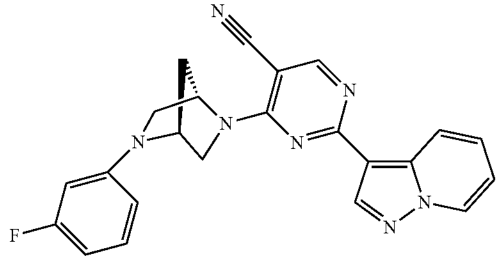 [SMILES: N#Cc1cnc(-c2cnn3ccccc23)nc1N1C[C@@H]2C[C@H]1CN2c1cccc(F)c1] | 4-[(1R,4S)-5-(3-fluorophenyl)-2,5-diazabicyclo[2.2.1]hept-2-yl]-2-pyrazolo[1,5-a]pyridin-3-ylpyrimidine-5-carbonitrile | Calc'd 412, found |

TABLE 1-continued

| Compound | Structure | Name | Exact Mass [M + H]+ |
|---|---|---|---|
| 1-3 | 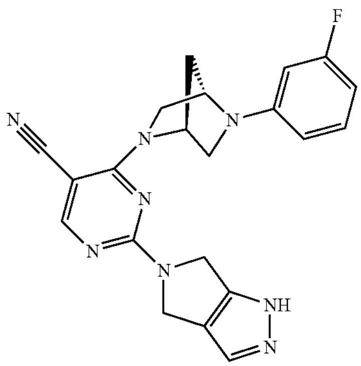 [SMILES: N#Cc1cnc(N2Cc3cn[nH]c3C2)nc1N1C[C@@H]2C[C@H]1CN2c1cccc(F)c1] | 2-(4,6-dihydropyrrolo[3,4-c]pyrazol-5(1H)-yl)-4-[(1S,4R)-5-(3-fluorophenyl)-2,5-diazabicyclo[2.2.1]hept-2-yl]pyrimidine-5-carbonitrile | Calc'd 403, found |
| 1-4 | 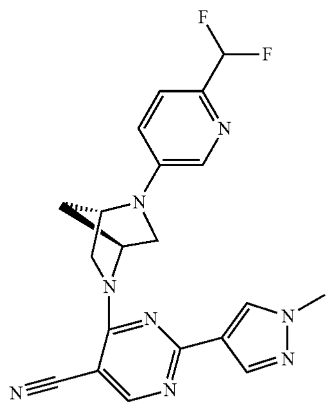 [SMILES: Cn1cc(-c2ncc(C#N)c(N3C[C@@H]4C[C@H]3CN4c3ccc(C(F)F)nc3)n2)cn1] | 4-{(1S,4R)-5-[6-(difluoromethyl)pyridin-3-yl]-2,5-diazabicyclo[2.2.1]hept-2-yl}-2-(1-methyl-1H-pyrazol-4-yl)pyrimidine-5-carbonitrile | Calc'd 409, found |
| 1-5 | 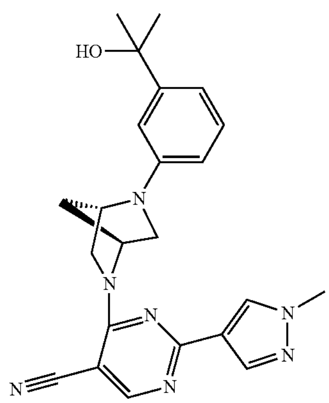 [SMILES: Cn1cc(-c2ncc(C#N)c(N3C[C@@H]4C[C@H]3CN4c3cccc(C(C)(C)O)c3)n2)cn1] | 4-{(1S,4R)-5-[3-(1-hydroxy-1-methylethyl)phenyl]-2,5-diazabicyclo[2.2.1]hept-2-yl}-2-(1-methyl-1H-pyrazol-4-yl)pyrimidine-5-carbonitrile | Calc'd 416, found |
| 1-6 | 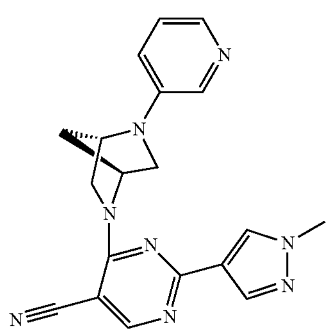 [SMILES: Cn1cc(-c2ncc(C#N)c(N3C[C@@H]4C[C@H]3CN4c3cccnc3)n2)cn1] | 2-(1-methyl-1H-pyrazol-4-yl)-4-[(1S,4R)-5-pyridin-3-yl-2,5-diazabicyclo[2.2.1]hept-2-yl]pyrimidine-5-carbonitrile | Calc'd 359, found |

TABLE 1-continued

| Compound | Structure | Name | Exact Mass [M + H]+ |
|---|---|---|---|
| 1-7 | 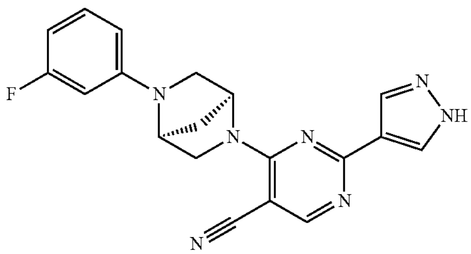 [SMILES: N#Cc1cnc(-c2cn[nH]c2)nc1N1C[C@@H]2C[C@H]1CN2c1cccc(F)c1] | 4-[(1S,4S)-5-(3-fluorophenyl)-2,5-diazabicyclo[2.2.1]hept-2-yl]-2-(1H-pyrazol-4-yl)pyrimidine-5-carbonitrile | Calc'd 362, found |
| 1-8 | 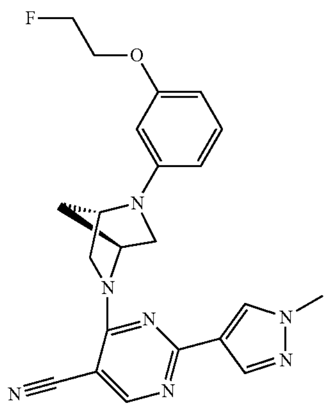 [SMILES: Cn1cc(-c2ncc(C#N)c(N3C[C@@H]4C[C@H]3CN4c3cccc(OCCF)c3)n2)cn1] | 4-{(1S,4R)-5-[3-(2-fluoroethoxy)phenyl]-2,5-diazabicyclo[2.2.1]hept-2-yl}-2-(1-methyl-1H-pyrazol-4-yl)pyrimidine-5-carbonitrile | Calc'd 420, found |
| 1-9 | 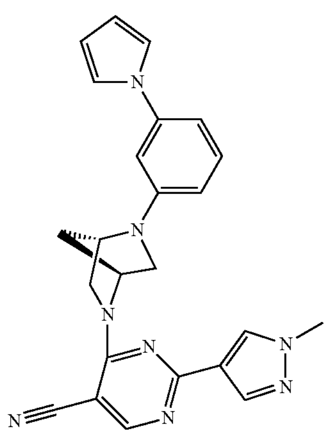 [SMILES: Cn1cc(-c2ncc(C#N)c(N3C[C@@H]4C[C@H]3CN4c3cccc(-n4cccc4)c3)n2)cn1] | 2-(1-methyl-1H-pyrazol-4-yl)-4-{(1S,4R)-5-[3-(1H-pyrrol-1-yl)phenyl]-2,5-diazabicyclo[2.2.1]hept-2-yl}pyrimidine-5-carbonitrile | Calc'd 423, found |
| 1-10 | 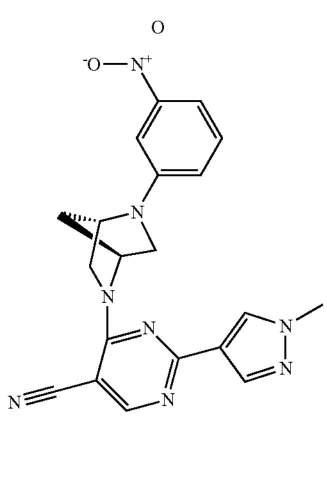 | 2-(1-methyl-1H-pyrazol-4-yl)-4-[(1S,4R)-5-(3-nitrophenyl)-2,5-diazabicyclo[2.2.1]hept-2-yl]pyrimidine-5-carbonitrile | Calc'd 403, found |

TABLE 1-continued

| Compound | Structure | Name | Exact Mass [M + H]+ |
|---|---|---|---|
| 1-11 | 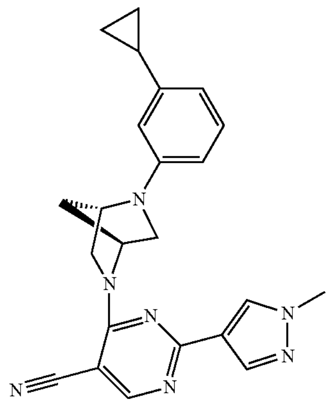 [SMILES: Cn1cc(-c2ncc(C#N)c(N3C[C@@H]4C[C@H]3CN4c3cccc(C4CC4)c3)n2)cn1] | 4-[(1S,4R)-5-(3-cyclopropylphenyl)-2,5-diazabicyclo[2.2.1]hept-2-yl]-2-(1-methyl-1H-pyrazol-4-yl)pyrimidine-5-carbonitrile | Calc'd 398, found |
| 1-12 | 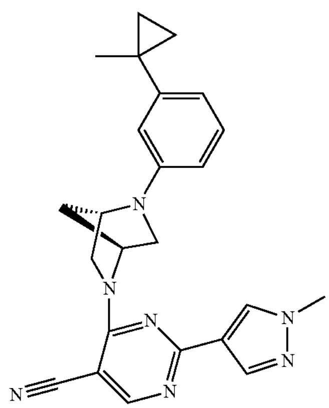 [SMILES: Cn1cc(-c2ncc(C#N)c(N3C[C@@H]4C[C@H]3CN4c3cccc(C4(C)CC4)c3)n2)cn1] | 4-{(1S,4R)-5-[3-(1-methylcyclopropyl)phenyl]-2,5-diazabicyclo[2.2.1]hept-2-yl}-2-(1-methyl-1H-pyrazol-4-yl)pyrimidine-5-carbonitrile | Calc'd 412, found |
| 1-13 | 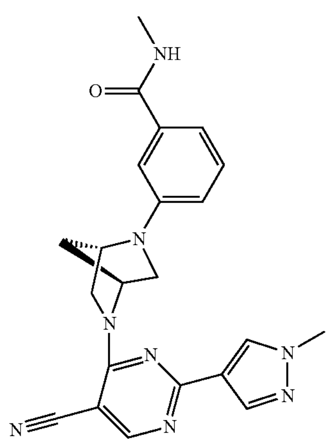 [SMILES: CNC(=O)c1cccc(N2C[C@@H]3C[C@H]2CN3c2nc(-c3cnn(C)c3)ncc2C#N)c1] | 3-{(1R,4S)-5-[5-cyano-2-(1-methyl-1H-pyrazol-4-yl)pyrimidin-4-yl]-2,5-diazabicyclo[2.2.1]hept-2-yl}-N-methylbenzamide | Calc'd 415, found |

TABLE 1-continued

| Compound | Structure | Name | Exact Mass [M + H]+ |
|---|---|---|---|
| 1-14 | 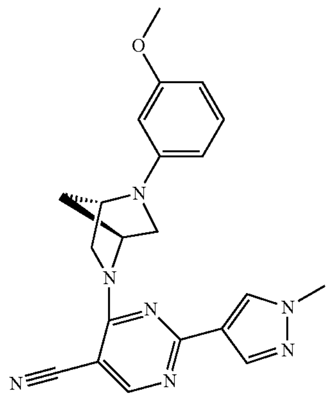 [SMILES: COc1cccc(N2C[C@@H]3C[C@H]2CN3c2nc(-c3cnn(C)c3)ncc2C#N)c1] | 4-[(1S,4R)-5-(3-methoxyphenyl)-2,5-diazabicyclo[2.2.1]hept-2-yl]-2-(1-methyl-1H-pyrazol-4-yl)pyrimidine-5-carbonitrile | Calc'd 388, found |
| 1-15 | 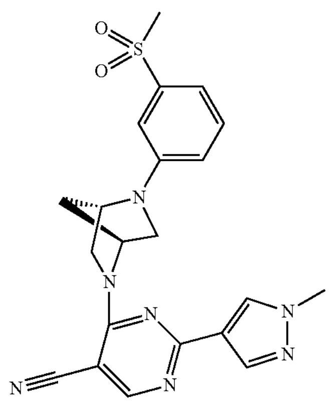 [SMILES: Cn1cc(-c2ncc(C#N)c(N3C[C@@H]4C[C@H]3CN4c3cccc(S(C)(=O)=O)c3)n2)cn1] | 2-(1-methyl-1H-pyrazol-4-yl)-4-{(1S,4R)-5-[3-(methylsulfonyl)phenyl]-2,5-diazabicyclo[2.2.1]hept-2-yl}pyrimidine-5-carbonitrile | Calc'd 436, found |
| 1-16 | 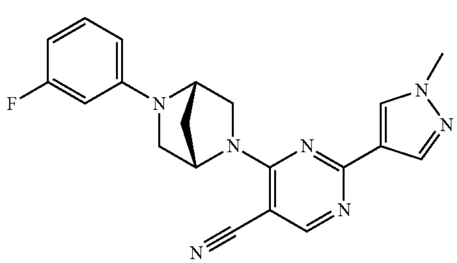 [SMILES: Cn1cc(-c2ncc(C#N)c(N3C[C@@H]4C[C@H]3CN4c3cccc(F)c3)n2)cn1] | 4-[(1S,4S)-5-(3-fluorophenyl)-2,5-diazabicyclo[2.2.1]hept-2-yl]-2-(1-methyl-1H-pyrazol-4-yl)pyrimidine-5-carbonitrile | Calc'd 376, found |
| 1-17 | 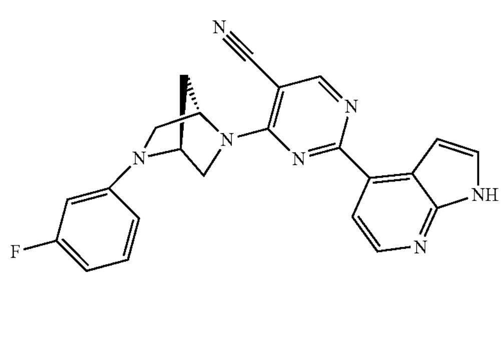 [SMILES: N#Cc1cnc(-c2ccnc3[nH]ccc23)nc1N1C[C@@H]2C[C@H]1CN2c1cccc(F)c1] | 4-[(1R,4S)-5-(3-fluorophenyl)-2,5-diazabicyclo[2.2.1]hept-2-yl]-2-(1H-pyrrolo[2,3-b]pyridin-4-yl)pyrimidine-5-carbonitrile | Calc'd 412, found |

TABLE 1-continued

| Compound | Structure | Name | Exact Mass [M + H]+ |
|---|---|---|---|
| 1-18 | 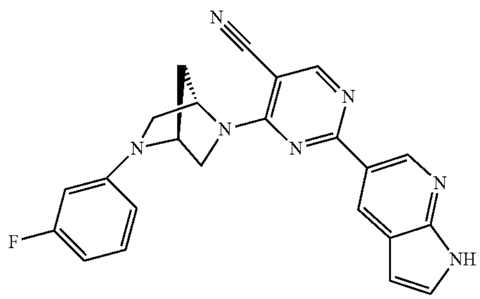 [SMILES: N#Cc1cnc(-c2cnc3[nH]ccc3c2)nc1N1C[C@@H]2C[C@H]1CN2c1cccc(F)c1] | 4-[(1R,4S)-5-(3-fluorophenyl)-2,5-diazabicyclo[2.2.1]hept-2-yl]-2-(1H-pyrrolo[2,3-b]pyridin-5-yl)pyrimidine-5-carbonitrile | Calc'd 412, found |
| 1-19 | 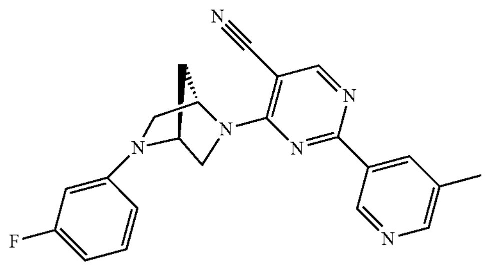 [SMILES: Cc1cncc(-c2ncc(C#N)c(N3C[C@@H]4C[C@H]3CN4c3cccc(F)c3)n2)c1] | 4-[(1R,4S)-5-(3-fluorophenyl)-2,5-diazabicyclo[2.2.1]hept-2-yl]-2-(5-methylpyridin-3-yl)pyrimidine-5-carbonitrile | Calc'd 387, found |
| 1-20 | 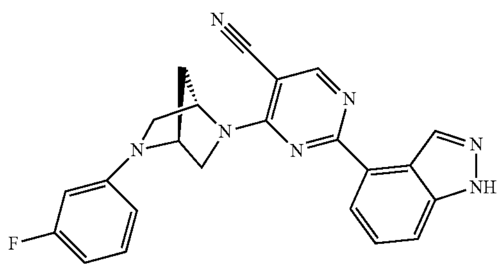 [SMILES: N#Cc1cnc(-c2cccc3[nH]ncc23)nc1N1C[C@@H]2C[C@H]1CN2c1cccc(F)c1] | 4-[(1R,4S)-5-(3-fluorophenyl)-2,5-diazabicyclo[2.2.1]hept-2-yl]-2-(1H-indazol-4-yl)pyrimidine-5-carbonitrile | Calc'd 412, found |
| 1-21 | 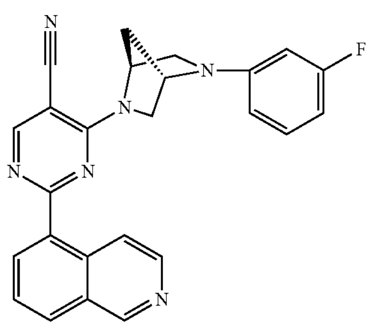 [SMILES: N#Cc1cnc(-c2cccc3cnccc23)nc1N1C[C@@H]2C[C@H]1CN2c1cccc(F)c1] | 4-[(1R,4S)-5-(3-fluorophenyl)-2,5-diazabicyclo[2.2.1]hept-2-yl]-2-isoquinolin-5-ylpyrimidine-5-carbonitrile | Calc'd 423, found |
| 1-22 | 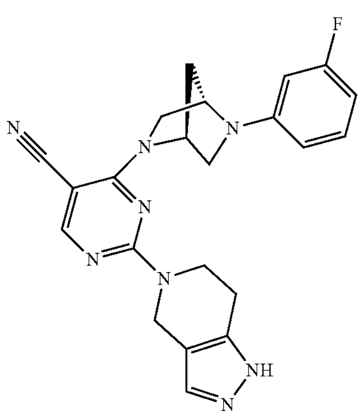 [SMILES: N#Cc1cnc(N2CCc3[nH]ncc3C2)nc1N1C[C@@H]2C[C@H]1CN2c1cccc(F)c1] | 4-[(1S,4R)-5-(3-fluorophenyl)-2,5-diazabicyclo[2.2.1]hept-2-yl]-2-(1,4,6,7-tetrahydro-5H-pyrazolo[4,3-c]pyridin-5-yl)pyrimidine-5-carbonitrile | Calc'd 417, found |

TABLE 1-continued

| Compound | Structure | Name | Exact Mass [M + H]+ |
|---|---|---|---|
| 1-23 | 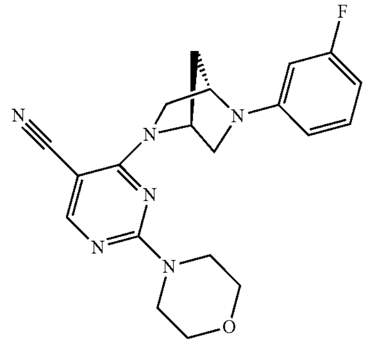 [SMILES: N#Cc1cnc(N2CCOCC2)nc1N1C[C@@H]2C[C@H]1CN2c1cccc(F)c1] | 4-[(1S,4R)-5-(3-fluorophenyl)-2,5-diazabicyclo[2.2.1]hept-2-yl]-2-morpholin-4-ylpyrimidine-5-carbonitrile | Calc'd 381, found |

Compound Examples for Table 2

Example 4

4-[(1S,4R)-5-(cyclopropylcarbonyl)-2,5-diazabicyclo[2.2.1]hept-2-yl]-2-(1-methyl-1H-pyrazol-4-yl)pyrimidine-5-carbonitrile (2-1)

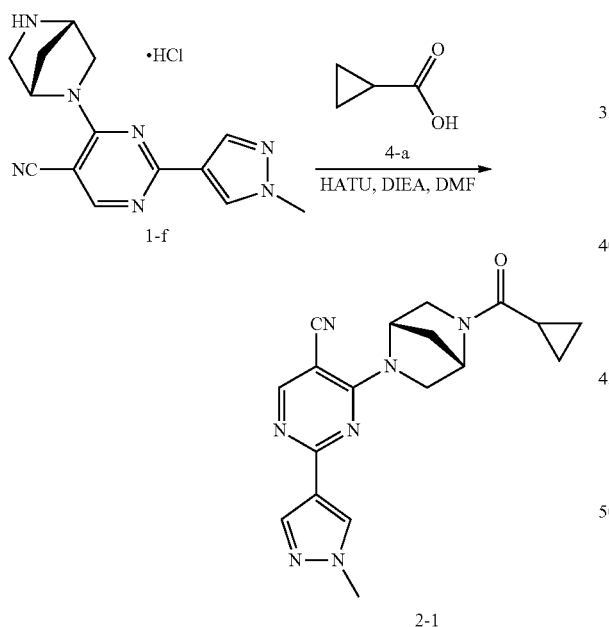

A vial was charged with cyclopropanecarboxylic acid (4-a) (0.070 mmol), HATU (26.7 mg, 0.070 mmol), 4-((1S, 4S)-2,5-diazabicyclo[2.2.1]heptan-2-yl)-2-(1-methyl-1H-pyrazol-4-yl)pyrimidine-5-carbonitrile HCl (1-f) (20 mg, 0.047 mmol), DMF (600 µl) and DIEA (50 µl, 0.286 mmol). The mixture was then stirred at RT for 18 h, after which the mixture was filtered and purified via reverse-phase HPLC (eluting with a 5:95 to 95:5 v/v acetonitrile:water with a 0.1% v/v TFA modifier) to afford compound 2-1. $^1$H NMR (500 MHz, DMSO-$d_6$) δ 8.59 (s, 1H), 8.39 (s, 1H), 8.01 (s, 1H), 3.88 (s, 3H), 3.97-3.82 (m, 3H), 3.80-3.62 (m, 3H), 2.51-2.46 (m, 1H), 2.14-1.89 (m, 2H), 0.80-0.63 (m, 4H). MS (ESI) Calc'd for $C_{18}H_2N_7O$ [M+1]$^+$, 350; found, 350.

Example 5

4-[(1S,4R)-5-(cyclopropylsulfonyl)-2,5-diazabicyclo[2.2.1]hept-2-yl]-2-(1-methyl-1H-pyrazol-4-yl)pyrimidine-5-carbonitrile (2-2)

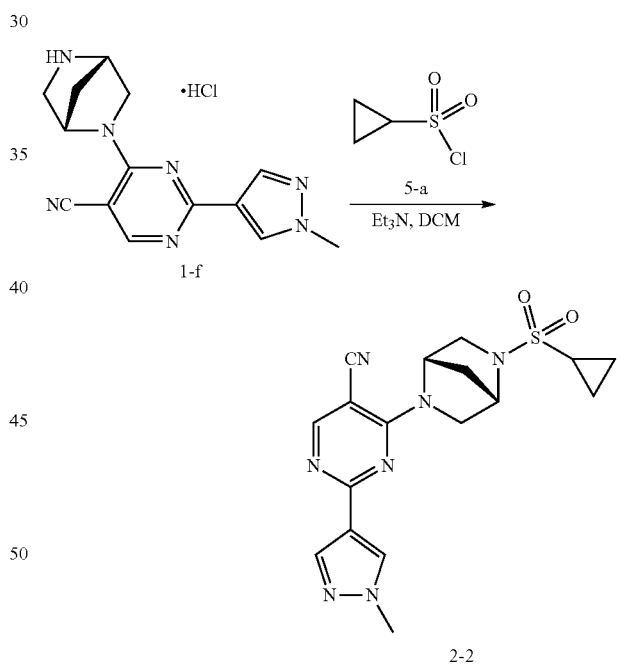

To a vial containing 4-((1S,4S)-2,5-diazabicyclo[2.2.1] heptan-2-yl)-2-(1-methyl-1H-pyrazol-4-yl)pyrimidine-5-carbonitrile HCl (1-f) (25 mg, 0.064 mmol) in DCM (350 µl), was added Et$_3$N (trimethylamine) (70 µl, 0.502 mmol), then cyclopropanesulfonyl chloride (5-a) (14.7 mg, 0.105 mmol) in DCM (300 µl). The reaction was stirred at RT for 16 h, after which the solvent was removed in vacuo and the residue was dissolved in DMSO and purified via reverse-phase HPLC (eluting with ACN/water, 0.1% TFA) to afford compound 2-2. $^1$H NMR (500 MHz, DMSO-$d_6$) δ 8.62 (s, 1H), 8.39 (s, 1H), 8.02 (s, 1H), 3.88 (s, 3H), 3.92-3.78 (m, 4H), 3.62-3.52 (m, 1H), 3.35-3.29 (m, 1H), 2.77 (p, J=6.6 Hz, 1H), 2.10-1.94 (m, 2H), 1.06-0.90 (m, 4H).

MS (ESI) Calc'd for $C_{17}H_{20}N_7O_2S$ [M+1]$^+$, 386; found, 386.

Example 6

4-[(1S,4R)-5-(cyclopropylmethyl)-2,5-diazabicyclo[2.2.1]hept-2-yl]-2-(1-methyl-1H-pyrazol-4-yl)pyrimidine-5-carbonitrile (2-3)

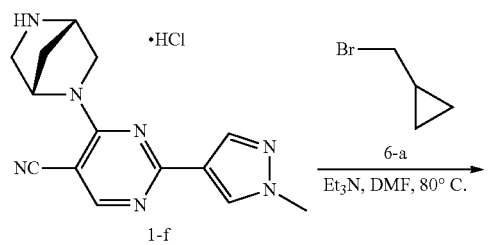

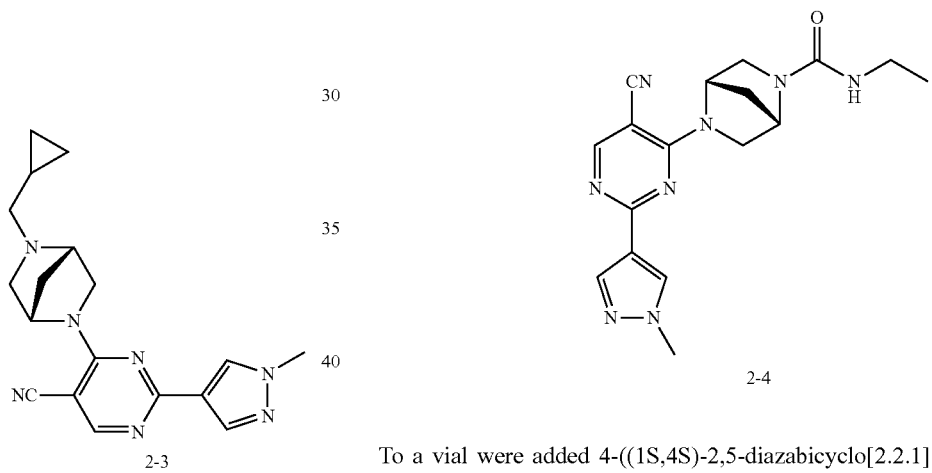

To a vial were added 4-((1S,4S)-2,5-diazabicyclo[2.2.1]heptan-2-yl)-2-(1-methyl-1H-pyrazol-4-yl)pyrimidine-5-carbonitrile HCl (1-f) (25 mg, 0.064 mmol), DMF (500 µl), Et₃N (100 µl, 0.717 mmol) and bromomethyl cyclopropane (6-a) (12.9 mg, 0.096 mmol). The mixture was heated at 80° C. for 18 h. The mixture was then filtered and purified via reverse-phase HPLC (eluting with ACN/water, 0.1% TFA) to afford compound 2-3. $^1$H NMR (500 MHz, DMSO-d$_6$) δ 8.55 (s, 1H), 8.35 (s, 1H), 7.98 (s, 1H), 3.87 (s, 3H), 3.82-3.63 (m, 3H), 3.37-3.28 (m, 1H), 3.05-2.92 (m, 1H), 2.64-2.52 (m, 1H), 2.49-2.29 (m, 2H), 1.96-1.69 (m, 2H), 0.87-0.73 (m, 1H), 0.46-0.34 (m, 2H), 0.15-0.02 (m, 2H). MS (ESI) Calc'd for $C_{18}H_{22}N_7$ [M+1]$^+$, 336; found, 336.

Example 7

(1R,4S)-5-[5-cyano-2-(1-methyl-1H-pyrazol-4-yl)pyrimidin-4-yl]-N-ethyl-2,5-diazabicyclo[2.2.1]heptane-2-carboxamide (2-4)

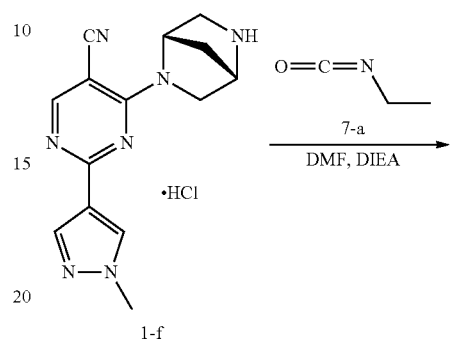

To a vial were added 4-((1S,4S)-2,5-diazabicyclo[2.2.1]heptan-2-yl)-2-(1-methyl-1H-pyrazol-4-yl)pyrimidine-5-carbonitrile HCl (1-f) (25 mg, 0.064 mmol), isocyanatoethane (7-a) (7.1 mg, 0.1 mmol), DMF (600 µl) and DIEA (50 µl, 0.286 mmol). The mixture was then stirred at RT for 18 h. The mixture was filtered and purified via reverse-phase HPLC (eluting with ACN/water, 0.1% TFA) to afford compound 2-4. $^1$H NMR (500 MHz, DMSO-d$_6$) δ 8.59 (s, 1H), 8.39 (s, 1H), 8.01 (s, 1H), 4.59 (s, 1H), 3.88 (s, 3H), 3.86-3.60 (m, 2H), 3.44-3.22 (m, 1H), 3.09-2.90 (m, 2H), 2.54-2.47 (m, 3H), 2.00-1.82 (m, 2H), 0.97 (t, J=7.1 Hz, 3H). MS (ESI) Calc'd for $C_{17}H_{21}N_8O$ [M+1]$^+$, 353; found, 353.

Compounds 2-5 through 2-21 found in Table 2 were prepared in a similar manner to that of Compound 2-1 of Example 4 using the corresponding carboxylic acids.

Compounds 2-13 through 2-15 found in Table 2 were prepared in a similar manner to that disclosed for Compound 2-2 in Example 5 using the corresponding sulfonyl chlorides.

Compound 2-16 found in Table 2 was prepared in a similar manner to that of Compound 2-3 of Example 6 using the corresponding alkyl bromide.

TABLE 2

| Compound | Structure | Name | Exact Mass [M + H]+ |
|---|---|---|---|
| 2-1 | 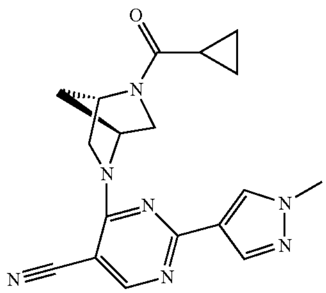 [SMILES: Cn1cc(-c2ncc(C#N)c(N3C[C@@H]4C[C@H]3CN4C(=O)C3CC3)n2)cn1] | 4-[(1S,4R)-5-(cyclopropylcarbonyl)-2,5-diazabicyclo[2.2.1]hept-2-yl]-2-(1-methyl-1H-pyrazol-4-yl)pyrimidine-5-carbonitrile | Calc'd 350, found 350 |
| 2-2 | 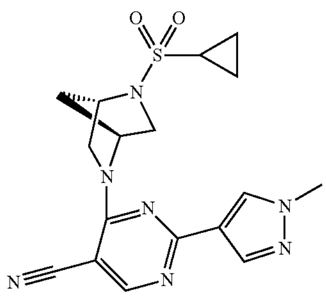 [SMILES: Cn1cc(-c2ncc(C#N)c(N3C[C@@H]4C[C@H]3CN4S(=O)(=O)C3CC3)n2)cn1] | 4-[(1S,4R)-5-(cyclopropylsulfonyl)-2,5-diazabicyclo[2.2.1]hept-2-yl]-2-(1-methyl-1H-pyrazol-4-yl)pyrimidine-5-carbonitrile | Calc'd 386, found 386 |
| 2-3 | 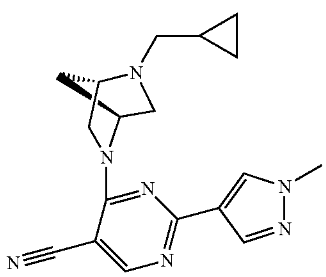 [SMILES: Cn1cc(-c2ncc(C#N)c(N3C[C@@H]4C[C@H]3CN4CC3CC3)n2)cn1] | 4-[(1S,4R)-5-(cyclopropylmethyl)-2,5-diazabicyclo[2.2.1]hept-2-yl]-2-(1-methyl-1H-pyrazol-4-yl)pyrimidine-5-carbonitrile | Calc'd 336, found 336 |
| 2-4 | 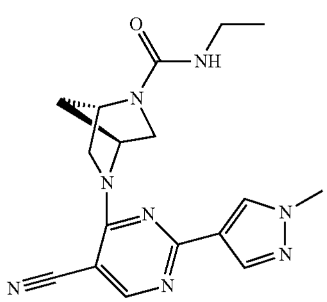 [SMILES: CCNC(=O)N1C[C@@H]2C[C@H]1CN2c1nc(-c2cnn(C)c2)ncc1C#N] | (1R,4S)-5-[5-cyano-2-(1-methyl-1H-pyrazol-4-yl)pyrimidin-4-yl]-N-ethyl-2,5-diazabicyclo[2.2.1]heptane-2-carboxamide | Calc'd 353, found 353 |
| 2-5 | 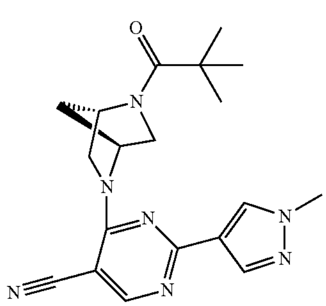 [SMILES: Cn1cc(-c2ncc(C#N)c(N3C[C@@H]4C[C@H]3CN4C(=O)C(C)(C)C)n2)cn1] | 4-[(1S,4R)-5-(2,2-dimethylpropanoyl)-2,5-diazabicyclo[2.2.1]hept-2-yl]-2-(1-methyl-1H-pyrazol-4-yl)pyrimidine-5-carbonitrile | Calc'd 366, found 366 |

TABLE 2-continued

| Compound | Structure | Name | Exact Mass [M + H]+ |
|---|---|---|---|
| 2-6 | 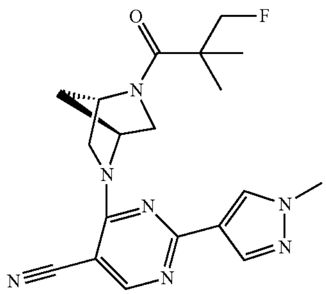 [SMILES: Cn1cc(-c2ncc(C#N)c(N3C[C@@H]4C[C@H]3CN4C(=O)C(C)(C)CF)n2)cn1] | 4-[(1S,4R)-5-(3-fluoro-2,2-dimethylpropanoyl)-2,5-diazabicyclo[2.2.1]hept-2-yl]-2-(1-methyl-1H-pyrazol-4-yl)pyrimidine-5-carbonitrile | Calc'd 384, found 384 |
| 2-7 | 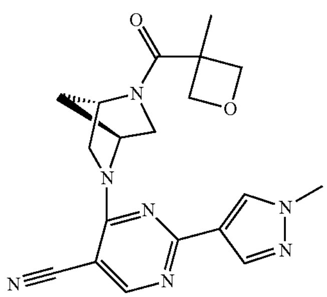 [SMILES: Cn1cc(-c2ncc(C#N)c(N3C[C@@H]4C[C@H]3CN4C(=O)C3(C)COC3)n2)cn1] | 4-{(1S,4R)-5-[(3-methyloxetan-3-yl)carbonyl]-2,5-diazabicyclo[2.2.1]hept-2-yl}-2-(1-methyl-1H-pyrazol-4-yl)pyrimidine-5-carbonitrile | Calc'd 380, found 380 |
| 2-8 | 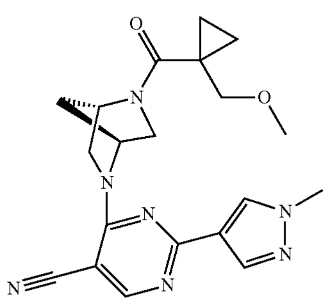 [SMILES: COCC1(C(=O)N2C[C@@H]3C[C@H]2CN3c2nc(-c3cnn(C)c3)ncc2C#N)CC1] | 4-[(1S,4R)-5-{[1-(methoxymethyl)cyclopropyl]carbonyl}-2,5-diazabicyclo[2.2.1]hept-2-yl]-2-(1-methyl-1H-pyrazol-4-yl)pyrimidine-5-carbonitrile | Calc'd 394, found 394 |
| 2-9 | 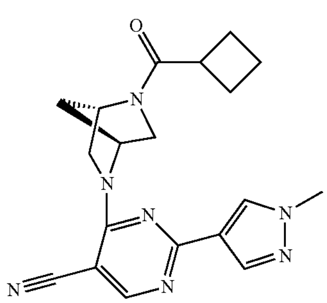 [SMILES: Cn1cc(-c2ncc(C#N)c(N3C[C@@H]4C[C@H]3CN4C(=O)C3CCC3)n2)cn1] | 4-[(1S,4R)-5-(cyclobutylcarbonyl)-2,5-diazabicyclo[2.2.1]hept-2-yl]-2-(1-methyl-1H-pyrazol-4-yl)pyrimidine-5-carbonitrile | Calc'd 364, found 364 |
| 2-10 | 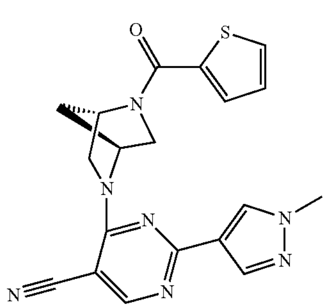 [SMILES: Cn1cc(-c2ncc(C#N)c(N3C[C@@H]4C[C@H]3CN4C(=O)c3cccs3)n2)cn1] | 2-(1-methyl-1H-pyrazol-4-yl)-4-[(1S,4R)-5-(thiophen-2-ylcarbonyl)-2,5-diazabicyclo[2.2.1]hept-2-yl]pyrimidine-5-carbonitrile | Calc'd 392, found 392 |

TABLE 2-continued

| Compound | Structure | Name | Exact Mass [M + H]+ |
|---|---|---|---|
| 2-11 | 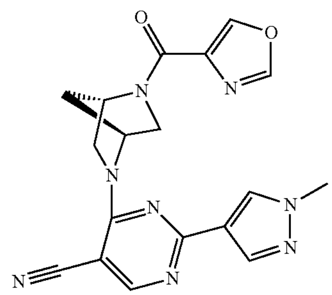 [SMILES: Cn1cc(-c2ncc(C#N)c(N3C[C@@H]4C[C@H]3CN4C(=O)c3cocn3)n2)cn1] | 2-(1-methyl-1H-pyrazol-4-yl)-4-[(1S,4R)-5-(1,3-oxazol-4-ylcarbonyl)-2,5-diazabicyclo[2.2.1]hept-2-yl]pyrimidine-5-carbonitrile | Calc'd 377, found 377 |
| 2-12 | 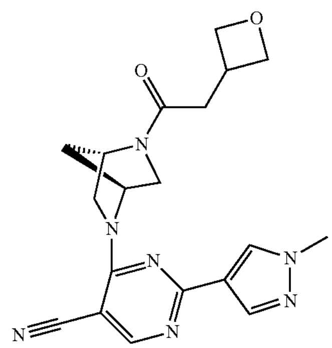 [SMILES: Cn1cc(-c2ncc(C#N)c(N3C[C@@H]4C[C@H]3CN4C(=O)CC3COC3)n2)cn1] | 2-(1-methyl-1H-pyrazol-4-yl)-4-[(1S,4R)-5-(oxetan-3-ylacetyl)-2,5-diazabicyclo[2.2.1]hept-2-yl]pyrimidine-5-carbonitrile | Calc'd 380, found 380 |
| 2-13 | 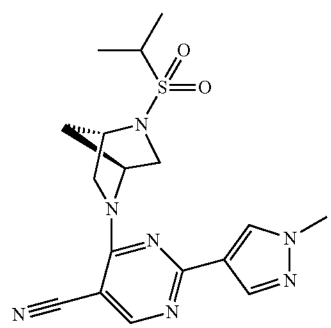 [SMILES: CC(C)S(=O)(=O)N1C[C@@H]2C[C@H]1CN2c1nc(-c2cnn(C)c2)ncc1C#N] | 4-{(1S,4R)-5-[(1-methylethyl)sulfonyl]-2,5-diazabicyclo[2.2.1]hept-2-yl}-2-(1-methyl-1H-pyrazol-4-yl)pyrimidine-5-carbonitrile | Calc'd 388, found 388 |
| 2-14 | 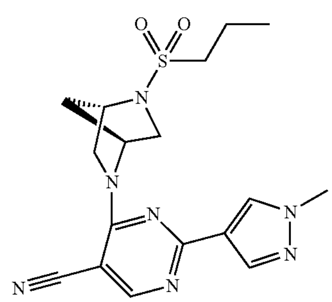 [SMILES: CCCS(=O)(=O)N1C[C@@H]2C[C@H]1CN2c1nc(-c2cnn(C)c2)ncc1C#N] | 2-(1-methyl-1H-pyrazol-4-yl)-4-[(1S,4R)-5-(propylsulfonyl)-2,5-diazabicyclo[2.2.1]hept-2-yl]pyrimidine-5-carbonitrile | Calc'd 388, found 388 |
| 2-15 | 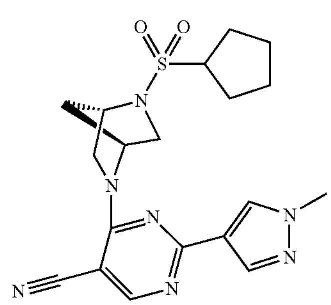 [SMILES: Cn1cc(-c2ncc(C#N)c(N3C[C@@H]4C[C@H]3CN4S(=O)(=O)C3CCCC3)n2)cn1] | 4-[(1S,4R)-5-(cyclopentylsulfonyl)-2,5-diazabicyclo[2.2.1]hept-2-yl]-2-(1-methyl-1H-pyrazol-4-yl)pyrimidine-5-carbonitrile | Calc'd 414, found 414 |

TABLE 2-continued

| Compound | Structure | Name | Exact Mass [M + H]+ |
|---|---|---|---|
| 2-16 | 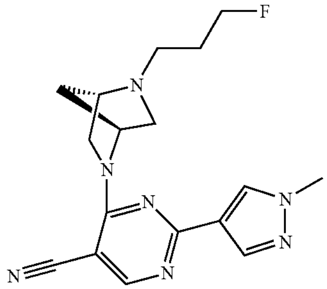 [SMILES: Cn1cc(-c2ncc(C#N)c(N3C[C@@H]4C[C@H]3CN4CCCF)n2)cn1] | 4-[(1S,4R)-5-(3-fluoropropyl)-2,5-diazabicyclo[2.2.1]hept-2-yl]-2-(1-methyl-1H-pyrazol-4-yl)pyrimidine-5-carbonitrile | Calc'd 342, found 342 |

Compound Examples for Table 3

Example 8

4-[4-(3-fluorophenyl)-3,3-dimethylpiperazin-1-yl]-2-(1-methyl-1H-pyrazol-4-yl)pyrimidine-5-carbonitrile (3-1)

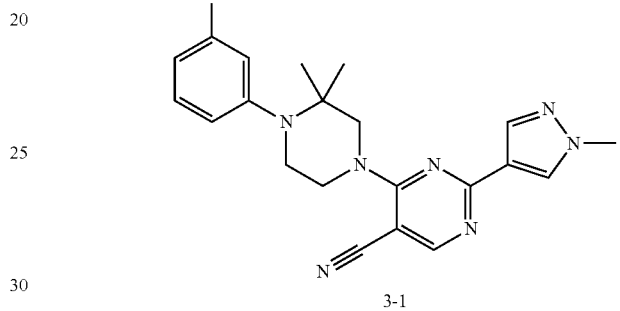

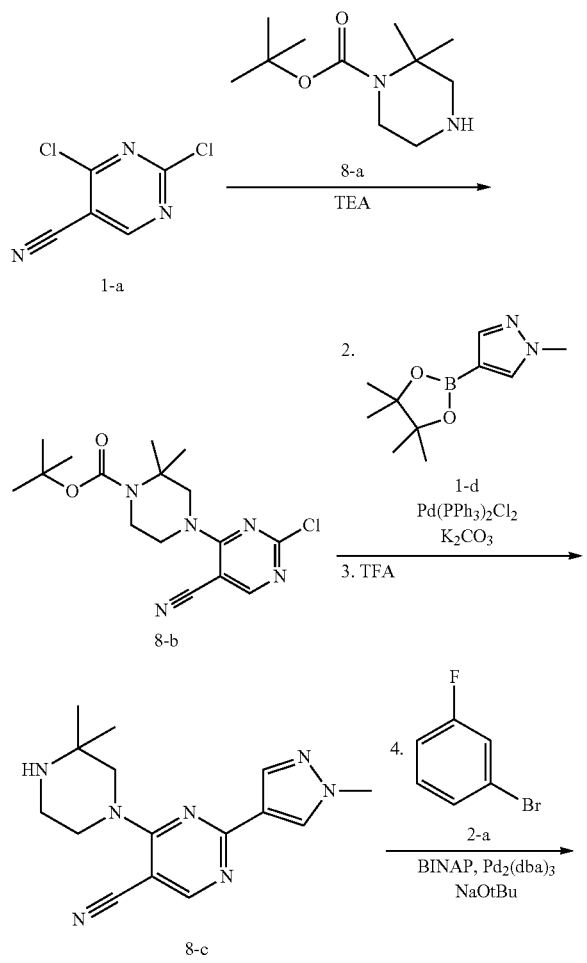

Step 1 tert-butyl 4-(2-chloro-5-cyanopyrimidin-4-yl)-2,2-dimethylpiperazine-1-carboxylate (8-b)

To a solution of 2,4-dichloropyrimidine-5-carbonitrile (1-a) (600 mg, 3.5 mmol) in THF (14 mL) were sequentially added TEA (698 mg, 6.90 mmol) and tert-butyl 2,2-dimethylpiperazine-1-carboxylate (8-a) (739 mg, 3.45 mmol) drop wise at −10° C. with stirring. The resulting solution was stirred at −10° C. for 30 min. The solution was then concentrated in vacuo. The crude residue was purified by reverse-phase preparative flash column chromatography (eluting with 25-60% acetonitrile in water) to afford tert-butyl 4-(2-chloro-5-cyanopyrimidin-4-yl)-2,2-dimethylpiperazine-1-carboxylate (8-b). MS (ESI) Calc'd for ($C_{16}H_{23}ClN_5O_2$) [M+H]+, 352, found, 352.

Step 2 tert-butyl 4-(5-cyano-2-(1-methyl-1H-pyrazol-4-yl)pyrimidin-4-yl)-2,2-dimethylpiperazine-1-carboxylate (Intermediate 8)

A degassed solution of tert-butyl 4-(2-chloro-5-cyanopyrimidin-4-yl)-2,2-dimethylpiperazine-1-carboxylate (8-b) (340 mg, 0.97 mmol), 1-methyl-4-(4,4,5,5-tetramethyl-1,3,2-dioxaborolan-2-yl)-1H-pyrazole (1-d) (261 mg, 1.26 mmol), potassium carbonate (401 mg, 2.90 mmol) and $PdCl_2(dppf)\cdot CH_2Cl_2$ adduct (79 mg, 0.097 mmol) in 1,4-dioxane (4 mL) and water (1 mL) was stirred at 80° C. for 2 hours under nitrogen. The reaction mixture was then cooled and concentrated in vacuo. The residue was then purified by column chromatography (silica gel, eluting with 5% methanol in dichloromethane) to afford tert-butyl 4-(5-cyano-2-(1-methyl-1H-pyrazol-4-yl)pyrimidin-4-yl)-2,2-dimethylpiperazine-1-carboxylate (Intermediate 8). MS (ESI) Calc'd for ($C_2H_{28}N_7O_2$) [M+H]+, 398, found, 398.

Step 3 4-(3,3-dimethylpiperazin-1-yl)-2-(1-methyl-1H-pyrazol-4-yl)pyrimidine-5-carbonitrile (8-c)

To a solution of tert-butyl 4-(5-cyano-2-(1-methyl-H-pyrazol-4-yl)pyrimidin-4-yl)-2,2-dimethylpiperazine-1-carboxylate (Intermediate 8) (220 mg, 0.55 mmol) in DCM (4 mL) was added TFA (1.5 mL) at 20° C. The resulting solution was stirred for 1 h at 20° C. The resulting solution was then made basic via the addition of saturated aqueous sodium carbonate aqueous solution (final pH=10). The mixture was then extracted with chloroform (5×30 mL), and the combined organic layers were dried over anhydrous sodium sulfate, filtered, and concentrated under vacuum. The residue was purified by column chromatography (silica gel, eluting with 10% methanol in dichloromethane) to afford 4-(3,3-dimethylpiperazin-1-yl)-2-(1-methyl-1H-pyrazol-4-yl)pyrimidine-5-carbonitrile (8-c). MS (ESI) Calc'd for ($C_{15}H_{20}N_7$) [M+H]$^+$, 298, found, 298.

Step 4 4-[4-(3-fluorophenyl)-3,3-dimethylpiperazin-1-yl]-2-(1-methyl-1H-pyrazol-4-yl)pyrimidine-5-carbonitrile (3-1)

A degassed solution of 4-(3,3-dimethylpiperazin-1-yl)-2-(1-methyl-1H-pyrazol-4-yl)pyrimidine-5-carbonitrile (8-c) (100 mg, 0.34 mmol), 1-bromo-3-fluorobenzene (2-a) (88 mg, 0.50 mmol), sodium 2-methylpropan-2-olate (NaOtBu) (97 mg, 1.0 mmol), 2,2'-bis(diphenylphosphino)-1,1'-binaphthalene (BINAP) (41.9 mg, 0.067 mmol) and Pd$_2$(dba)$_3$-CHCl$_3$ adduct (34.8 mg, 0.034 mmol) in toluene (5 mL) was stirred at 100° C. for 1 h in a microwave reactor under nitrogen. The reaction mixture was then concentrated in vacuo. The resulting residue was purified by flash column chromatography with (silica gel, eluting with 3% methanol in dichloromethane) to afford 4-(4-(3-fluorophenyl)-3,3-dimethylpiperazin-1-yl)-2-(1-methyl-1H-pyrazol-4-yl)pyrimidine-5-carbonitrile (3-1). $^1$H NMR (500 MHz, DMSO-d6) δ 8.66 (s, 1H), 8.44 (s, 1H), 8.06 (s, 1H), 7.37-7.23 (m, 1H), 7.02-6.86 (m, 3H), 4.09 (s, 2H), 3.80-4.02 (m, 4H), 3.17-3.38 (m, 3H), 1.09 (s, 6H). MS (ESI) Calc'd for ($C_2H_{23}FN_7$) [M+H]$^+$, 392, found, 392.

Example 9

4-(4-(3-fluorophenyl)piperazin-1-yl)-2-(1-methyl-1H-pyrazol-4-yl)pyrimidine-5-carbonitrile (3-2)

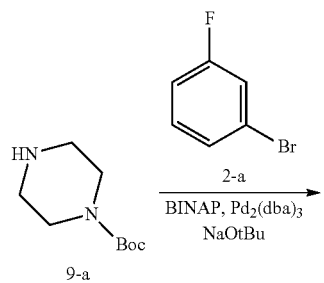

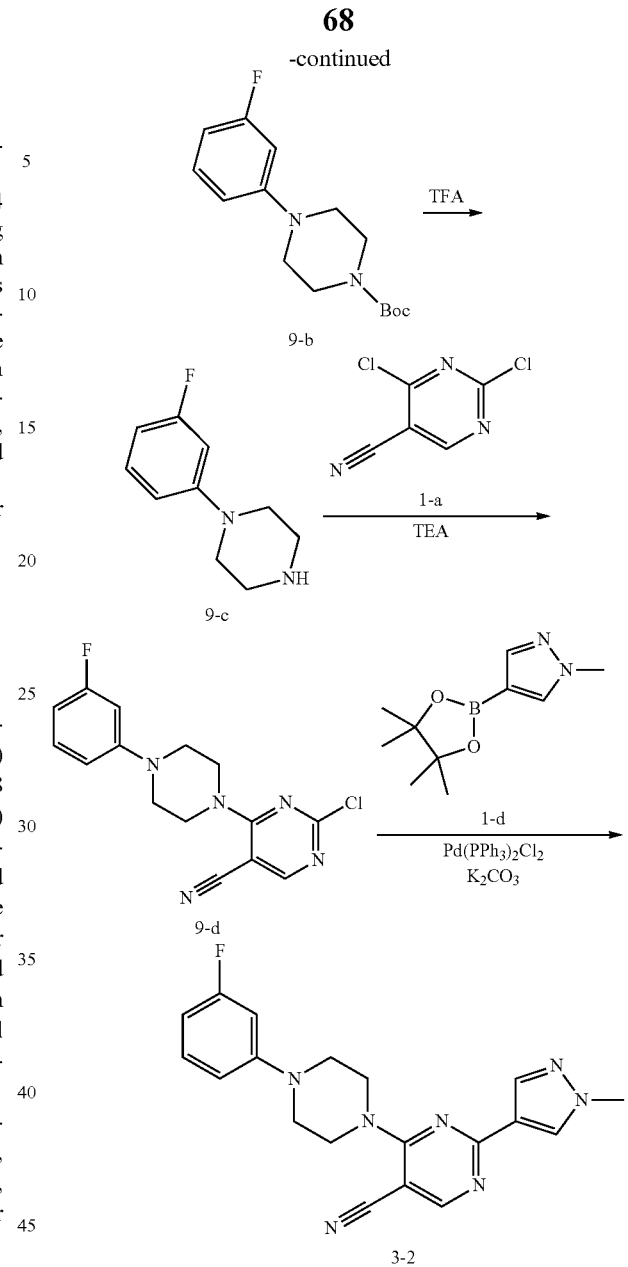

Step 1 tert-butyl 4-(3-fluorophenyl)piperazine-1-carboxylate (9-b)

To a degassed solution of tert-butyl piperazine-1-carboxylate (9-a) (1 g, 5.4 mmol), 1-bromo-3-fluorobenzene (2-a) (1.03 g, 5.9 mmol) and sodium tert-butoxide (NaOtBu) (1.03 g, 10.7 mmol) in toluene (20 ml) was added tris(dibenzylideneacetone)palladium-chloroform adduct (Pd$_2$(dba)$_3$.CHCl$_3$) (0.56 g, 0.54 mmol) and (R)-(+)-2,2'-bis(diphenylphosphino)-1,1'-binapthyl (BINAP)(0.33 g, 0.54 mmol) under nitrogen at RT. The resulting solution was stirred at 80° C. for 2 h, after which the reaction was cooled to RT and quenched by the addition of water (5 mL). The resulting solution was extracted with EtOAc (3 times 50 mL), dried over sodium sulfate, filtered, and the solvent removed in vacuo. The resulting residue was purified by column chromatography (silica gel, eluting with petroleum ether:EtOAc=20:1) to give tert-butyl 4-(3-fluorophenyl)piperazine- 1-carboxylate (9-b). MS (ESI) Calc'd for (C$_{H_{14}FN_2O_2}$) [M+H-tBu]$^+$, 225, found 225.

Step 2 1-(3-fluorophenyl)piperazine (9-c)

To a solution of tert-butyl 4-(3-fluorophenyl)piperazine-1-carboxylate (9-b) (2.3 g, 8.20 mmol) in DCM (15 ml) was added TFA (3 ml, 40 mmol) drop wise at RT. The resulting solution was stirred at RT for 2 h, after which the reaction was quenched by the addition of aqueous sodium bicarbonate and the mixture was extracted with DCM (3×10 mL). The combined organic layers were washed with brine (3×10 mL), dried over sodium sulfate, filtered, and concentrated in vacuo to give 1-(3-fluorophenyl)piperazine (9-c) which was used without further purification.

Step 3 2-chloro-4-(4-(3-fluorophenyl)piperazin-1-yl)pyrimidine-5-carbonitrile (9-d)

To a solution of 2,4-dichloropyrimidine-5-carbonitrile (1-a) (0.5 g, 2.9 mmol) in EtOH (5 ml) was added 1-(3-fluorophenyl)piperazine (9-c) (0.52 g, 2.9 mmol) and TEA (0.29 g, 2.9 mmol) at 0° C. and then the resulting mixture was stirred for 2 h at 0° C. the reaction mixture was then concentrated in vacuo, and the residue was purified by column chromatography (silica gel, eluting 0-10% MeOH in DCM) to afford 2-chloro-4-(4-(3-fluorophenyl)piperazin-1-yl)pyrimidine-5-carbonitrile (9-d). MS (ESI) Calc'd for (C$_{15}$H$_{14}$ClFN$_5$) [M+H]$^+$, 318, found, 318.

Step 4 4-(4-(3-fluorophenyl)piperazin-1-yl)-2-(1-methyl-1H-pyrazol-4-yl)pyrimidine-5-carbonitrile (3-2)

To a solution of 2-chloro-4-(4-(3-fluorophenyl)piperazin-1-yl)pyrimidine-5-carbonitrile (9-d) (40 mg, 0.13 mmol), 1-methyl-4-(4,4,5,5-tetramethyl-1,3,2-dioxaborolan-2-yl)-1H-pyrazole (1-d) (28.8 mg, 0.14 mmol) in dioxane (1 ml)/water (0.25 ml) was added Pd(PPh$_3$)$_2$Cl$_2$ (13.3 mg, 0.019 mmol) and potassium carbonate (K$_2$CO$_3$) (52.2 mg, 0.38 mmol) under nitrogen. The resulting solution was stirred at 80° C. for 4 hours. The reaction was then quenched by the addition of water (1 mL), and the aqueous solution was extracted with DCM (3×10 mL), dried over sodium sulfate, filtered, and the solvent was removed in vacuo. The resulting residue was purified by column chromatography (silica gel, eluting with DCM:MeOH 50:1) to afford 4-(4-(3-fluorophenyl)piperazin-1-yl)-2-(1-methyl-1H-pyrazol-4-yl)pyrimidine-5-carbonitrile (3-2). $^1$H NMR (500 MHz, DMSO-d6) δ 8.67 (s, 1H), 8.42 (s, 1H), 8.04 (s, 1H), 7.17-7.31 (m, 1H), 6.80 (s, 2H), 6.57 (s, 1H), 4.11 (s, 5H), 3.90 (s, 3H), 3.21-3.51 (m, 3H). MS (ESI) Calc'd for (C$_{19}$H$_{19}$FN$_7$) [M+H]$^+$, 364, found, 364.

Example 10

4-[(3R)-4-(3-fluorophenyl)-3-methylpiperazin-1-yl]-2-(1-methyl-1H-pyrazol-4-yl)pyrimidine-5-carbonitrile (3-3)

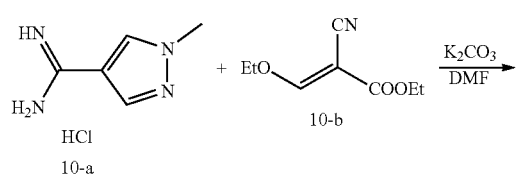

Step 1 4-hydroxy-2-(1-methyl-1H-pyrazol-4-yl)pyrimidine-5-carbonitrile (10-c)

1-methyl-1H-pyrazole-4-carboximidamide hydrochloride (10-a) (5.0 g, 31 mmol), ethyl (E)-2-cyano-3-ethoxyacrylate (10-b) (5.5 g, 33 mmol), potassium carbonate (12.9 g, 93 mmol) in DMF (78 mL) was heated to 60° C. The reaction was stirred at this temperature for 90 min, after which it was cooled to RT and HCl (0.2 N) was added to the mixture to adjust the pH to pH=4. The mixture was then cooled to 0° C. and was stirred for 10 min, after which the precipitate was collected via filtration and was washed with water. The cake

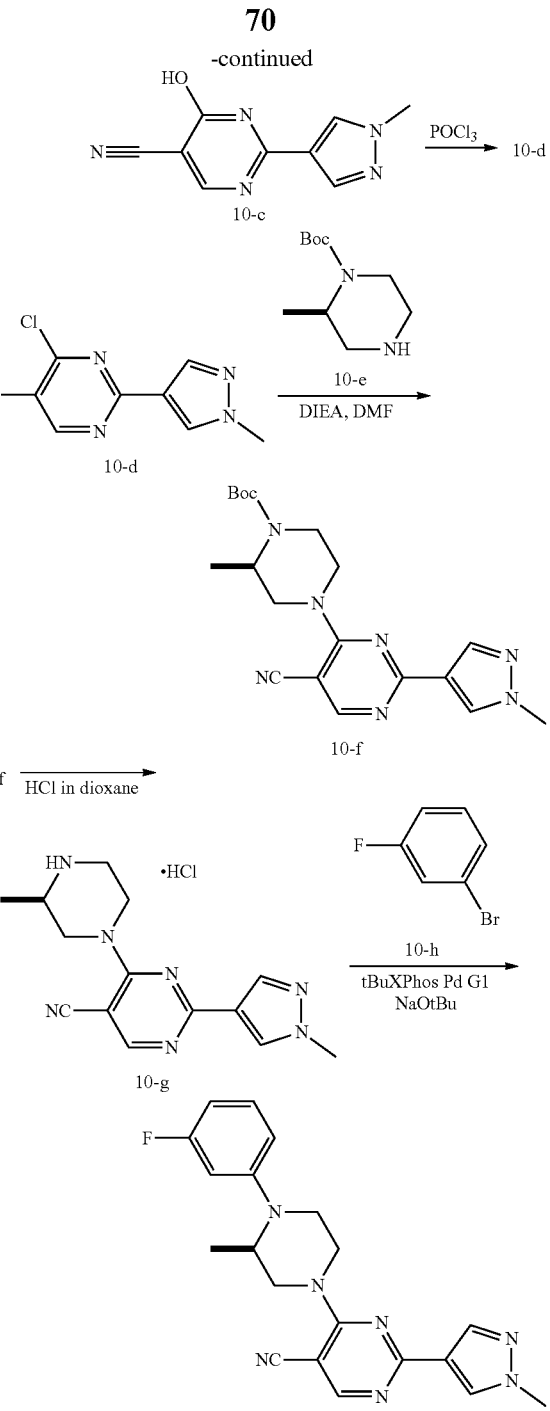

was further dried under vacuum (nitrogen flow) overnight to give 4-hydroxy-2-(1-methyl-H-pyrazol-4-yl)pyrimidine-5-carbonitrile (10-c) which was used in the next step without further purification. MS (ESI) Calc'd for ($C_9H_8N_5O$) [M+H]$^+$, 202; found, 202.

Step 2 4-chloro-2-(1-methyl-1H-pyrazol-4-yl)pyrimidine-5-carbonitrile (10-d)

4-hydroxy-2-(1-methyl-1H-pyrazol-4-yl) pyrimidine-5-carbonitrile (10-c) (1 g, 5 mmol) in POCl$_3$ (phosphoryl chloride) (4.6 mL, 50 mmol) was heated to 105° C. for 3 h. The reaction was then cooled to 0° C. and the mixture was slowly added to NaOH (sodium hydroxide) (4 g) in ice water (60 mL) (cooled in an ice bath) such that the inner temperature never increased to greater than 10° C. The resulting mixture was stirred at 0° C. for 10 min, after which the precipitate was collected via filtration and washed with water. The cake was then dried under vacuum (nitrogen flow) overnight to give 4-chloro-2-(1-methyl-H-pyrazol-4-yl)pyrimidine-5-carbonitrile (10-d). MS (ESI) Calc'd for ($C_9H_7ClN_5$) [M+H]$^+$, 220; found, 220.

Step 3 tert-butyl (R)-4-(5-cyano-2-(1-methyl-1H-pyrazol-4-yl)pyrimidin-4-yl)-2-methylpiperazine-1-carboxylate (10-f)

To a flask were added (R)-tert-butyl 2-methylpiperazine-1-carboxylate (10-e) (0.63 g, 3.15 mmol), compound 10-d (0.806 g, 3.67 mmol), DMF (20 ml) and DIEA (1.8 ml, 10.31 mmol). The mixture was stirred at RT for 16 h, after which the solvent was removed in vacuo. The residue was then dissolved into DCM and purified via column chromatography (silica gel, eluting with 0-80% EtOAc in MeOH) to afford tert-butyl (R)-4-(5-cyano-2-(1-methyl-1H-pyrazol-4-yl)pyrimidin-4-yl)-2-methylpiperazine-1-carboxylate (10-f). MS (ESI) Calc'd for $C_{19}H_{26}N_7O_2$ [M+H]$^+$, 384; found, 384.

Step 4 (R)-2-(1-methyl-1H-pyrazol-4-yl)-4-(3-methylpiperazin-1-yl)pyrimidine-5-carbonitrile hydrochloride (10-g)

To a vial were added tert-butyl (R)-4-(5-cyano-2-(1-methyl-1H-pyrazol-4-yl)pyrimidin-4-yl)-2-methylpiperazine-1-carboxylate (10-f) (597 mg, 1.56 mmol), dioxane (4 ml) and HCl in dioxane (4 ml, 16 mmol, 4M). The mixture was stirred at RT for 16 h, after which the solvent was removed in vacuo and the resulting (R)-2-(1-methyl-H-pyrazol-4-yl)-4-(3-methylpiperazin-1-yl)pyrimidine-5-carbonitrile hydrochloride (10-g) was used in the next step without further purification. MS (ESI) Calc'd for $C_{14}H_{18}N_7$ [M+H]$^+$, 284; found, 284.

Step 5 4-[(3R)-4-(3-fluorophenyl)-3-methylpiperazin-1-yl]-2-(1-methyl-1H-pyrazol-4-yl)pyrimidine-5-carbonitrile (3-3)

To a vial, were added compound 10-g (25 mg, 0.078 mmol), sodium tert-butoxide (NaOtBu) (22.5 mg, 0.235 mmol), tBuXPhos Pd G1 (8.05 mg, 0.012 mmol), THF (400 μl), and 1-bromo-3-fluorobenzene (10-h) (27.4 mg, 0.156 mmol). The mixture was evacuated and back filled with nitrogen (flushed 6 times). The mixture was then heated at 80° C. for 16 h, after which it was cooled to RT. Biotage® MP-TMT, a macroporous polystyrene-bound trimercaptotriazine (Biotage®, Charlotte, N.C., USA) was then added scavenge the catalyst, and the mixture was stirred at RT for 4 h. The mixture was then filtered and the filtrate was purified by reverse-phase HPLC (eluting with ACN/water (0.1% TFA)) to afford compound 3-3 as the TFA salt. $^1$H NMR (600 MHz, DMSO-d$_6$) δ 8.64 (s, 1H), 8.40 (s, 1H), 8.01 (s, 1H), 7.20 (q, J=8.0 Hz, 1H), 6.74-6.64 (m, 2H), 6.55-6.44 (m, 1H), 4.69 (d, J=13.2 Hz, 1H), 4.61 (d, J=13.4 Hz, 1H), 4.25-4.16 (m, 1H), 3.87 (s, 3H), 3.61 (dd, J=13.5, 3.3 Hz, 1H), 3.57-3.49 (m, 1H), 3.49-3.39 (m, 1H), 3.15 (td, J=12.4, 3.6 Hz, 1H), 0.99 (d, J=6.5 Hz, 3H). MS (ESI) Calc'd for $C_2H_{21}FN_7$ [M+1]$^+$, 378; found, 378.

Compound 3-4 found in Table 3, was prepared in a manner similar to Example 8 except that tert-butyl 3,8-diazabicyclo[3.2.1]octane-8-carboxylate was used in place of tert-butyl 2,2-dimethylpiperazine-1-carboxylate.

TABLE 3

| Compound | Structure | Name | Exact Mass [M + H]+ |
|---|---|---|---|
| 3-1 | 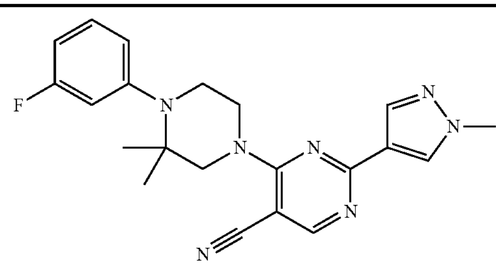 | 4-[4-(3-fluorophenyl)-3,3-dimethylpiperazin-1-yl]-2-(1-methyl-1H-pyrazol-4-yl)pyrimidine-5-carbonitrile | Calc'd 392, found 392 |
| 3-2 | 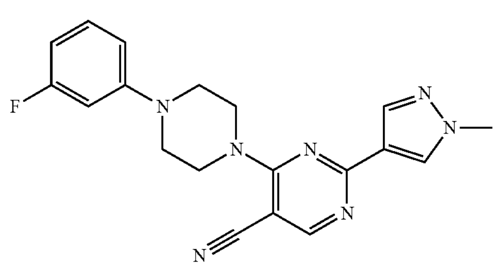 [SMILES: Cn1cc(-c2ncc(C#N)c(N3CCN(c4cccc(F)c4)CC3)n2)cn1] | 4-[4-(3-fluorophenyl)piperazin-1-yl]-2-(1-methyl-1H-pyrazol-4-yl)pyrimidine-5-carbonitrile | Calc'd 364, found 364 |

TABLE 3-continued

| Compound | Structure | Name | Exact Mass [M + H]+ |
|---|---|---|---|
| 3-3 | 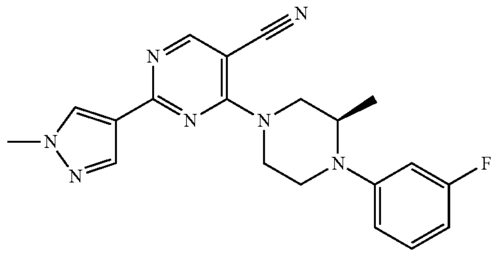 [SMILES: C[C@@H]1CN(c2nc(-c3cnn(C)c3)ncc2C#N)CCN1c1cccc(F)c1] | 4-[(3R)-4-(3-fluorophenyl)-3-methylpiperazin-1-yl]-2-(1-methyl-1H-pyrazol-4-yl)pyrimidine-5-carbonitrile | Calc'd 378, found 378 |
| 3-4 | 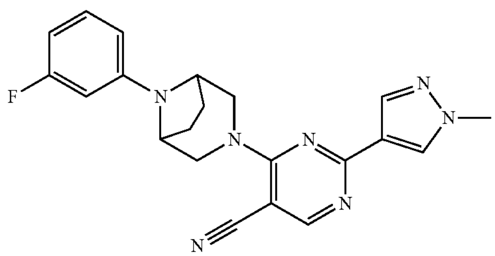 [SMILES: Cn1cc(-c2ncc(C#N)c(N3CC4CCC(C3)N4c3cccc(F)c3)n2)cn1] | 4-[8-(3-fluorophenyl)-3,8-diazabicyclo[3.2.1]oct-3-yl]-2-(1-methyl-1H-pyrazol-4-yl)pyrimidine-5-carbonitrile | Calc'd 390, found 390 |

Compound Examples for Table 4

Example 11

4-[(3R)-4-(cyclopropylcarbonyl)-3-methylpiperazin-1-yl]-2-(1-methyl-1H-pyrazol-4-yl)pyrimidine-5-carbonitrile (4-1)

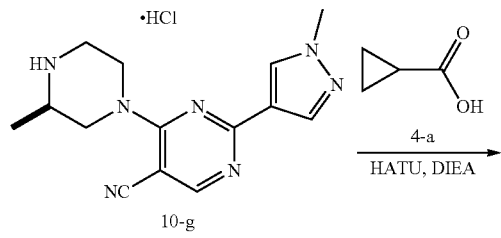

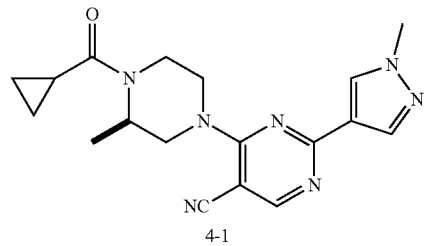

To a vial were added compound 10-g (0.957 g, 2.99 mmol), HATU (1.47 g, 3.86 mmol), DMF (34 ml), DIEA (5.0 ml, 29 mmol), and cyclopropanecarboxylic acid (4-a) (0.349 g, 4.05 mmol). The mixture was stirred at RT for 16 h, after which the solvent was removed in vacuo. The residue was dissolved into DCM and purified by column chromatography (silica gel, eluting with 2% MeOH in EtOAc) to afford compound 4-1. $^1$H NMR (600 MHz, DMSO-$d_6$) δ 8.63 (s, 1H), 8.39 (s, 1H), 8.01 (s, 1H), 4.69-4.40 (m, 3H), 4.16 (d, J=12.8 Hz, 1H), 3.86 (s, 3H), 3.73-3.46 (m, 2H), 3.19-3.04 (m, 1H), 2.04-1.87 (m, 1H), 1.36-1.06 (m, 5H), 0.84-0.58 (m, 2H). MS (ESI) Calc'd for $C_{18}H_{22}N_7O$ [M+H]$^+$, 352; found, 352.

Compounds 4-2 through 4-9 as found in Table 4, were prepared in a similar manner to Example 11 using the corresponding carboxylic acids.

Compounds 4-10 through 4-13 of Table 4, were prepared in a manner similar to Example 10, step 5 using the corresponding aryl bromides.

TABLE 4

| Compound | Structure | Name | Exact Mass [M + H]+ |
|---|---|---|---|
| 4-1 | 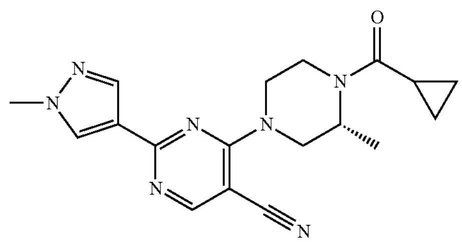 [SMILES: C[C@@H]1CN(c2nc(-c3cnn(C)c3)ncc2C#N)CCN1C(=O)C1CC1] | 4-[(3R)-4-(cyclopropylcarbonyl)-3-methylpiperazin-1-yl]-2-(1-methyl-1H-pyrazol-4-yl)pyrimidine-5-carbonitrile | Calc'd 352, found 352 |
| 4-2 | 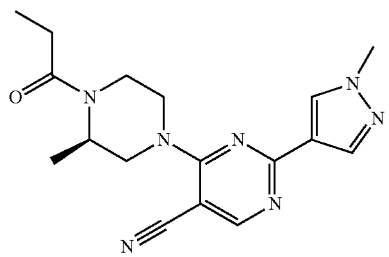 [SMILES: CCC(=O)N1CCN(c2nc(-c3cnn(C)c3)ncc2C#N)C[C@H]1C] | 4-[(3R)-3-methyl-4-propanoylpiperazin-1-yl]-2-(1-methyl-1H-pyrazol-4-yl)pyrimidine-5-carbonitrile | Calc'd 340, found 340 |
| 4-3 | 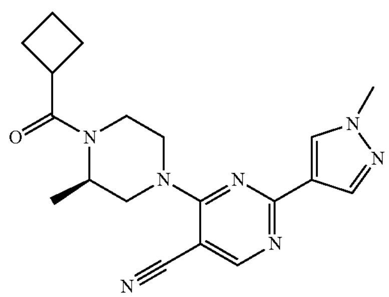 [SMILES: C[C@@H]1CN(c2nc(-c3cnn(C)c3)ncc2C#N)CCN1C(=O)C1CCC1] | 4-[(3R)-4-(cyclobutylcarbonyl)-3-methylpiperazin-1-yl]-2-(1-methyl-1H-pyrazol-4-yl)pyrimidine-5-carbonitrile | Calc'd 366, found 366 |
| 4-4 | 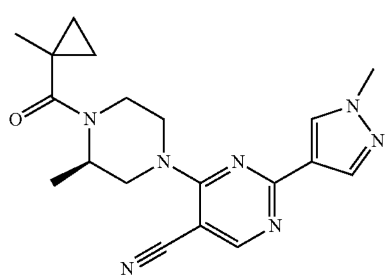 [SMILES: C[C@@H]1CN(c2nc(-c3cnn(C)c3)ncc2C#N)CCN1C(=O)C1(C)CC1] | 4-{(3R)-3-methyl-4-[(1-methylcyclopropyl)carbonyl]piperazin-1-yl}-2-(1-methyl-1H-pyrazol-4-yl)pyrimidine-5-carbonitrile | Calc'd 366, found 366 |
| 4-5 | 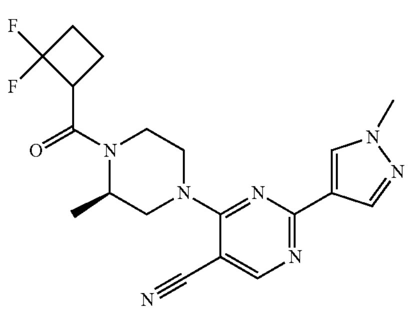 [SMILES: C[C@@H]1CN(c2nc(-c3cnn(C)c3)ncc2C#N)CCN1C(=O)C1CCC1(F)F] | 4-{(3R)-4-[(2,2-difluorocyclobutyl)carbonyl]-3-methylpiperazin-1-yl}-2-(1-methyl-1H-pyrazol-4-yl)pyrimidine-5-carbonitrile | Calc'd 402, found 402 |

TABLE 4-continued

| Compound | Structure | Name | Exact Mass [M + H]+ |
|---|---|---|---|
| 4-6 | 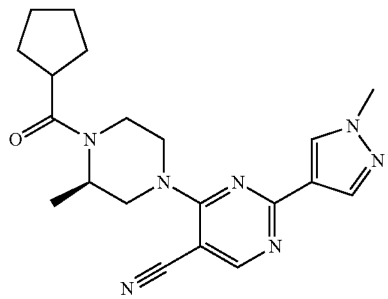 [SMILES: C[C@@H]1CN(c2nc(-c3cnn(C)c3)ncc2C#N)CCN1C(=O)C1CCCC1] | 4-[(3R)-4-(cyclopentylcarbonyl)-3-methylpiperazin-1-yl]-2-(1-methyl-1H-pyrazol-4-yl)pyrimidine-5-carbonitrile | Calc'd 380, found 380 |
| 4-7 | 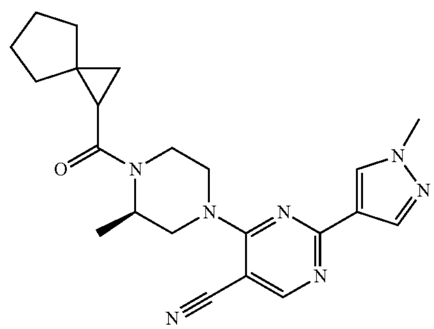 [SMILES: C[C@@H]1CN(c2nc(-c3cnn(C)c3)ncc2C#N)CCN1C(=O)C1CC12CCCC2] | 2-(1-methyl-1H-pyrazol-4-yl)-4-[(3R)-3-methyl-4-(spiro[2.4]hept-1-ylcarbonyl)piperazin-1-yl]pyrimidine-5-carbonitrile | Calc'd 406, found 406 |
| 4-8 | 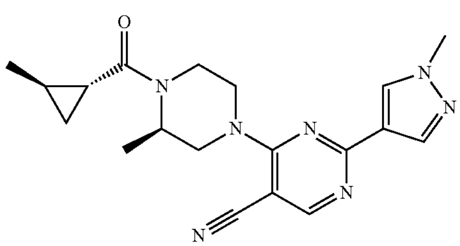 [SMILES: C[C@@H]1C[C@H]1C(=O)N1CCN(c2nc(-c3cnn(C)c3)ncc2C#N)C[C@H]1C] | 4-[(3R)-3-methyl-4-{[(1R,2R)-2-methylcyclopropyl]carbonyl}piperazin-1-yl]-2-(1-methyl-1H-pyrazol-4-yl)pyrimidine-5-carbonitrile | Calc'd 366, found 366 |
| 4-9 | 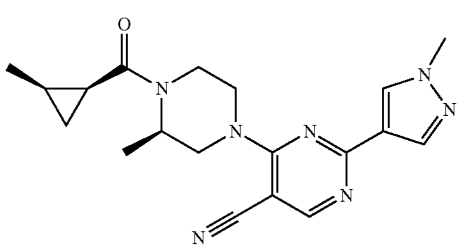 [SMILES: C[C@@H]1C[C@@H]1C(=O)N1CCN(c2nc(-c3cnn(C)c3)ncc2C#N)C[C@H]1C] | 4-[(3R)-3-methyl-4-{[(1S,2R)-2-methylcyclopropyl]carbonyl}piperazin-1-yl]-2-(1-methyl-1H-pyrazol-4-yl)pyrimidine-5-carbonitrile | Calc'd 366, found 366 |
| 4-10 | 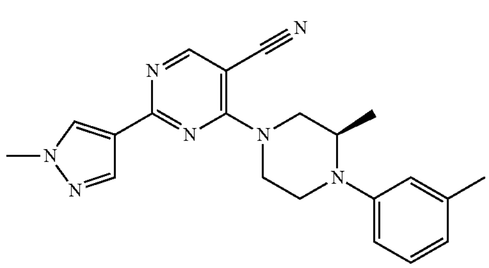 | 4-[(3R)-4-(3-fluorophenyl)-3-methylpiperazin-1-yl]-2-(1-methyl-1H-pyrazol-4-yl)pyrimidine-5-carbonitrile | Calc'd 378, found 378 |

TABLE 4-continued

| Compound | Structure | Name | Exact Mass [M + H]+ |
|---|---|---|---|
| 4-11 | 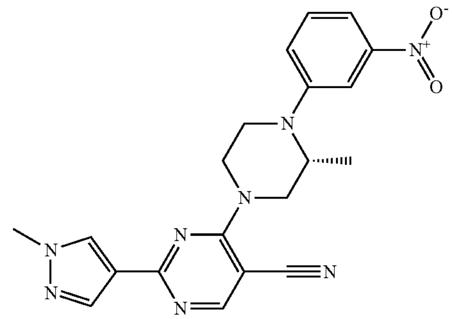 [SMILES: C[C@@H]1CN(c2nc(-c3cnn(C)c3)ncc2C#N)CCN1c1cccc([N+](=O)[O-])c1] | 4-[(3R)-3-methyl-4-(3-nitrophenyl)piperazin-1-yl]-2-(1-methyl-1H-pyrazol-4-yl)pyrimidine-5-carbonitrile | Calc'd 405, found 405 |
| 4-12 | 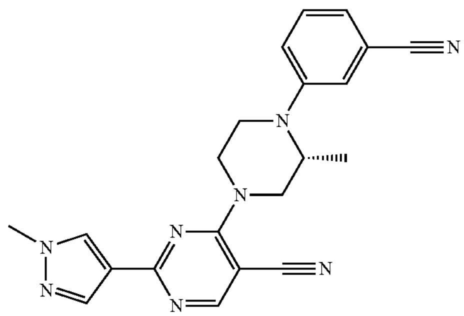 [SMILES: C[C@@H]1CN(c2nc(-c3cnn(C)c3)ncc2C#N)CCN1c1cccc(C#N)c1] | 4-[(3R)-4-(3-cyanophenyl)-3-melhylpiperazin-1-yl]-2-(1-methyl-1H-pyrazol-4-yl)pyrimidine-5-carbonitrile | Calc'd 385, found 385 |
| 4-13 | 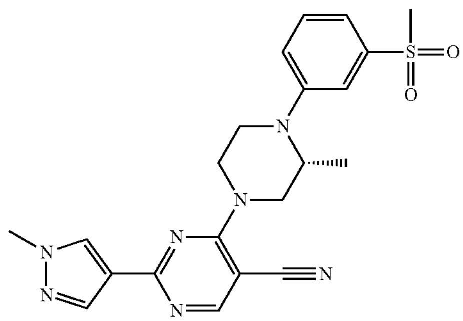 [SMILES: C[C@@H]1CN(c2nc(-c3cnn(C)c3)ncc2C#N)CCN1c1cccc(S(C)(=O)=O)c1] | 4-{(3R)-3-methyl-4-[3-(methylsulfonyl)phenyl]piperazin-1-yl}-2-(1-methyl-1H-pyrazol-4-yl)pyrimidine-5-carbonitrile | Calc'd 438, found 438 |

Compound Examples for Table 5

Example 12

3-{2-[(3R)-4-(cyclopropylcarbonyl)-3-methylpiperazin-1-yl]-4-(1-methyl-1H-pyrazol-4-yl)pyrimidin-5-yl}prop-2-yn-1-ol (5-1)

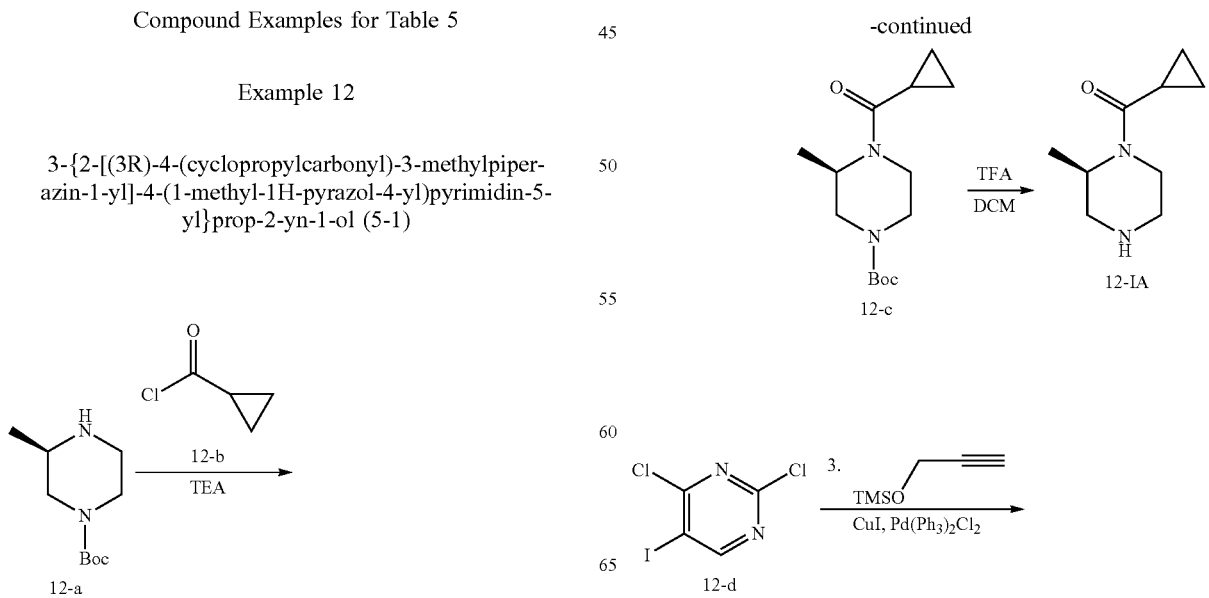

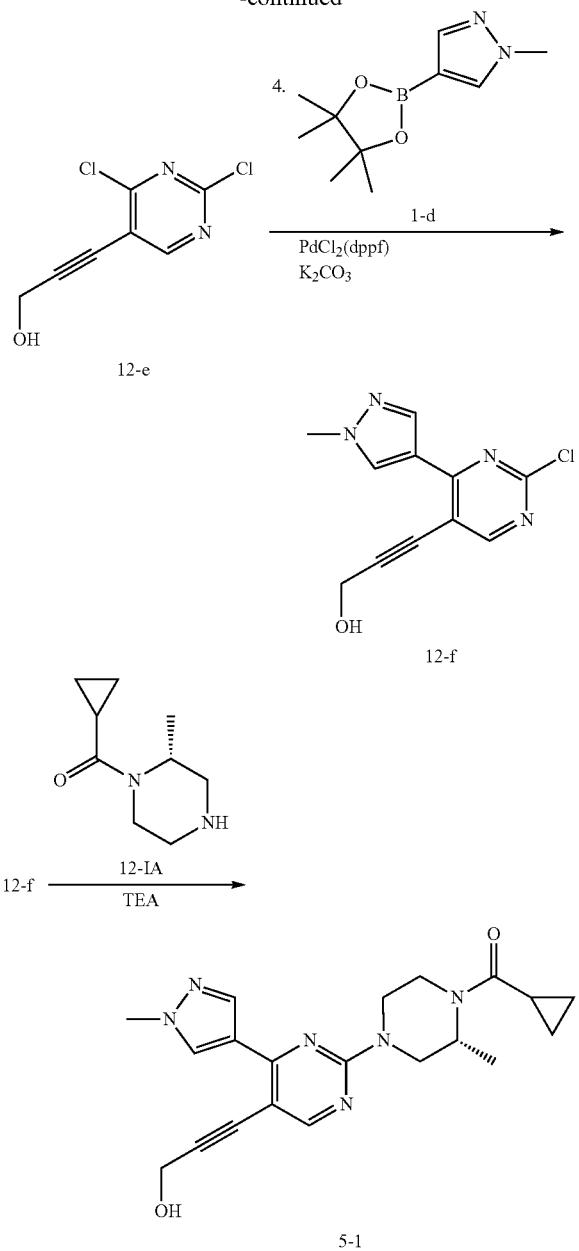

Step 1 (R)-tert-butyl 4-(cyclopropanecarbonyl)-3-methylpiperazine-1-carboxylate (12-c)

To a solution of (R)-tert-butyl 3-methylpiperazine-1-carboxylate (12-a) (15 g, 75 mmol) and TEA (31.2 ml, 225 mmol) in DCM (200 ml) was added cyclopropanecarbonyl chloride (12-b) (8.2 ml, 90 mmol) dropwise at 0° C., after which the solution was stirred at RT for 2 h. The mixture was then concentrated in vacuo to give a residue, which was diluted with DCM and adsorbed onto silica gel (100-200 mesh). Purification by flash column chromatography (silica gel, eluting with 20%-25% EtOAc in Hexanes) gave (R)-tert-butyl 4-(cyclopropanecarbonyl)-3-methylpiperazine-1-carboxylate (12-c). Calc'd for ($C_{10}H_{17}N_2O_3$) [M+H-tBu]$^+$, 213; found, 213.

Step 2 Intermediate 12-IA

To a solution of (R)-tert-butyl 4-(cyclopropanecarbonyl)-3-methylpiperazine-1-carboxylate (12-c) (16 g, 60 mmol) in DCM (50 ml) was added TFA (7.97 ml, 107 mmol) at RT. The resulting mixture was stirred for 4 h at RT. The residue was then diluted with DCM (50 mL), and the organic layer was washed with saturated aqueous sodium bicarbonate (3×100 mL), dried over anhydrous sodium sulfate, and filtered. The filtrate was concentrated under reduced pressure, and the residue was purified by column chromatography (silica gel, using a gradient of 85 to 95% EtOAc in hexanes as eluent) to afford Intermediate 12-IA. Calc'd for ($C_9H_{17}N_2O$) [M+H]$^+$, 169; found, 169.

Step 3 3-(2,4-dichloropyrimidin-5-yl)prop-2-yn-1-ol (12-e)

To a solution of 2,4-dichloro-5-iodopyrimidine (12-d) (1.0 g, 3.64 mmol) and 3-(trimethylsilyl)prop-2-yn-1-ol (0.51 g, 4.0 mmol) in DMF (20 ml) were added Pd(PPh$_3$)$_2$Cl$_2$ (0.26 g, 0.36 mmol), tetra-N-butyl ammonium fluoride (0.951 g, 3.64 mmol), CuI (0.21 g, 1.09 mmol) and TEA (0.74 g, 7.28 mmol) at RT. The resulting solution was stirred for 2 h at 50° C., after which the reaction mixture was quenched with water (10 mL). The mixture was then extracted with EtOAc (3×20 mL), and the combined organic layers were washed with brine (6×5 mL), dried over anhydrous sodium sulfate, and filtered. The filtrate was concentrated under reduced pressure, and the residue was purified by column chromatography (silica gel column, eluting with 0-5% ethyl acetate in petroleum ether) to afford 3-(2,4-dichloropyrimidin-5-yl)prop-2-yn-1-ol (12-e).

Step 4 3-(2-chloro-4-(1-methyl-1H-pyrazol-4-yl)pyrimidin-5-yl)prop-2-yn-1-ol (12-f)

To a solution of 3-(2,4-dichloropyrimidin-5-yl)prop-2-yn-1-ol (12-e) (300 mg, 1.5 mmol) in 1,4-dioxane (5 ml) and water (0.5 ml) were added 1-methyl-4-(4,4,5,5-tetramethyl-1,3,2-dioxaborolan-2-yl)-1H-pyrazole (1-d) (369 mg, 1.77 mmol) [1,1'-Bis (diphenylphosphino)ferrocene]dichloropalladium(II) (54 mg, 0.074 mmol) and potassium carbonate (408 mg, 2.96 mmol). The solution was stirred for 24 h at 90° C. under nitrogen (1 atm), after which the mixture was quenched with water (10 mL) and extracted with DCM (3×10 mL). The combined organic layers were dried over anhydrous sodium sulfate and filtered. The filtrate was then concentrated under vacuum to give a residue, which was purified by preparatory TLC (eluting with DCM:MeOH=30:1) to afford 3-(2-chloro-4-(1-methyl-H-pyrazol-4-yl)pyrimidin-5-yl)prop-2-yn-1-ol (12-f). MS (ESI) Calc'd for ($C_{11}H_{10}ClN_4O$) [M+H]$^+$, 249; found, 249.

Step 5 3-{2-[(3R)-4-(cyclopropylcarbonyl)-3-methylpiperazin-1-yl]-4-(1-methyl-1H-pyrazol-4-yl)pyrimidin-5-yl}prop-2-yn-1-ol (5-1)

To a solution of 3-(2-chloro-4-(1-methyl-H-pyrazol-4-yl)pyrimidin-5-yl)prop-2-yn-1-ol (12-f) (50 mg, 0.20 mmol) and TEA (52.0 mg, 0.40 mmol) in 2-propanol (2 ml) was added Intermediate 12-IA (51 mg, 0.30 mmol) at RT. The resulting solution was stirred for 5 h at 80° C., after which the reaction mixture was quenched with water (2 mL). The mixture was then extracted with EtOAc (3×5 mL), and the combined organic layers were dried over anhydrous sodium sulfate and filtered. The filtrate was concentrated under reduced pressure, and the residue was purified by column chromatography (silica gel column, eluting with 50% EtOAc in Hexanes) to afford compound 5-1. MS (ESI) Calc'd for ($C_{20}H_{25}N_6O_2$) [M+H]$^+$, 381, found, 381.

Example 13

2-[(3R)-4-(cyclopropylcarbonyl)-3-methylpiperazin-1-yl]-6-(1-methyl-1H-pyrazol-4-yl)pyrimidine-4-carbonitrile (5-2)

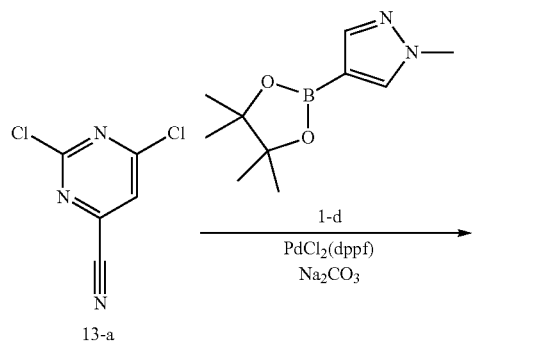

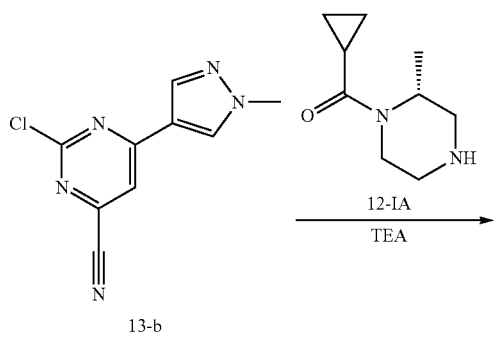

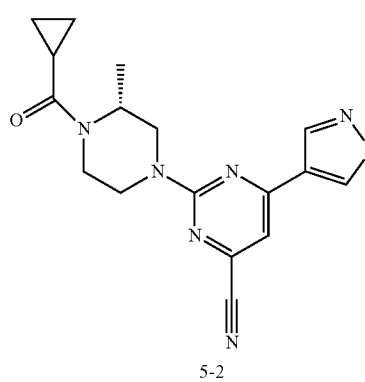

Step 1 2-chloro-6-(1-methyl-1H-pyrazol-4-yl)pyrimidine-4-carbonitrile (13-b)

To a stirred solution of 2,6-dichloropyrimidine-4-carbonitrile (13-a) (200 mg, 1.15 mmol) in 1,4-dioxane (4 ml) were added Na$_2$CO$_3$ (244 mg, 2.30 mmol), PdCl$_2$(dppf) (84 mg, 0.12 mmol) and 1-methyl-4-(4,4,5,5-tetramethyl-1,3,2-dioxaborolan-2-yl)-1H-pyrazole (1-d) (215 mg, 1.04 mmol). The solution was stirred for 10 h at 90° C. under the nitrogen atmosphere (1 atm). The solution was then cooled to RT, after which the solution was diluted with DCM (100 mL). The solution was extracted with water (3×50 mL), washed with brine (3×30 mL), dried over anhydrous sodium sulfate, and filtered. The filtrate was concentrated in vacuo, and the residue was purified by column chromatography (silica gel, eluting with ethyl acetate:petroleum ether (1:1 v/v)) to give 2-chloro-6-(1-methyl-H-pyrazol-4-yl)pyrimidine-4-carbonitrile (13-b). MS (ESI) Calc'd for ($C_9H_7ClN_5$) [M+H]$^+$, 220, found, 220.

Step 2 (R)-2-(4-(cyclopropanecarbonyl)-3-methylpiperazin-1-yl)-6-(1-methyl-1H-pyrazol-4-yl)pyrimidine-4-carbonitrile (5-2)

To a stirred solution of 2-chloro-6-(1-methyl-H-pyrazol-4-yl)pyrimidine-4-carbonitrile (13-b)(35 mg, 0.16 mmol) in EtOH (2 ml) was added TEA (0.067 ml, 0.48 mmol). (R)-cyclopropyl(2-methylpiperazin-1-yl)methanone (12-IA) (32.2 mg, 0.191 mmol) was added into the solution dropwise at 0° C. The solution was then allowed to come to RT and was stirred for 10 h. The solution was then quenched with the addition of water (70 mL), and the resulting mixture was extracted with DCM (3×100 mL). The combined organic layers were washed with brine (3×50 mL) and filtered. The filtrate was concentrated in vacuo, and the residue was purified by column chromatography (silica gel, eluting with EtOAc) to give the crude product. The crude product was further purified by revers-phase, preparatory HPLC (Xbridge RP18, 5 um, 19×150 mm (Waters Corporation, Milford, Mass., USA); eluting with 10-61% MeCN in water (0.05% ammonium bicarbonate) to give (R)-2-(4-(cyclopropanecarbonyl)-3-methylpiperazin-1-yl)-6-(1-methyl-1H-pyrazol-4-yl)pyrimidine-4-carbonitrile (5-2). H NMR (500 MHz, DMSO-d6) δ 8.52 (s, 1H), 8.18 (s, 1H), 7.50 (s, 1H), 4.08-4.76 (m, 4H), 3.90 (s, 3H), 2.90-3.58 (m, 3H), 1.98 (s, 1H), 0.89-1.32 (m, 3H), 0.74 (br s, 4H). MS (ESI) Calc'd for ($C_{18}H_{22}N_7O$) [M+H]$^+$, 352, found, 352.

Example 14

6-[(3R)-4-(cyclopropylcarbonyl)-3-methylpiperazin-1-yl]-2-(1-methyl-1H-pyrazol-4-yl)pyrimidine-4-carbonitrile (5-3)

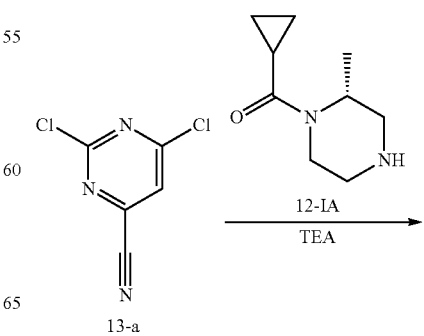

-continued

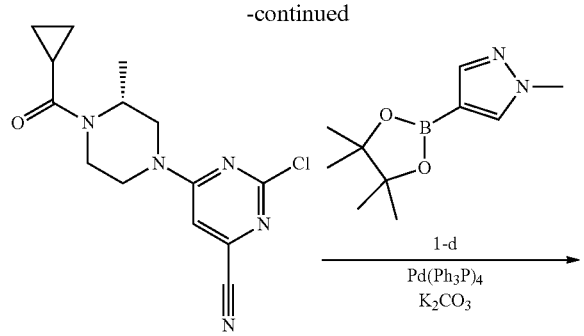

Step 1 (R)-2-chloro-6-(4-(cyclopropanecarbonyl)-3-methylpiperazin-1-yl)pyrimidine-4-carbonitrile (14-a)

To a stirred solution of 2,6-dichloropyrimidine-4-carbonitrile (13-a) (300 mg, 1.724 mmol) and TEA (0.721 ml, 5.17 mmol) in EtOH (5 ml) was added (R)-cyclopropyl(2-methylpiperazin-1-yl)methanone (12-IA) (435 mg, 2.59 mmol) at 0° C. The solution was stirred for 2 h at RT, after which the solution was concentrated in vacuo. The residue was dissolved in DCM (100 mL), and the solution was extracted with water (3×50 mL). The organic layer was washed with brine (2×50 mL), dried over anhydrous sodium sulfate, and filtered. The filtrate was concentrated in vacuo, and the residue was purified by column chromatography (silica gel, eluting with EtOAc/petroleum ether (1:1)) to give (R)-2-chloro-6-(4-(cyclopropanecarbonyl)-3-methylpiperazin-1-yl)pyrimidine-4-carbonitrile (14-a). MS (ESI) Calc'd for $(C_{14}H_{17}ClN_5O)$ $[M+H]^+$, 306, found, 306.

Step 2 6-[(3R)-4-(cyclopropylcarbonyl)-3-methylpiperazin-1-yl]-2-(1-methyl-1H-pyrazol-4-yl)pyrimidine-4-carbonitrile (5-3)

To a stirred solution of (R)-2-chloro-6-(4-(cyclopropanecarbonyl)-3-methylpiperazin-1-yl)pyrimidine-4-carbonitrile (14-a) (50 mg, 0.164 mmol) in 1,4-dioxane (3 ml) and water (0.6 ml) were added potassium carbonate (45.2 mg, 0.33 mmol), Pd(Ph₃P)₄ (9.45 mg, 8.18 μmol) and 1-methyl-4-(4,4,5,5-tetramethyl-1,3,2-dioxaborolan-2-yl)-1H-pyrazole (1-d) (40.8 mg, 0.20 mmol). The solution was stirred for 3 h at 90° C. under the nitrogen atmosphere. The solution was then cooled RT and was diluted with EtOAc (100 mL). The solution was then extracted with water (3×50 mL), and the organic layer was washed with brine (3×50 mL), dried over anhydrous sodium sulfate, and filtered. The filtrate was concentrated in vacuo, and the residue was purified by column chromatography (silica gel, eluting with EtOAc/petroleum ether (10:1) to give the crude product. The crude product was purified by reverse-phase, preparatory HPLC (Xbridge RP18, 5 um, 19×150 mm (Waters Corporation, Milford, Mass., USA); eluting with 10-51% MeCN in water (0.05% ammonium bicarbonate) to give compound 5-3. ¹H NMR (500 MHz, DMSO-d6) δ 8.37 (s, 1H), 7.98 (s, 1H), 7.36 (s, 1H), 4.42-4.89 (m, 2H), 3.71-4.30 (m, 4H), 2.87-3.62 (m, 4H), 2.00 (s, 1H), 0.92-1.33 (m, 3H), 0.74 (br s, 4H). MS (ESI) Calc'd for $(C_{18}H_{22}N_7O)$ $[M+H]^+$, 352, found, 352.

Example 15

(R)-2-(4-(cyclopropanecarbonyl)-3-methylpiperazin-1-yl)-4-(1-methyl-1H-pyrazol-4-yl)pyrimidine-5-carbonitrile (5-4)

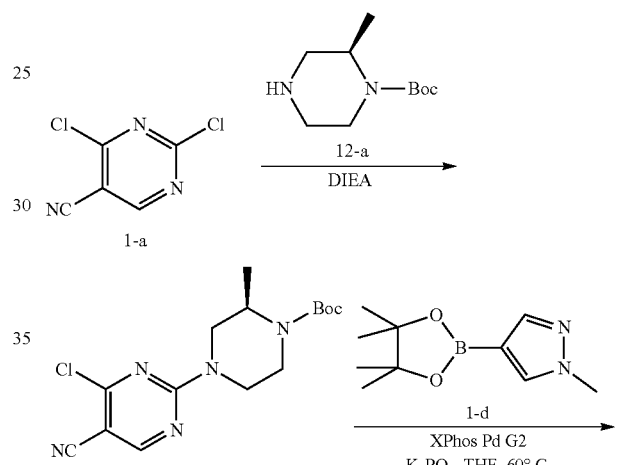

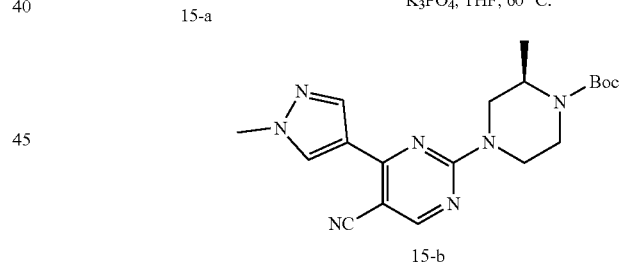

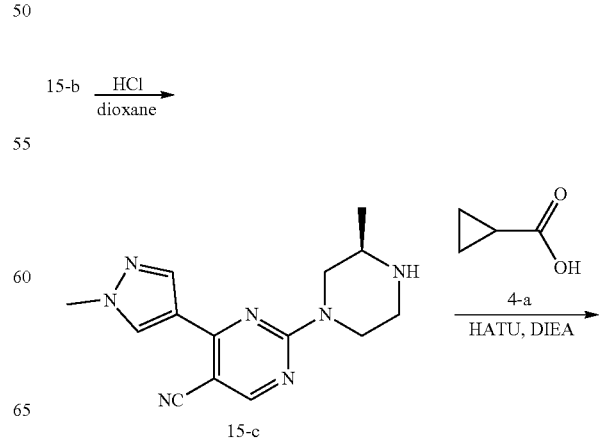

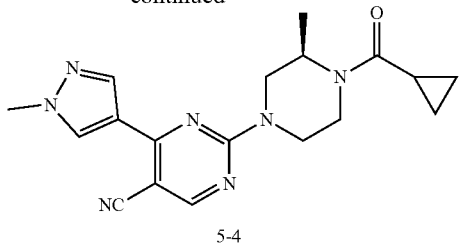

5-4

Step 1 tert-butyl (R)-4-(4-chloro-5-cyanopyrimidin-2-yl)-2-methylpiperazine-1-carboxylate (15-a)

To a flask were added 2,4-dichloropyrimidine-5-carbonitrile (1-a) (3.0 g, 17.24 mmol), (R)-tert-butyl 2-methylpiperazine-1-carboxylate (12-a) (3.3 g, 16.5 mmol), DMF (100 ml) and DIEA (8 ml, 46 mmol). The mixture was stirred at RT for 2 h. To the resulting mixture were added EtOAc and water, and the organic phase was separated and concentrated in vacuo to afford tert-butyl (R)-4-(4-chloro-5-cyanopyrimidin-2-yl)-2-methylpiperazine-1-carboxylate, (15-a) which was used in next step without further purification. MS (ESI) Calc'd for $C_{15}H_{21}ClN_5O_2$ [M+1]$^+$, 338; found, 338.

Step 2 tert-butyl (R)-4-(5-cyano-4-(1-methyl-1H-pyrazol-4-yl)pyrimidin-2-yl)-2-methylpiperazine-1-carboxylate (15-b)

To a flask were added (R)-tert-butyl 4-(4-chloro-5-cyanopyrimidin-2-yl)-2-methylpiperazine-1-carboxylate (15-a) (5.82 g, 17.23 mmol), 1-methyl-4-(4,4,5,5-tetramethyl-1,3,2-dioxaborolan-2-yl)-1H-pyrazole (1-d) (5.91 g, 28.4 mmol), XPhos Pd G2 (668 mg, 0.849 mmol), THF (100 ml) and potassium phosphate ($K_3PO_4$) (35 ml, 42 mmol). The mixture was evacuated and back-filled with nitrogen (×6), after which the reaction vessel was heated at 60° C. for 16 h. The mixture was then cooled, filtered, and concentrated in vacuo to afford a residue which was purified by column chromatography on silica gel (silica gel, eluting with a gradient of 0-40% EtOAc in hexanes) to afford (R)-tert-butyl 4-(5-cyano-4-(1-methyl-1H-pyrazol-4-yl)pyrimidin-2-yl)-2-methylpiperazine-1-carboxylate (15-b). MS (ESI) Calc'd for $C_{19}H_{26}N_7O_2$ [M+1]$^+$, 384; found, 384.

Step 3 (R)-4-(1-methyl-1H-pyrazol-4-yl)-2-(3-methylpiperazin-1-yl)pyrimidine-5-carbonitrile (15-c)

To the solution of (R)-tert-butyl 4-(5-cyano-4-(1-methyl-H-pyrazol-4-yl)pyrimidin-2-yl)-2-methylpiperazine-1-carboxylate (15-b) (3.05 g, 7.95 mmol) in dioxane (14 ml), was added HCl in dioxane (10.5 ml, 42.0 mmol, 4M). The mixture was stirred at RT for 18 h, after which the solvent was removed in vacuo to afford the crude product as the HCl salt. The product was then free-based to afford (R)-4-(1-methyl-H-pyrazol-4-yl)-2-(3-methylpiperazin-1-yl)pyrimidine-5-carbonitrile (15-c). MS (ESI) Calc'd for $C_{14}H_{18}N_7$ [M+1]$^+$, 284; found, 284.

Step 4 (R)-2-(4-(cyclopropanecarbonyl)-3-methylpiperazin-1-yl)-4-(1-methyl-1H-pyrazol-4-yl)pyrimidine-5-carbonitrile (5-4)

To the vial were added (R)-4-(1-methyl-1H-pyrazol-4-yl)-2-(3-methylpiperazin-1-yl)pyrimidine-5-carbonitrile (15-c) (105 mg, 0.371 mmol), HATU (141 mg, 0.371 mmol), DMF (3.0 mL), cyclopropanecarboxylic acid (4-a)(46 mg, 0.53 mmol) and DIEA (500 µl, 2.9 mmol). The mixture was then stirred at RT for 16 h. The reaction mixture was then filtered and purified by preparative, reverse-phase HPLC (ACN/water with 0.1% TFA) to afford compound 5-4 as the TFA salt. $^1$H NMR (600 MHz, Methanol-d$_4$) δ 8.57 (s, 1H), 8.50 (s, 1H), 8.30 (s, 1H), 4.88-4.54 (m, 3H), 4.44-4.15 (m, 1H), 3.96 (s, 3H), 3.70-3.39 (m, 2H), 3.34-3.06 (m, 1H), 2.07-1.90 (m, 1H), 1.45-1.04 (m, 3H), 0.98-0.75 (m, 4H). MS (ESI) Calc'd for $C_{18}H_{22}N_7O$ [M+1]$^+$, 352; found, 352.

Example 16

2-[(3R)-4-(cyclopropylcarbonyl)-3-methylpiperazin-1-yl]-5-[5-(1-methylethyl)-1,3-oxazol-2-yl]-4-(1-methyl-1H-pyrazol-4-yl)pyrimidine (5-5)

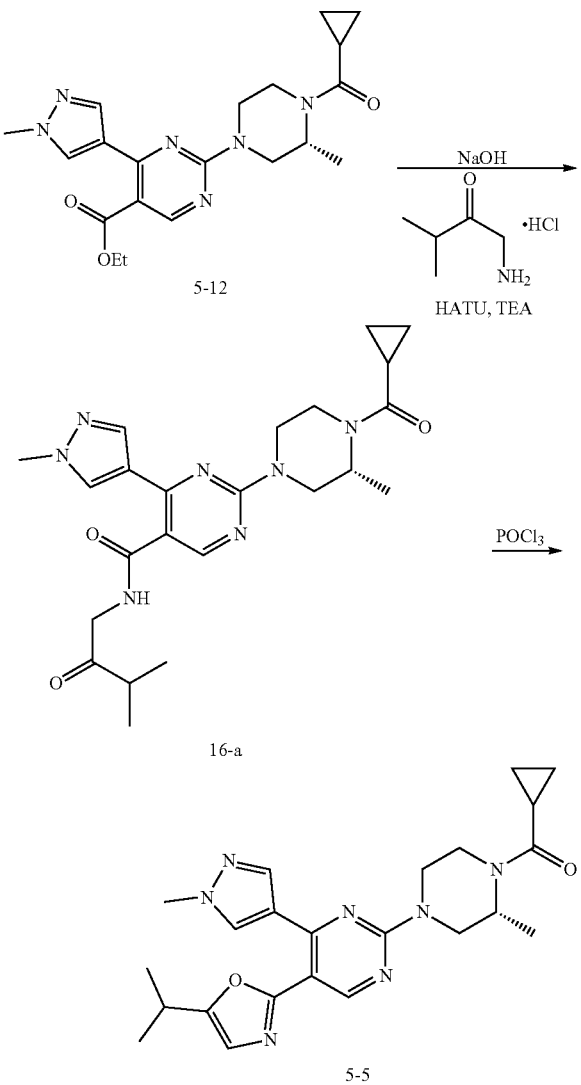

Step 1 (R)-2-(4-(cyclopropanecarbonyl)-3-methylpiperazin-1-yl)-4-(1-methyl-1H-pyrazol-4-yl)pyrimidine-5-carboxylic acid (16-Ia)

To a solution of compound 5-12 (250 mg, 0.627 mmol) in EtOH (5 ml), were added Water (1 ml) and NaOH (25.1 mg, 0.627 mmol) at RT. The resulting mixture was stirred at RT for 12 h, after which the reaction mixture was diluted with water (20 mL) and the pH was adjusted to pH=3 with the addition of aqueous HCl (1M). The resulting mixture was extracted with EtOAc (3×20 mL), and the combined organic layers were washed with brine (20 mL), dried over anhydrous sodium sulfate, and filtered. The filtrate was concentrated under reduced pressure to afford (R)-2-(4-(cyclopropanecarbonyl)-3-methylpiperazin-1-yl)-4-(1-methyl-1H-pyrazol-4-yl)pyrimidine-5-carboxylic acid (16-IA), which was used directly in the next step without further purification. MS (ESI) Calc'd for ($C_{18}H_{23}N_6O_3$) [M+H]$^+$, 371; found, 371.

Step 2 (R)-2-(4-(cyclopropanecarbonyl)-3-methylpiperazin-1-yl)-4-(1-methyl-1H-pyrazol-4-yl)-N-(3-methyl-2-oxobutyl)pyrimidine-5-carboxamide (16-a)

To a solution of (R)-2-(4-(cyclopropanecarbonyl)-3-methylpiperazin-1-yl)-4-(1-methyl-1H-pyrazol-4-yl)pyrimidine-5-carboxylic acid (16-IA) (200 mg, 0.54 mmol) in DMF (5 ml), were added HATU (246 mg, 0.65 mmol), TEA (0.19 ml, 1.35 mmol), and 1-amino-3-methylbutan-2-one hydrochloride (89 mg, 0.65 mmol) at RT. The resulting mixture was stirred at RT for 1 h, after which the reaction mixture was quenched with sat. aqueous NH$_4$Cl (20 mL). The resulting mixture was extracted with EtOAc (3×20 mL), and the combined organic layers were washed with brine (20 mL), dried over anhydrous sodium sulfate and filtered. The filtrate was concentrated under reduced pressure, and the residue was purified by column chromatography (silica gel, eluting with a gradient of 0-5% MeOH in DCM) to afford (R)-2-(4-(cyclopropanecarbonyl)-3-methylpiperazin-1-yl)-4-(1-methyl-1H-pyrazol-4-yl)-N-(3-methyl-2-oxobutyl)pyrimidine-5-carboxamide (16-a). MS (ESI) Calc'd for ($C_{23}H_{32}N_7O_3$) [M+H]$^+$, 454; found, 454.

Step 3 2-[(3R)-4-(cyclopropylcarbonyl)-3-methylpiperazin-1-yl]-5-[5-(1-methylethyl)-1,3-oxazol-2-yl]-4-(1-methyl-1H-pyrazol-4-yl)pyrimidine (5-5)

To a solution of (R)-2-(4-(cyclopropanecarbonyl)-3-methylpiperazin-1-yl)-4-(1-methyl-1H-pyrazol-4-yl)-N-(3-methyl-2-oxobutyl)pyrimidine-5-carboxamide (16-a) (90 mg, 0.20 mmol) in DMF (2 ml), was added POCl$_3$ (0.06 ml, 0.60 mmol) at RT. The resulting mixture was stirred at 100° C. for 15 min, after which the reaction mixture was quenched with sat. aqueous NH$_4$C (20 mL). The resulting mixture was extracted with EtOAc (3×20 mL), and the combined organic layers were washed with brine (20 mL), dried over anhydrous sodium sulfate, and filtered. The filtrate was concentrated under reduced pressure, and the residue was purified by column chromatography (silica gel, eluting with a gradient of 0-5% MeOH in DCM) to afford 2-[(3R)-4-(cyclopropylcarbonyl)-3-methylpiperazin-1-yl]-5-[5-(1-methylethyl)-1,3-oxazol-2-yl]-4-(1-methyl-1H-pyrazol-4-yl)pyrimidine (5-5). $^1$H NMR (500 MHz, DMSO-d6) δ 8.57 (s, 1H), 8.11 (s, 1H), 7.47 (s, 1H), 7.05 (s, 1H), 4.46-4.77 (m, 3H), 4.23 (br s, 1H), 3.87 (s, 3H), 2.93-3.55 (m, 4H), 2.01 (s, 1H), 0.96-1.33 (m, 9H), 0.76 (br s, 4H). MS (ESI) Calc'd for ($C_{23}H_{30}N_7O_2$) [M+H]$^+$, 436, found, 436.

Example 17

(R)-4-(4-(cyclopropanecarbonyl)-3-isobutylpiperazin-1-yl)-2-(1-methyl-1H-pyrazol-4-yl)pyrimidine-5-carbonitrile (5-6)

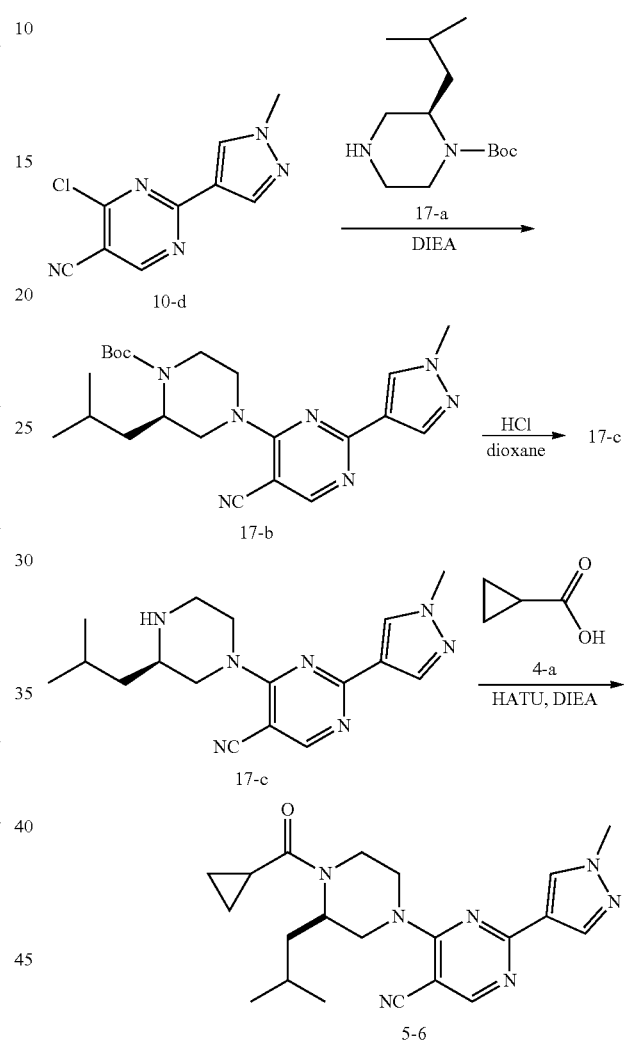

Step 1 tert-butyl (R)-4-(5-cyano-2-(1-methyl-1H-pyrazol-4-yl)pyrimidin-4-yl)-2-isobutylpiperazine-1-carboxylate (17-b)

To a vial containing (R)-tert-butyl 2-isobutylpiperazine-1-carboxylate (17-a) (50.8 mg, 0.210 mmol, commerically available from Matrix Scientific, Cairo, Egypt), were added compound 10-d (48.3 mg, 0.220 mmol), DMF (2.0 mL) and DIEA (100 μl, 0.57 mmol). The mixture was stirred at RT for 19 h. The mixture was then filtered and purified by preparative, reverse-phase HPLC (eluting with ACN/water with 0.1% TFA) to afford (R)-tert-butyl 4-(5-cyano-2-(1-methyl-1H-pyrazol-4-yl)pyrimidin-4-yl)-2-isobutylpiperazine-1-carboxylate (17-b) as the TFA salt. MS (ESI) Calc'd for $C_{22}H_{32}N_7O_2$ [M+1]$^+$, 426; found, 426.

Step 2 (R)-4-(3-isobutylpiperazin-1-yl)-2-(1-methyl-1H-pyrazol-4-yl)pyrimidine-5-carbonitrile (17-c)

To a vial containing (R)-tert-butyl 4-(5-cyano-2-(1-methyl-1H-pyrazol-4-yl)pyrimidin-4-yl)-2-isobutylpiperazine-1-carboxylate (17-b) (29.2 mg, 0.054 mmol), were added dioxane (500 µl) and HCl in dioxane (400 µl, 1.600 mmol, 4M). The mixture was stirred at rt for 16 h, after which the solvent was removed in vacuo to afford the product (17-c) as HCl salt, which was used in next step without further purification. MS (ESI) Calc'd for $C_{17}H_{24}N_7$ [M+1]$^+$, 326; found, 326.

Step 3 (R)-4-(4-(cyclopropanecarbonyl)-3-isobutylpiperazin-1-yl)-2-(1-methyl-1H-pyrazol-4-ylpyrimidine-5-carbonitrile (5-6)

To a vial were added (R)-4-(3-isobutylpiperazin-1-yl)-2-(1-methyl-H-pyrazol-4-yl)pyrimidine-5-carbonitrile (17-c), HCl (20 mg, 0.055 mmol), HATU (25.2 mg, 0.066 mmol), DMF (553 µl), DIEA (60 µl, 0.344 mmol), and cyclopropanecarboxylic acid (4-a) (24 mg, 0.279 mmol). The mixture was stirred at rt for 16 h, after which the mixture was filtered and purified by preparative, reverse-phase HPLC (eluting with ACN/water, 0.1% TFA) to afford compound 5-6 as the TFA salt. $^1$H NMR (600 MHz, DMSO-$d_6$) δ 8.63 (s, 1H), 8.37 (s, 1H), 7.99 (s, 1H), 4.83-4.43 (m, 2H), 4.34-4.12 (m, 1H), 3.87 (s, 3H), 3.63-3.40 (m, 1H), 3.39-3.24 (m, 1H), 3.24-3.08 (m, 1H), 3.06-2.90 (m, 1H), 2.02-1.89 (m, 1H), 1.64-1.17 (m, 3H), 1.02-0.52 (m, 10H). MS (ESI) Calc'd for $C_{21}H_{28}N_7O$ [M+1]$^+$, 394; found, 394.

Compound 5-7 found in Table 5, was prepared in a manner analogous to Example 17, except that (S)-tert-butyl 2-(hydroxymethyl)piperazine-1-carboxylate was used in place of (R)-tert-butyl 2-isobutylpiperazine-1-carboxylate.

Compound 5-8 found in Table 5, was prepared in a manner analogous to Example 15, except that 3-methylbut-1-yne was used in place of 3-(trimethylsilyl)prop-2-yn-1-ol and TBAF was not added to the reaction mixture.

Compound 5-9 found in Table 5, was prepared in a manner analogous to Example 15, except that ethynyltrimethylsilane was used in place of 3-(trimethylsilyl)prop-2-yn-1-ol and the final product was obtained following a standard deprotection using TBAF.

Compounds 5-10 and 5-11, found in Table 5, were prepared in a manner analogous to Example 16, except that 2,4-dichloro-5-(methylthio)pyrimidine, 2,4-dichloro-5-(difluoromethyl)-pyridmidine (commercially available from FCH Group), and 2,6-dichloroisonicotinonitrile were used in place of 2,6-dichloropyrimidine-4-carbonitrile, respectively, in Step 1 and potassium carbonate was used in place of sodium carbonate in Step 2.

Compound 5-12 found in Table 5, was prepared in a manner analogous to Example 12, except that ethyl 2,4-dichloropyrimidine-5-carboxylate was used in place of 2,6-dichloropyrimidine-4-carbonitrile and potassium carbonate was used in place of sodium carbonate in Step 1.

Compound 5-13 found in Table 5, was prepared in a manner analogous to Example 16, except that 2,4,5-trichloropyrimidine was used in place of 2,6-dichloropyrimidine-4-carbonitrile in Step 1 and potassium carbonate and tetrakis (triphenylphosphine)palladium(O) were used in place of sodium carbonate and [1,1-Bis (diphenylphosphino)ferrocene]dichloropalladium(II) in Step 2.

TABLE 5

| Compound | Structure | Name | Exact Mass [M + H]+ |
|---|---|---|---|
| 5-1 | 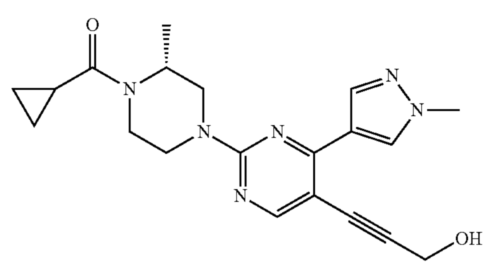 [SMILES: C[C@@H]1CN(c2ncc(C#CCO)c(-c3cnn(C)c3)n2)CCN1C(=O)C1CC1] | 3-{2-[(3R)-4-(cyclopropylcarbonyl)-3-methylpiperazin-1-yl]-4-(1-methyl-1H-pyrazol-4-yl)pyrimidin-5-yl}prop-2-yn-1-ol | Calc'd 381, found |
| 5-2 | 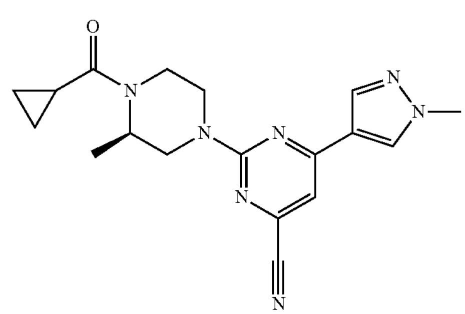 [SMILES: C[C@@H]1CN(c2nc(C#N)cc(-c3cnn(C)c3)n2)CCN1C(=O)C1CC1] | 2-[(3R)-4-(cyclopropylcarbonyl)-3-methylpiperazin-1-yl]-6-(1-methyl-1H-pyrazol-4-yl)pyrimidine-4-carbonitrile | Calc'd 352, found |

TABLE 5-continued

| Compound | Structure | Name | Exact Mass [M + H]+ |
|---|---|---|---|
| 5-3 | 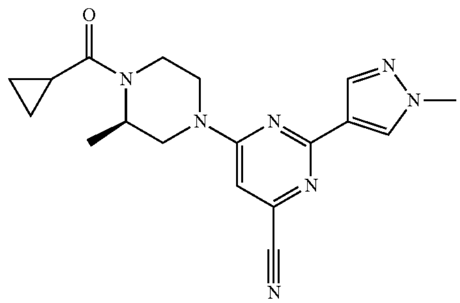 [SMILES: C[C@@H]1CN(c2cc(C#N)nc(-c3cnn(C)c3)n2)CCN1C(=O)C1CC1] | 6-[(3R)-4-(cyclopropylcarbonyl)-3-methylpiperazin-1-yl]-2-(1-methyl-1H-pyrazol-4-yl)pyrimidine-4-carbonitrile | Calc'd 352, found |
| 5-4 | 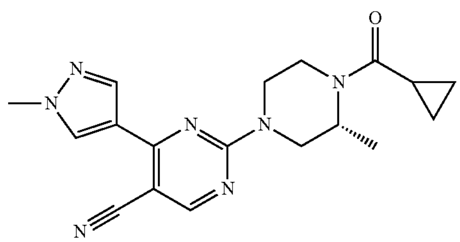 [SMILES: C[C@@H]1CN(c2ncc(C#N)c(-c3cnn(C)c3)n2)CCN1C(=O)C1CC1] | 2-[(3R)-4-(cyclopropylcarbonyl)-3-methylpiperazin-1-yl]-4-(1-methyl-1H-pyrazol-4-yl)pyrimidine-5-carbonitrile | Calc'd 352, found |
| 5-5 | 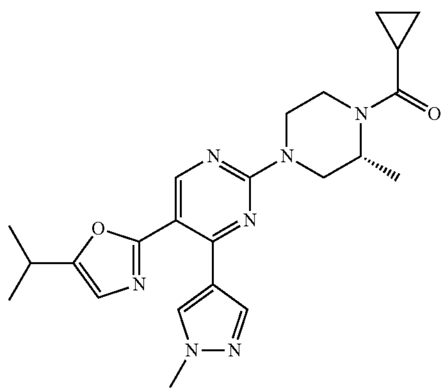 [SMILES: CC(C)c1cnc(-c2cnc(N3CCN(C(=O)C4CC4)[C@H](C)C3)nc2-c2cnn(C)c2)o1] | 2-[(3R)-4-(cyclopropylcarbonyl)-3-methylpiperazin-1-yl]-5-[5-(1-methylethyl)-1,3-oxazol-2-yl]-4-(1-methyl-1H-pyrazol-4-yl)pyrimidine | Calc'd 436, found |
| 5-6 | 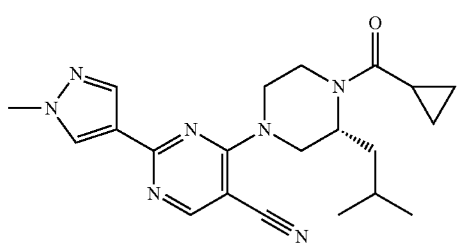 [SMILES: CC(C)C[C@@H]1CN(c2nc(-c3cnn(C)c3)ncc2C#N)CCN1C(=O)C1CC1] | 4-[(3R)-4-(cyclopropylcarbonyl)-3-(2-methylpropyl)piperazin-1-yl]-2-(1-methyl-1H-pyrazol-4-yl)pyrimidine-5-carbonitrile | Calc'd 394, found |
| 5-7 | 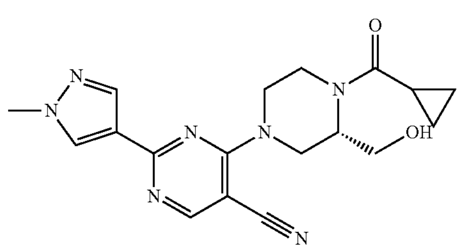 [SMILES: Cn1cc(-c2ncc(C#N)c(N3CCN(C(=O)C4CC4)[C@H](CO)C3)n2)cn1] | 4-[(3S)-4-(cyclopropylcarbonyl)-3-(hydroxymethyl)piperazin-1-yl]-2-(1-methyl-1H-pyrazol-4-yl)pyrimidine-5-carbonitrile | Calc'd 368, found |

TABLE 5-continued

| Compound | Structure | Name | Exact Mass [M + H]+ |
|---|---|---|---|
| 5-8 | 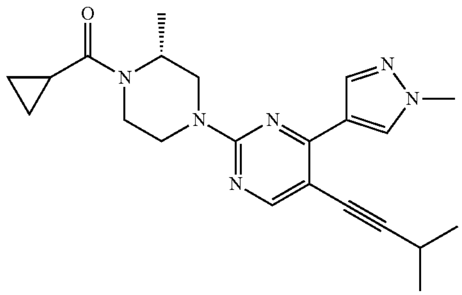 [SMILES: CC(C)C#Cc1cnc(N2CCN(C(=O)C3CC3)[C@H](C)C2)nc1-c1cnn(C)c1] | 2-[(3R)-4-(cyclopropylcarbonyl)-3-methylpiperazin-1-yl]-5-(3-methylbut-1-yn-1-yl)-4-(1-methyl-1H-pyrazol-4-yl)pyrimidine | Calc'd 393, found |
| 5-9 | 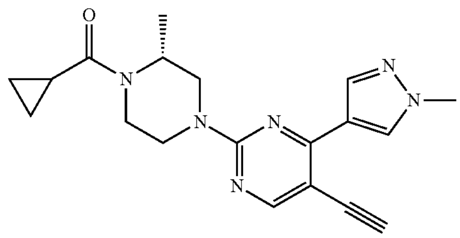 [SMILES: C#Cc1cnc(N2CCN(C(=O)C3CC3)[C@H](C)C2)nc1-c1cnn(C)c1] | 2-[(3R)-4-(cyclopropylcarbonyl)-3-methylpiperazin-1-yl]-5-ethynyl-4-(1-methyl-1H-pyrazol-4-yl)pyrimidine | Calc'd 351, found |
| 5-10 | 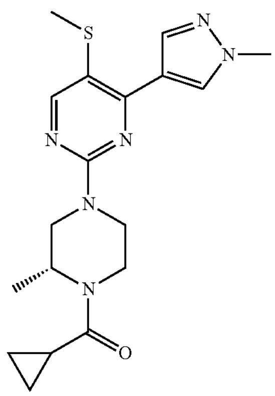 [SMILES: CSc1cnc(N2CCN(C(=O)C3CC3)[C@H](C)C2)nc1-c1cnn(C)c1] | 2-[(3R)-4-(cyclopropylcarbonyl)-3-methylpiperazin-1-yl]-4-(1-methyl-1H-pyrazol-4-yl)-5-(methylsulfanyl)pyrimidine | Calc'd 373, found |
| 5-11 | 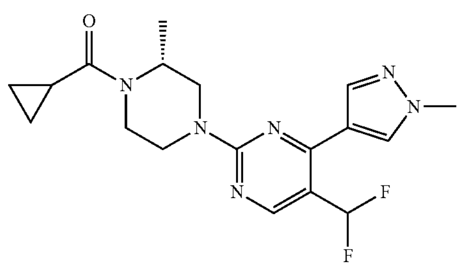 [SMILES: C[C@@H]1CN(c2ncc(C(F)F)c(-c3cnn(C)c3)n2)CCN1C(=O)C1CC1] | 2-[(3R)-4-(cyclopropylcarbonyl)-3-methylpiperazin-1-yl]-5-(difluoromethyl)-4-(1-methyl-1H-pyrazol-4-yl)pyrimidine | Calc'd 377, found |
| 5-12 | 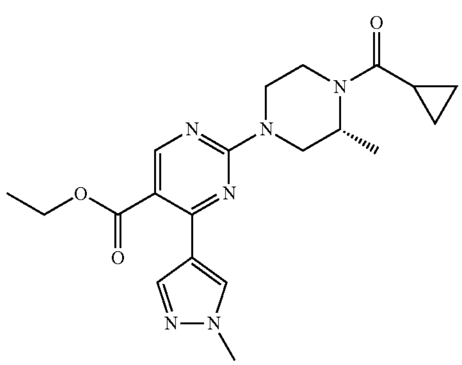 [SMILES: CCOC(=O)c1cnc(N2CCN(C(=O)C3CC3)[C@H](C)C2)nc1-c1cnn(C)c1] | ethyl 2-[(3R)-4-(cyclopropylcarbonyl)-3-methylpiperazin-1-yl]-4-(1-methyl-1H-pyrazol-4-yl)pyrimidine-5-carboxylate | Calc'd 399, found |

TABLE 5-continued

| Compound | Structure | Name | Exact Mass [M + H]+ |
|---|---|---|---|
| 5-13 | 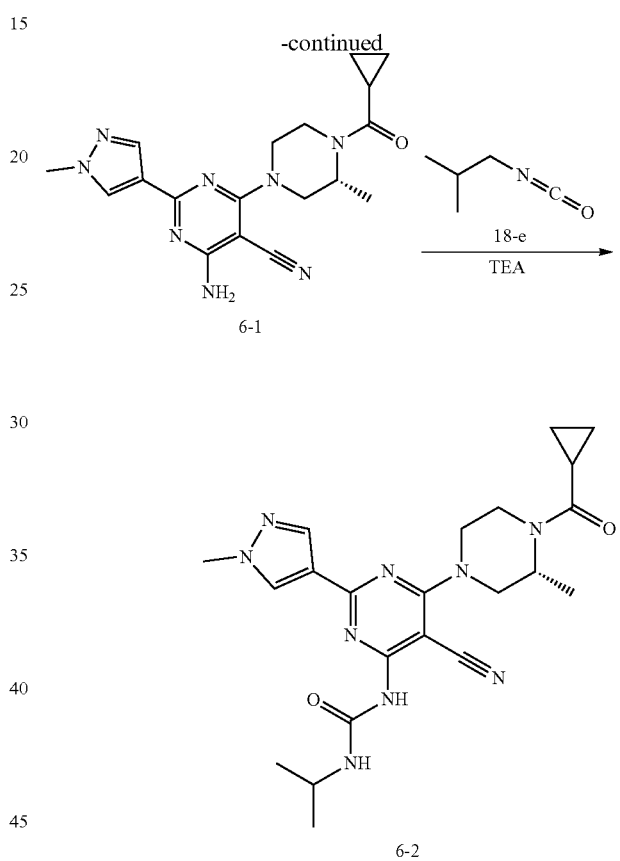 | 5-chloro-4-[(3R)-4-(cyclopropylcarbonyl)-3-methylpiperazin-1-yl]-2-(1-methyl-1H-pyrazol-4-yl)pyrimidine | Calc'd 361, found |

Compound Examples for Table 6

Example 18

Preparation of Compounds 6-1 and 6-2

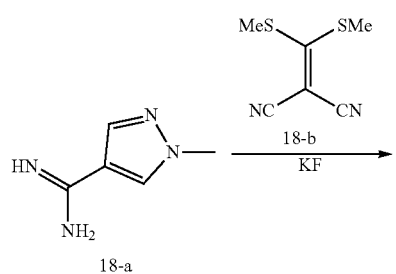

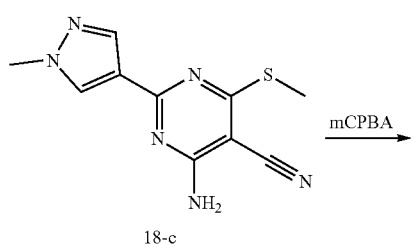

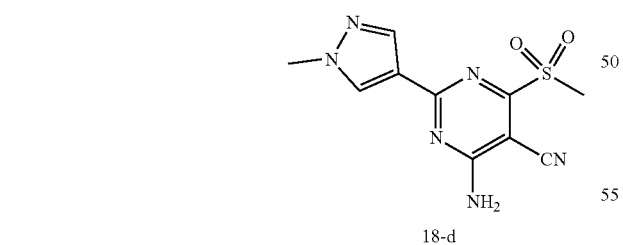

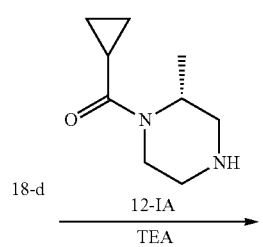

Step 1 4-amino-2-(1-methyl-H-pyrazol-4-yl)-6-(methylthio)pyrimidine-5-carbonitrile (18-c)

To a solution of 1-methyl-1H-pyrazole-4-carboximidamide (commercially available from Aurora Building Blocks, Aurora Fine Chemicals LLC, San Diego, Calif., USA) (18-a) (10.0 g, 810 mmol) in MeCN (50 mL) were added 2-(bis(methylthio)methylene)malononitrile (commercially available from Alfa Aesar, Tewksbury, Mass., USA) (18-b) (15.1 g, 89.0 mmol) and potassium fluoride (KF) (4.68 g, 81.0 mmol) at RT. The resulting mixture was stirred for 12 h at 60° C. After cooling to RT, the reaction mixture was concentrated under reduced pressure. The residue was purified by a column chromatography (silica gel, using gradient of 50%100% EtOAc in hexanes as eluent) to afford 4-amino-2-(1-methyl-1H-pyrazol-4-yl)-6-(methylthio)pyrimidine-5-carbonitrile (18-c). MS (ESI) Calc'd for ($C_{10}H_{11}N_6S$) [M+H]$^+$, 247; found, 247.

Step 2 4-amino-2-(1-methyl-1H-pyrazol-4-yl)-6-(methylsulfonyl)pyrimidine-5-carbonitrile (18-d)

To a solution of 4-amino-2-(1-methyl-H-pyrazol-4-yl)-6-(methylthio) pyrimidine-5-carbonitrile (18-c) (3.00 g, 12.2 mmol) in DCM (40 mL) was added 3-chloroperbenzoic acid (mCPBA) (5.25 g, 30.5 mmol) at RT. The resulting mixture was stirred for 8 h at RT. The pH value of the reaction mixture was adjusted to 8 with saturated aqueous of sodium bicarbonate (5 mL), and the resulting solution was extracted with DCM (3×10 mL). The combined organic layers were dried over anhydrous sodium sulfate and filtered. The filtrate was concentrated under reduced pressure, and the residue was purified by a column chromatography (silica gel, using gradient of 50%100% EtOAc in hexane as eluent) to afford 4-amino-2-(1-methyl-1H-pyrazol-4-yl)-6-(methylsulfonyl)pyrimidine-5-carbonitrile (18-d). MS (ESI) Calc'd for ($C_{10}H_{11}N_6O_2S$) [M+H]$^+$, 278; found, 278.

Step 3 4-amino-6-[(3R)-4-(cyclopropylcarbonyl)-3-methylpiperazin-1-yl]-2-(1-methyl-1H-pyrazol-4-yl)pyrimidine-5-carbonitrile (6-1)

To a solution of 4-amino-2-(1-methyl-H-pyrazol-4-yl)-6-(methylsulfonyl)pyrimidine-5-carbonitrile (18-d) (500 mg, 1.80 mmol) and compound 12-1A (363 mg, 2.16 mmol) in 1,4-dioxane (5 ml) was added DIEA (0.628 ml, 3.59 mmol) at RT. The solution was stirred at 90° C. for 6 h. The mixture was then cooled to RT and was concentrated in vacuo. The residue was diluted with DCM and adsorbed onto silica gel (5 g), after which it was purified by column chromatography (silica gel, eluting with a gradient of 20-25% EtOAc in hexane to give compound 6-1. $^1$H NMR (500 MHz, DMSO-d6) δ 8.21 (s, 1H), 7.90 (s, 1H), 7.21 (br s, 2H), 4.60 (s, 1H), 4.52-4.28 (m, 2H), 4.17 (d, J=11.6 Hz, 1H), 3.88 (s, 3H), 2.98-3.65 (m, 3H), 1.97 (s, 1H), 0.98-1.36 (m, 3H), 0.73 (br s, 4H). MS (ESI) Calc'd for ($C_{18}H_{23}N_8O$) [M+H]$^+$, 367; found, 367.

Step 4 1-{5-cyano-6-[(3R)-4-(cyclopropylcarbonyl)-3-methylpiperazin-1-yl]-2-(1-methyl-1H-pyrazol-4-yl)pyrimidin-4-yl}-3-(1-methylethyl)urea (6-2)

To a solution of compound 6-1 (50.0 mg, 0.14 mmol) in DMF (2 mL) were added TEA (0.04 mL, 0.27 mmol) and 2-isocyanatopropane (18-e) (116 mg, 1.37 mmol) drop-wise at RT. The resulting solution was stirred for 60 h at 60° C. After cooling to RT, the reaction solution was concentrated under reduced pressure. The residue was purified by thin layer chromatography (silical gel, eluting with EtOAc) to afford compound 6-2. $^1$H NMR (300 MHz, DMSO-d6): δ 8.68 (s, 1H), 8.51 (d, J=7.5 Hz, 1H), 8.32 (s, 1H), 7.94 (s, 1H), 4.62 (s, 1H), 4.46 (t, J=12.3 Hz, 2H), 4.23 (d, J=12.6 Hz, 1H), 3.92 (s, 3H), 3.89-3.17 (m, 4H), 2.00-1.96 (m, 1H), 1.23-1.11 (m, 9H), 0.75 (s, 4H). MS (ESI) Calc'd for ($C_{22}H_{30}N_9O_2$) [M+H]$^+$, 452; found, 452.

Example 19

N-{5-cyano-6-[(3R)-4-(cyclopropylcarbonyl)-3-methylpiperazin-1-yl]-2-(1-methyl-1H-pyrazol-4-yl)pyrimidin-4-yl}acetamide

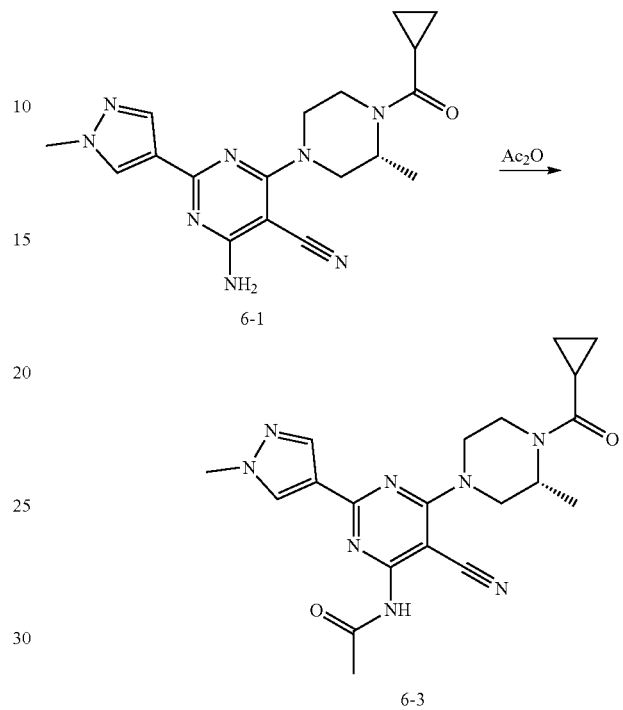

A solution of compound 6-1 (50 mg, 0.14 mmol) in acetic anhydride ($Ac_2O$) (2 ml) was stirred at 110° C. for 12 h. The mixture was then cooled to RT and was diluted with sodium bicarbonate ($NaHCO_3$)(5 mL) and extracted with DCM (3×10 mL). The organic layers were then combined and dried over anhydrous sodium sulfate, filtered, and concentrated in vacuo to give a residue. The crude material was then diluted with DCM, adsorbed onto silica gel, and purified by flash column chromatography (silica gel, eluting with 80-95% EtOAc in hexanes) to give compound 6-3. $^1$H NMR (500 MHz, DMSO-d6) δ 8.36 (s, 1H), 8.00 (s, 1H), 4.65 (br s, 1H), 4.29-4.48 (m, 2H), 4.21 (br s, 1H), 3.91 (s, 3H), 3.02-3.74 (m, 4H), 2.15 (s, 3H), 1.98 (s, 1H), 0.98-1.36 (m, 3H), 0.74 (br s, 4H). MS (ESI) Calc'd for ($C_{20}H_{25}N_8O_2$) [M+H]$^+$, 409; found, 409.

Example 20

4-[(3R)-4-(cyclopropylcarbonyl)-3-methylpiperazin-1-yl]-2-(1-methyl-1H-pyrazol-4-yl)-6-[(2,2,2-trifluoroethyl)amino]pyrimidine-5-carbonitrile (6-4)

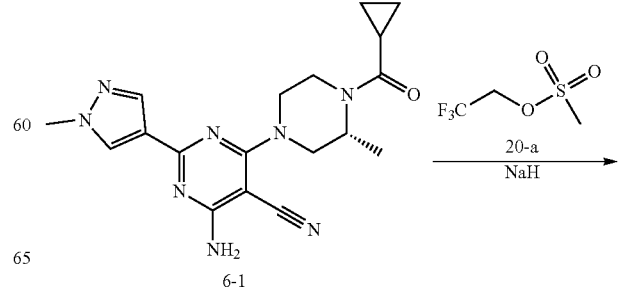

-continued

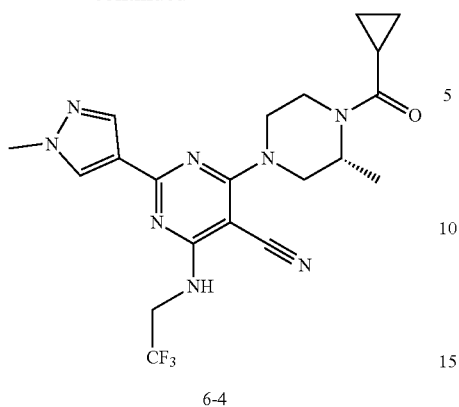

6-4

To a solution of compound 6-1 (50 mg, 0.14 mmol) in DMF (2 mL) was added sodium hydride (NaH) (6.55 mg, 0.16 mmol, 60% by weight) at 0° C. 2,2,2-trifluoroethyl methanesulfonate (20-a) (72.9 mg, 0.41 mmol) was then added, and the resulting mixture was allowed to come to RT and was stirred for 1 h. The reaction was then quenched with water (20 mL), and the resulting mixture was extracted with EtOAc (3×10 mL). The combined organic layers were washed with brine (2×5 mL), dried over anhydrous sodium sulfate, and filtered. The filtrate was concentrated under reduced pressure, and the residue was purified by column chromatography (silica gel, using gradient of 0%-5% MeOH in DCM as eluent) to afford the title compound 6-4. $^1$H NMR (400 MHz, CD$_3$OD): δ 8.23 (s, 1H), 8.04 (s, 1H), 4.70-4.53 (m, 3H), 4.39-4.26 (m, 3H), 3.94 (s, 3H), 3.69-3.30 (m, 2H), 3.28-3.20 (m, 1H), 1.98-1.89 (m, 1H), 1.38-1.22 (m, 3H), 0.94-0.83 (m, 4H). MS (ESI) Calc'd for (C$_2$H$_{24}$F$_3$N$_8$O) [M+H]$^+$, 449; found, 449.

Example 21

4-chloro-6-[(3R)-4-(cyclopropylcarbonyl)-3-methylpiperazin-1-yl]-2-(1-methyl-1H-pyrazol-4-yl)pyrimidine-5-carbonitrile (6-5)

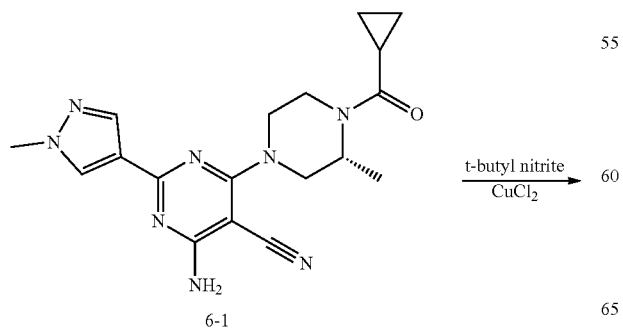

6-1

-continued

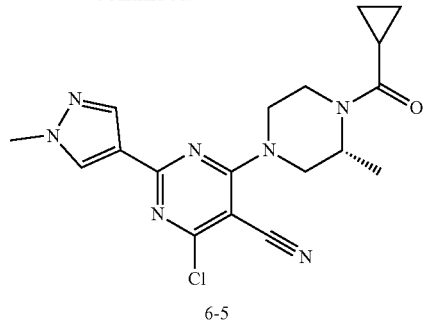

6-5

To a solution of compound 6-1 (400 mg, 1.02 mmol) in MeCN (20 ml) were added tert-butyl nitrite (203 mg, 1.97 mmol) and copper(II) chloride (176 mg, 1.31 mmol). The solution was heated to 80° C. and stirred for 2 h. The solution was then cooled to RT, and the solution was diluted with EtOAc (300 mL) and extracted with water (3×100 mL). The organic layer was washed with brine (3×50 mL), dried over anhydrous sodium sulfate, and filtered. The filtrate was concentrated in vacuo, and the residue was purified by column chromatography (silica gel, eluting with DCM: MeOH(15:1)) to give compound 6-5. H NMR (500 MHz, DMSO-d6) δ 8.49 (s, 1H), 8.06 (s, 1H), 4.34-4.76 (m, 3H), 4.19 (br s, 1H), 3.90 (s, 2H), 3.08-3.83 (m, 6H), 1.97 (s, 1H), 0.98-1.40 (m, 2H), 0.63-0.89 (m, 3H). MS (ESI) Calc'd for (C$_{18}$H$_{21}$CN$_7$O) [M+H]$^+$, 386; found, 386.

Example 22

4-[(3R)-4-(cyclopropylcarbonyl)-3-methylpiperazin-1-yl]-6-ethyl-2-(1-methyl-1H-pyrazol-4-yl)pyrimidine-5-carbonitrile (6-6)

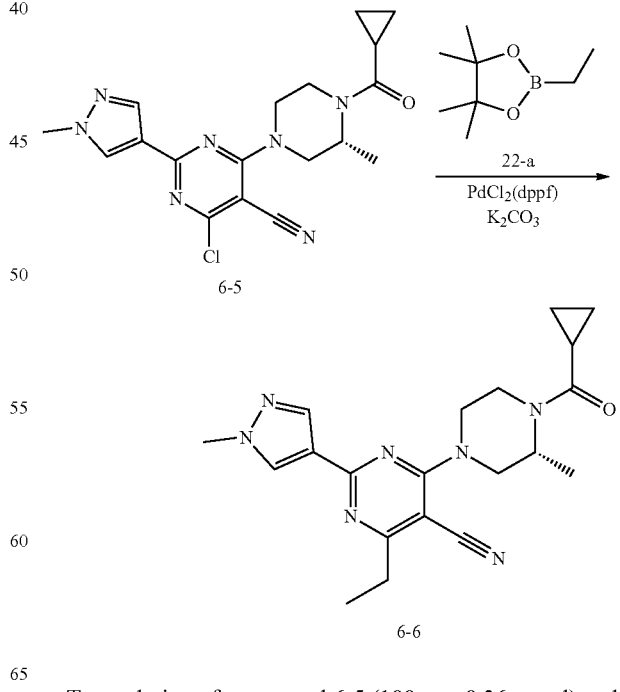

To a solution of compound 6-5 (100 mg, 0.26 mmol) and 2-ethyl-4,4,5,5-tetramethyl-1,3,2-dioxaborolane (22-a) (404 mg, 2.6 mmol) in dioxane (2 ml) were added potassium carbonate (107 mg, 0.78 mmol), PdCl$_2$(dppf) (19.0 mg, 0.026 mmol) and water (0.5 ml) at RT. The reaction mixture was degassed with nitrogen, and the mixture was heated to 90° C. and stirred for 2 h. The mixture was then cooled to RT, and the mixture was concentrated in vacuo. The crude material was purified by thin layer chromatography (silica gel, eluting with 10%-15% MeOH in DCM) to give compound 6-6. $^1$H NMR (500 MHz, DMSO-d6) δ 8.41 (s, 1H), 8.04 (s, 1H), 4.37-4.73 (m, 3H), 4.19 (d, J=10.5 Hz, 1H), 3.90 (s, 3H), 3.04-3.75 (m, 5H), 2.73-2.88 (m, 2H), 1.98 (s, 1H), 1.00-1.37 (m, 5H), 0.73 (br s, 3H). MS (ESI) Calc'd for (C$_{20}$H$_{26}$N$_7$O) [M+H]$^+$, 380; found, 380.

Example 23

4-(cyclobutylamino)-6-[(3R)-4-(cyclopropylcarbonyl)-3-methylpiperazin-1-yl]-2-(1-methyl-1H-pyrazol-4-yl)pyrimidine-5-carbonitrile (6-7)

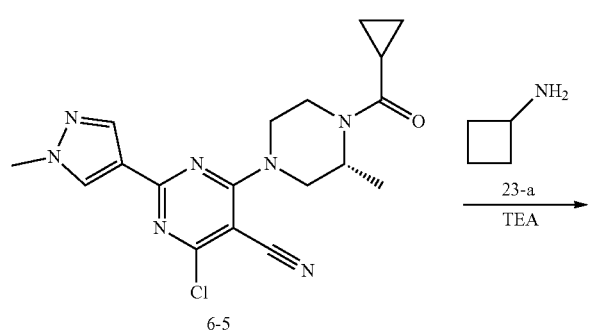

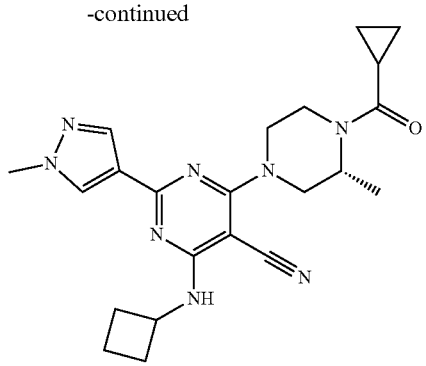

Cyclobutanamine (23-a) (9.68 mg, 0.14 mmol) was added into a solution of compound 6-5 (35 mg, 0.091 mmol) and TEA (0.038 ml, 0.272 mmol) in DMF (2 ml). The solution was stirred for 2 h at RT, after which EtOAc (50 mL) was added and the solution was extracted with water (3×20 mL). The organic layer was washed with brine (30 mL), dried over anhydrous sodium sulfate, and filtered. The filtrate was concentrated in vacuo, and the residue was purified by column chromatography (silica gel, eluting with DCM:MeOH (15:1)) to give the crude product. The crude product was further purified by reverse-phase, preparatory HPLC (Phenomenex RP18, 5 um, 21.2×150 mm; eluting with a gradient of 33-57% MeCN in water water (0.05% ammonium bicarbonate+carbon dioxide) to give compound 6-7. MS (ESI) Calc'd for (C$_{22}$H$_{29}$N$_8$O) [M+H]$^+$, 421; found, 421.

Example 24

4-[(3R)-4-(cyclopropylcarbonyl)-3-methylpiperazin-1-yl]-2-(1-methyl-1H-pyrazol-4-yl)-6-(phenylamino)pyrimidine-5-carbonitrile (6-8)

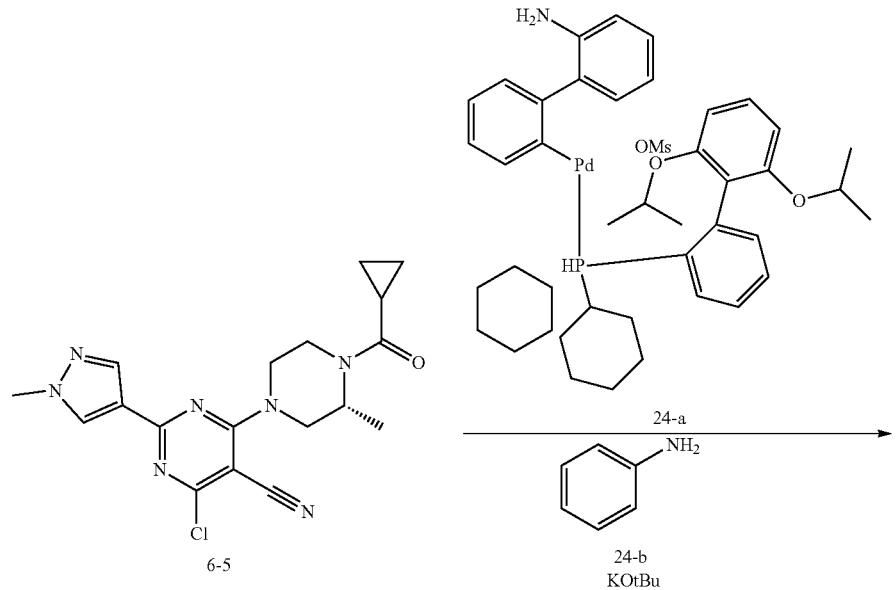

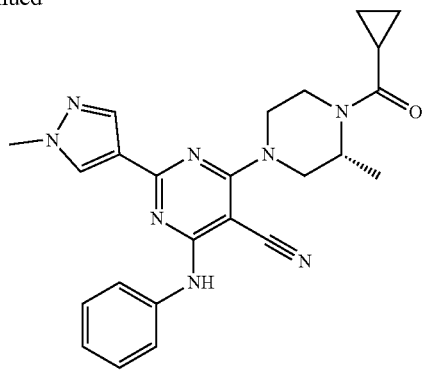

6-8

A mixture of compound 6-5 (50 mg, 0.130 mmol), aniline (24-b) (18.10 mg, 0.194 mmol), (2-dicyclohexylphosphino-2',6'-diisopropoxy-1,1'-biphenyl)[2-(2'-amino-1,1'-biphenyl)]palladium(II) methanesulfonate (24-a) (11.8 mg, 0.013 mmol) and potassium 2-methylpropan-2-olate (KOtBu) (29.1 mg, 0.26 mmol) in toluene (2 ml) was stirred at 60° C. for 2 h. After cooling to room temperature, the mixture was concentrated under reduce pressure to give a residue. The residue was purified by column chromatography (silica gel, eluting with a gradient of 0%-5% MeOH in DCM) to afford compound 6-8. $^1$H NMR (500 MHz, DMSO-d6) δ 9.23 (s, 1H), 8.23 (s, 1H), 7.91 (s, 1H), 7.66 (d, J=6.9 Hz, 2H), 7.36 (s, 2H), 7.09 (s, 1H), 4.63 (s, 1H), 4.30-4.54 (m, 2H), 4.21 (d, J=10.4 Hz, 1H), 3.89 (s, 3H), 3.06-3.71 (m, 3H), 1.99 (s, 1H), 1.03-1.19 (m, 3H), 0.74 (br s, 4H). MS (ESI) Calc'd for ($C_{24}H_{27}N_8O$) [M+H]$^+$, 443; found, 443.

Example 25

4-chloro-2-[(3R)-4-(cyclopropylcarbonyl)-3-methylpiperazin-1-yl]-6-(1-methyl-1H-pyrazol-4-yl)pyrimidine-5-carbonitrile (6-9)

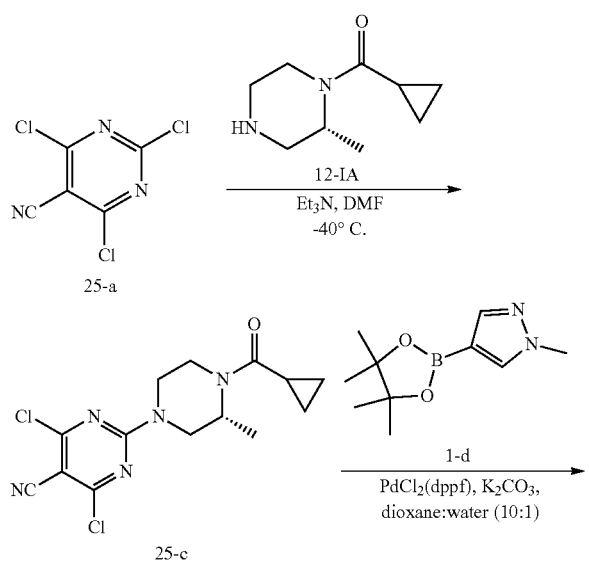

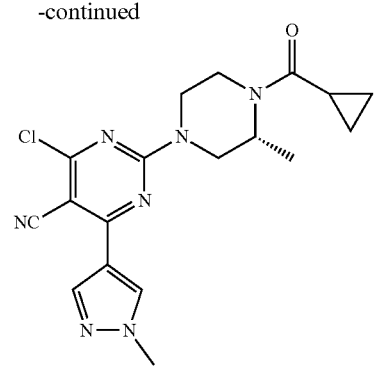

6-9

Step 1 (R)-4,6-dichloro-2-(4-(cyclopropanecarbonyl)-3-methylpiperazin-1-yl)pyrimidine-5-carbonitrile (25-a)

To a solution of 2,4,6-trichloropyrimidine-5-carbonitrile (25-a) (2.00 g, 9.60 mmol) in DMF (20 ml) at −40° C. under an atmosphere of nitrogen, was added trimethylamine (Et$_3$N) (2.67 ml, 19.2 mmol) and (R)-cyclopropyl(2-methylpiperazin-1-yl)methanone (12-IA) (1.61 g, 9.60 mmol). The resulting mixture was stirred for 2 h. After 2 h, the reaction was quenched via the addition of water (50 mL) and allowed to warm to ambient temperature. The mixture was extracted with EtOAc (3×100 mL). The combined organic layers were washed with brine (100 mL), dried over anhydrous sodium sulfate and filtered. The filtrate was concentrated under reduced pressure and the residue was purified via silica gel chromatography (50 g, 100-200 mesh), eluting with 0-30% EtOAc in hexane to afford (R)-4,6-dichloro-2-(4-(cyclopropanecarbonyl)-3-methylpiperazin-1-yl)pyrimidine-5-carbonitrile (25-c). MS (ESI) Calc'd for ($C_{14}H_{16}C_2N_5O$) [M+H]$^+$, 340; found, 340.

Step 2 (R)-4-chloro-2-(4-(cyclopropanecarbonyl)-3-methylpiperazin-1-yl)-6-(1-methyl-1H-pyrazol-4-yl)pyrimidine-5-carbonitrile (6-9)

To a solution of (R)-4,6-dichloro-2-(4-(cyclopropanecarbonyl)-3-methylpiperazin-1-yl)pyrimidine-5-carbonitrile (25-c) (1.00 g, 2.94 mmol) in dioxane (20 ml), was added 1-methyl-4-(4,4,5,5-tetramethyl-1,3,2-dioxaborolan-2-yl)-

1H-pyrazole (1-d) (0.612 g, 2.94 mmol), K₂CO₃ (406 mg, 2.94 mmol), water (2 ml), PdCl₂(dppf) (2.15 g, 2.94 mmol) at 20° C. The resulting mixture was stirred for 2 h at 90° C. under an atmosphere of nitrogen. At 2 h, water (50 ml) was added to the reaction mixture. The resulting mixture was extracted with EtOAc (3×100 mL). The combined organic layers were washed with brine (100 mL), dried over anhydrous sodium sulfate and filtered. The filtrate was concentrated under reduced pressure and the resulting residue was purified via silica gel column chromatography (20 g, 100-200 mesh), eluting with 0-100% EtOAc in hexanes to afford (R)-4-chloro-2-(4-(cyclopropanecarbonyl)-3-methylpiperazin-1-yl)-6-(1-methyl-1H-pyrazol-4-yl)pyrimidine-5-carbonitrile (compound 6-9). ¹H NMR (500 MHz, DMSO-d6) δ 8.62 (s, 1H), 8.26 (s, 1H), 4.66 (br s, 2H), 4.12-4.48 (m, 2H), 3.96 (s, 3H), 2.93-3.57 (m, 3H), 1.98 (s, 1H), 0.89-1.31 (m, 3H), 0.75 (br s, 4H). MS (ESI) Calc'd for (C₁₈H₂₁CN₇O) [M+H]⁺, 386; found, 386.

Example 26

4-[(3R)-4-(cyclopropylcarbonyl)-3-methylpiperazin-1-yl]-6-methyl-2-(1-methyl-1H-pyrazol-4-yl)pyrimidine-5-carbonitrile (6-10)

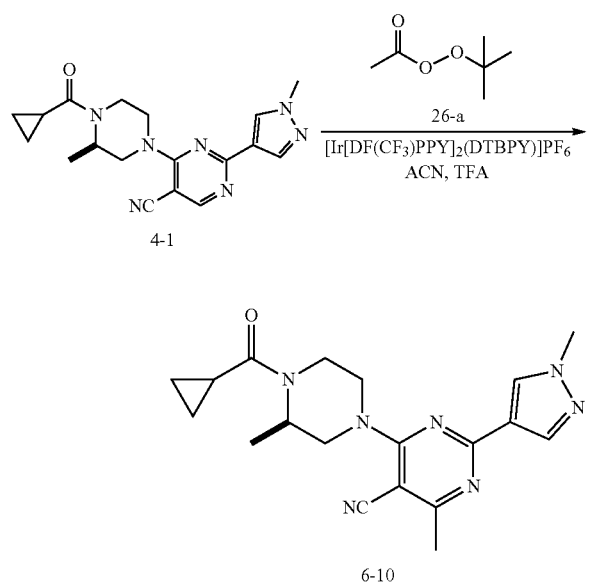

To a vial were added [Ir[DF(CF₃)PPY]₂(DTBPY)]PF₆ (4.04 mg, 3.60 μmol), compound 4-1 (25.3 mg, 0.072 mmol), MeCN (180 μl), TFA (180 μl) and tert-butyl ethaneperoxoate (26-a) (26 mg, 0.098 mmol). The mixture was evacuated and back-filled with nitrogen (×3), after which the vial was irradiated with blue LED light (450 nm) at RT for 19 h. The mixture was filtered and was purified b preparative, reverse-phase HPLC (eluting with ACN/water with 0.1% TFA) to afford compound 6-10 as the TFA salt. ¹H NMR (600 MHz, DMSO-d₆) δ 8.38 (s, 1H), 8.00 (s, 1H), 4.75-4.31 (m, 3H), 4.24-4.10 (m, 1H), 3.86 (s, 3H), 3.68-3.07 (m, 3H), 2.48 (s, 3H), 2.01-1.88 (m, 1H), 1.32-0.96 (m, 3H), 0.87-0.52 (m, 4H). MS (ESI) Calc'd for C₁₉H₂₄N₇O [M+H]⁺, 366; found, 366.

Example 27

4-[(3R)-4-(cyclopropylcarbonyl)-3-methylpiperazin-1-yl]-2-[1-methyl-5-(3,3,3-trifluoropropyl)-1H-pyrazol-4-yl]pyrimidine-5-carbonitrile (6-11)

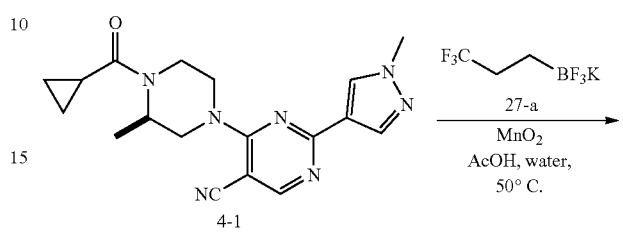

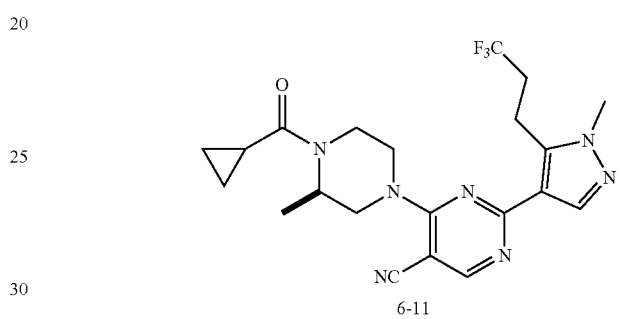

To a vial were added compound 4-1 (18 mg, 0.051 mmol), potassium 3,3,3-trifluoropropane-1-trifluoroborate (27-a) (20.90 mg, 0.102 mmol), manganese dioxide (MnO₂) (10.69 mg, 0.123 mmol), and a solution of acetic acid (150 μl) and water (450 μl). The mixture was stirred at 50° C. for 18 h, then at 90° C. for another 18 h. The mixture was then cooled and filtered, and the resulting residue was purified on preparative, reverse-phase HPLC (eluting with ACN/water with 0.1% TFA) to afford compound 6-11 as the TFA salt. ¹H NMR (600 MHz, DMSO-d₆) δ 8.66 (s, 1H), 8.04 (s, 1H), 4.80-4.01 (m, 7H), 3.83 (s, 3H), 3.50-3.24 (m, 2H), 2.66-2.51 (m, 2H), 1.98-1.88 (m, 1H), 1.30-1.00 (m, 3H), 0.85-0.56 (m, 4H). MS (ESI) Calc'd for C₂₁H₂₅F₃N₇O [M+H]⁺, 448; found, 448.

Example 28

2-[(3R)-4-(cyclopropylcarbonyl)-3-methylpiperazin-1-yl]-4-(2-methoxyethyl)-6-(1-methyl-1H-pyrazol-4-yl)pyrimidine-5-carbonitrile (6-12)

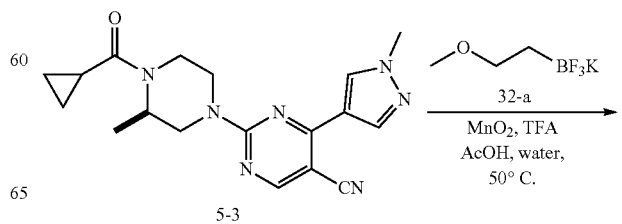

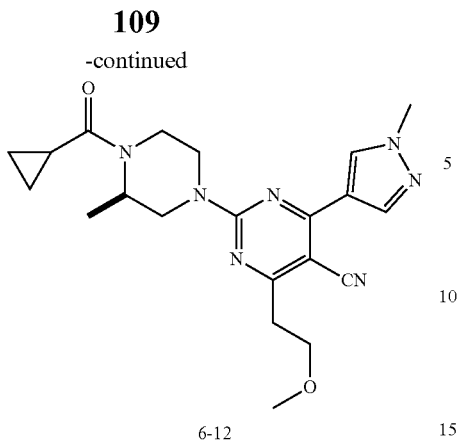

6-12

To a vial were added compound 5-3 (40 mg, 0.114 mmol), potassium 2-methoxyethyl trifluoroborate (32-a) (37.8 mg, 0.228 mmol), manganese dioxide (MnO$_2$) (19.79 mg, 0.228 mmol), and a solution of acetic acid (AcOH) (250 µl), water (750 µl), and TFA (200 µl, 2.60 mmol). The mixture was stirred at 50° C. for 20 h. The mixture was then cooled and filtered, and the filtrate was purified by preparative, reverse-phase HPLC (eluting with ACN/water with 0.1% TFA) to afford compound 6-12 as the TFA salt. $^1$H NMR (600 MHz, DMSO-d$_6$) δ 8.54 (s, 1H), 8.21 (s, 1H), 4.80-4.30 (m, 4H), 4.29-4.09 (m, 3H), 3.91 (s, 3H), 3.80-3.66 (m, 2H), 3.47-3.26 (m, 1H), 3.21 (s, 3H), 3.16-2.89 (m, 1H) 2.09-1.83 (m, 1H), 1.27-0.88 (m, 3H), 0.84-0.51 (m, 4H). MS (ESI) Calc'd for C$_{21}$H$_{28}$N$_7$O$_2$ [M+H]$^+$, 410; found, 410.

Example 29

4-(3-cyano-1-methyl-1H-pyrazol-4-yl)-2-[(3R)-4-(cyclopropylcarbonyl)-3-methylpiperazin-1-yl]pyrimidine-5-carbonitrile (6-13)

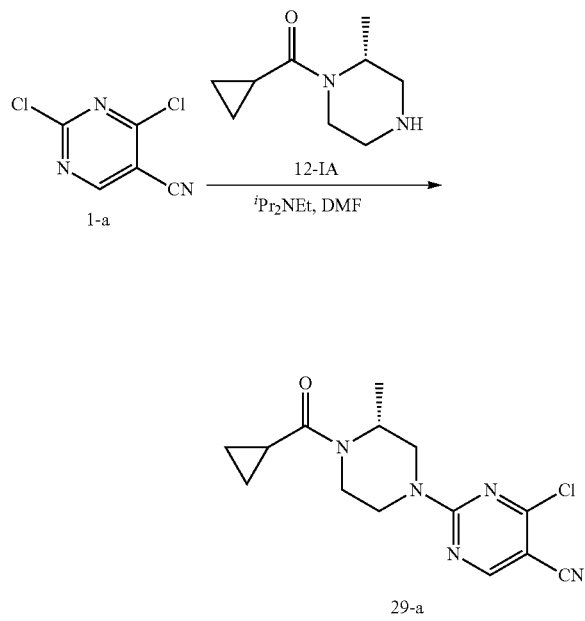

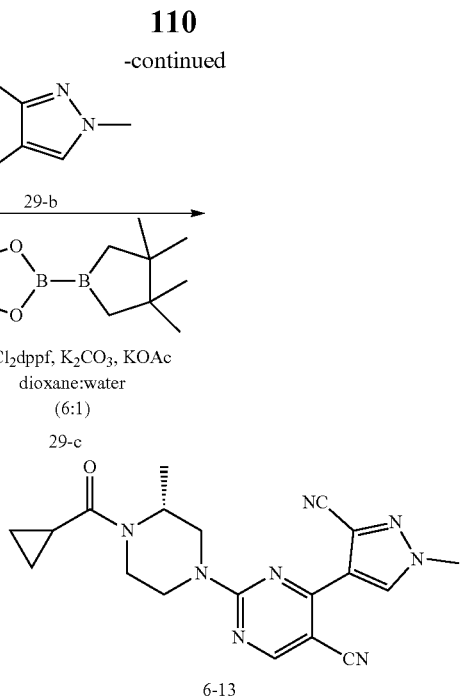

Step 1 (R)-4-chloro-2-(4-(cyclopropanecarbonyl)-3-methylpiperazin-1-yl)pyrimidine-5-carbonitrile (29-a)

2,4-dichloropyrimidine-5-carbonitrile (1-a) (3.00 g, 17.2 mmol) and diisopropylethylamine ($^i$Pr$_2$NEt) (3.01 ml, 17.2 mmol) were combined in DMF (30 ml) and cooled to 0° C. (R)-cyclopropyl(2-methylpiperazin-1-yl)methanone (12-IA) (2.90 g, 17.2 mmol) was added and the resulting mixture was allowed to warm to 25° C. After 1 h at this temperature, water (30 mL) was added and the mixture was extracted with ethyl acetate (3×60 mL). The combined organic fractions were washed with brine (3×50 mL), dried (Na$_2$SO$_4$), filtered and concentrated under vacuum. The residue was purified via reverse phase HPLC, eluting with H$_2$O (0.05% NaHCO$_3$ modifier)/CH$_3$CN (15% to 25% in 20 min), (retention time=16 min) to give (R)-4-chloro-2-(4-(cyclopropanecarbonyl)-3-methylpiperazin-1-yl)pyrimidine-5-carbonitrile (29-a). MS (ESI) Calc'd for (C$_{14}$H$_{17}$ClN$_5$O) [M+H]$^+$, 306; found, 306.

Step 2 (R)-4-(3-cyano-1-methyl-1H-pyrazol-4-yl)-2-(4-(cyclopropanecarbonyl)-3-methylpiperazin-1-yl)pyrimidine-5-carbonitrile (6-13)

A mixture of 4-bromo-1-methyl-1H-pyrazole-3-carbonitrile (29-b) (60.8 mg, 0.327 mmol), 4,4,4',4',5,5,5',5'-octamethyl-2,2'-bi(1,3,2-dioxaborolane) (29-c) (91.0 mg, 0.360 mmol), PdCl$_2$(dppf) (47.9 mg, 0.065 mmol) and potassium acetate (64.2 mg, 0.654 mmol) in 1,4-dioxane (3 ml) was stirred for 3 h at 80° C. Then (R)-4-chloro-2-(4-(cyclopropanecarbonyl)-3-methylpiperazin-1-yl)pyrimidine-5-carbonitrile (29-a) (100 mg, 0.327 mmol), potassium carbonate (90.1 mg, 0.654 mmol) and water (0.5 ml) were added and the resulting mixture was stirred for 5 h at 80° C. The mixture was cooled, water (10 mL) was added and the mixture was extracted with ethyl acetate (3×20 mL). The combined organic fractions were washed with brine (3×20 mL), dried over sodium sulfate, filtered and concentrated under vacuum. The residue was purified by preparative-TLC, eluting with ethyl acetate:petroleum ether=1:2 to give compound 6-13. MS (ESI) Calc'd for ($C_9H_{21}N_8O$) [M+H]$^+$, 377; found, 377.

Example 30

4-(3-amino-1-methyl-1H-pyrazol-4-yl)-2-[(3R)-4-(cyclopropylcarbonyl)-3-methylpiperazin-1-yl]pyrimidine-5-carbonitrile (6-14)

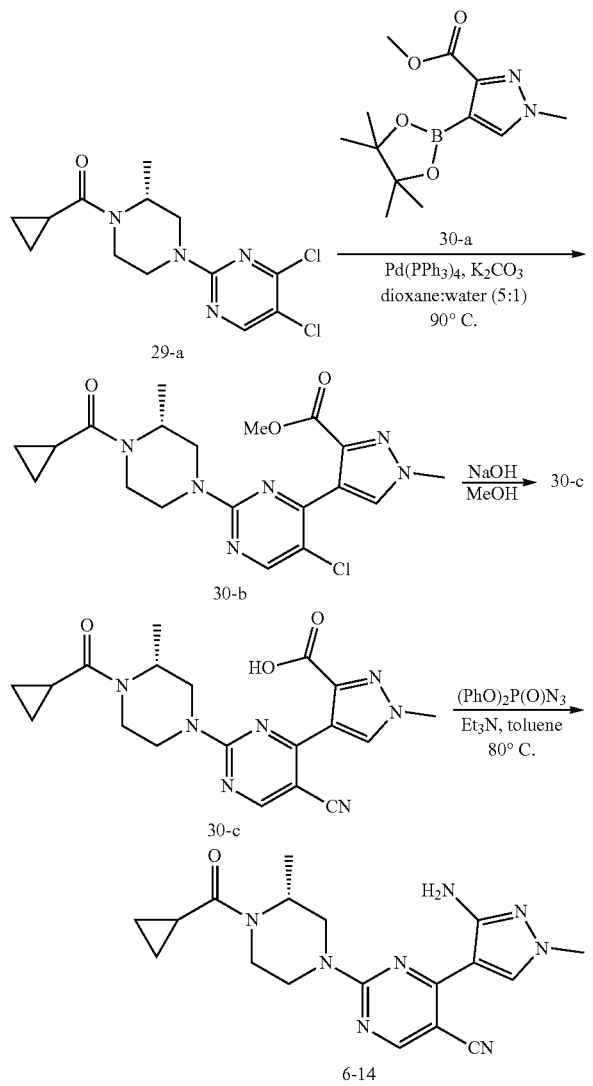

Step 1 (R)-methyl 4-(5-cyano-2-(4-(cyclopropanecarbonyl)-3-methylpiperazin-1-yl)pyrimidin-4-yl)-1-methyl-1H-pyrazole-3-carboxylate (30-b)

(R)-4-chloro-2-(4-(cyclopropanecarbonyl)-3-methylpiperazin-1-yl)pyrimidine-5-carbonitrile (29-a) (40.0 mg, 0.131 mmol) was added to a mixture of 1,4-dioxane (1 ml) and water (0.2 ml). Then potassium carbonate ($K_2CO_3$), (36.2 mg, 0.262 mmol), Pd(PPh$_3$)$_4$ (7.56 mg, 6.54 µmol) and methyl 1-methyl-4-(4,4,5,5-tetramethyl-1,3,2-dioxaborolan-2-yl)-1H-pyrazole-3-carboxylate (30-a) (69.6 mg, 0.262 mmol) were added. The mixture was stirred for 3 h at 90° C. under an atmosphere of nitrogen. The reaction mixture was cooled to ambient temperature then diluted with ethyl acetate (80 mL). The mixture was extracted with water (3×40 mL). The organic layer was washed with brine (3×40 mL), dried over anhydrous sodium sulfate, filtered and concentrated in vacuo. The residue was purified by column chromatography on silica gel (300-400 mesh), eluting with ethyl acetate/petroleum ether (2:1). The isolated material was further purified by preparative-HPLC with the following conditions: Instrument, Waters® 2767 (Waters Corporation, Milford, Mass., USA); Column: Phenomenex® RP18, 5 um, 21.2×150 mm (Phenomenex, Torrance, Calif., USA); mobile phase: water (0.05% ammonium bicarbonate+carbon dioxide) and acetonitrile (25% acetonitrile up to 55% in 8 min, hold 95% for 2 min, down to 25% in 2 min); Detector, UV 220 and 254 nm. The collected fractions were combined and concentrated in vacuo to give (R)-methyl 4-(5-cyano-2-(4-(cyclopropanecarbonyl)-3-methylpiperazin-1-yl)pyrimidin-4-yl)-1-methyl-1H-pyrazole-3-carboxylate (30-b). MS (ESI) Calc'd for ($C_{20}H_{24}N_7O_3$) [M+H]$^+$, 410; found, 410.

Step 2 (R)-4-(5-cyano-2-(4-(cyclopropanecarbonyl)-3-methylpiperazin-1-yl)pyrimidin-4-yl)-1-methyl-1H-pyrazole-3-carboxylic acid (30-c)

To a stirred solution of (R)-methyl 4-(5-cyano-2-(4-(cyclopropanecarbonyl)-3-methylpiperazin-1-yl)pyrimidin-4-yl)-1-methyl-1H-pyrazole-3-carboxylate (30-b) (100.0 mg, 0.244 mmol) in methanol (MeOH) (10 ml) at 0° C. was added 1 M aqueous sodium hydroxide (10 mL, 10 mmol) dropwise. The solution was stirred for 3 h at ambient temperature. The pH of the solution was adjusted to pH 6 with aqueous 1M acetic acid. The resulting mixture was extracted with ethyl acetate (3×100 mL). The combined organic layers were washed with brine (3×60 mL), dried over anhydrous sodium sulfate and filtered. The filtrate was concentrated in vacuo. The residue was purified by column chromatography on silica gel (300-400 mesh), eluting with ethyl acetate/petroleum ether to give (R)-4-(5-cyano-2-(4-(cyclopropanecarbonyl)-3-methylpiperazin-1-yl)pyrimidin-4-yl)-1-methyl-1H-pyrazole-3-carboxylic acid (30-c). MS (ESI) Calc'd for ($C_{19}H_{22}N_7 3$) [M+H]$^+$, 396; found, 396.

Step 3 (R)-4-(3-amino-1-methyl-1H-pyrazol-4-yl)-2-(4-(cyclopropanecarbonyl)-3-methylpiperazin-1-yl)pyrimidine-5-carbonitrile (6-13)

To a stirred solution of (R)-4-(5-cyano-2-(4-(cyclopropanecarbonyl)-3-methylpiperazin-1-yl)pyrimidin-4-yl)-1-methyl-1H-pyrazole-3-carboxylic acid (30-c) (40.0 mg, 0.101 mmol) in toluene (1 ml) was added diphenylphosphoryl azide ((PhO)$_2$P(O)N$_3$) (41.8 mg, 0.152 mmol) via syringe. Next triethylamine (Et$_3$N) (0.042 ml, 0.303 mmol) was added into the solution by syringe. The reaction mixture was stirred for 10 min at ambient temperature and then heated to 80° C. for an additional 3 h. The solution was cooled to ambient temperature and quenched via the addition of water (50 mL). The mixture was extracted with ethyl acetate (3×50 mL). The combined organic layers were washed with brine (3×30 mL), dried over anhydrous sodium sulfate and filtered. The filtrate was concentrated in vacuo. The resulting residue was purified by preparative-HPLC with the following conditions: Instrument, Waters-2767; Column: Phenomenex RP18, 5 um, 21.2×150 mm; mobile phase: water (0.05% ammonium bicarbonate+carbon dioxide) and acetonitrile (35% acetonitrile up to 55% in 8 min, hold 95% for 2 min, down to 35% in 2 min); Detector, UV 220 and 254 nm. The collected fractions were combined and concentrated in vacuo to give compound 6-14. $^1$H NMR (500 MHz, DMSO-d6) δ 8.64 (s, 1H), 8.33 (s, 1H), 5.93 (br s, 2H), 4.46-4.82 (m, 2H), 4.04-4.46 (m, 3H), 2.87-3.91 (m, 5H), 1.98 (s, 1H), 0.92-1.27 (m, 2H), 0.73 (br s, 5H). MS (ESI) Calc'd for ($C_{18}H_{23}N_8O$) [M+H]t, 367.2; found, 367.1.

Example 31

4-[(3R)-4-(cyclopropylcarbonyl)-3-methylpiperazin-1-yl]-2-(5,6-dihydro-4H-pyrrolo[1,2-b]pyrazol-3-yl)pyrimidine-5-carbonitrile (6-15)

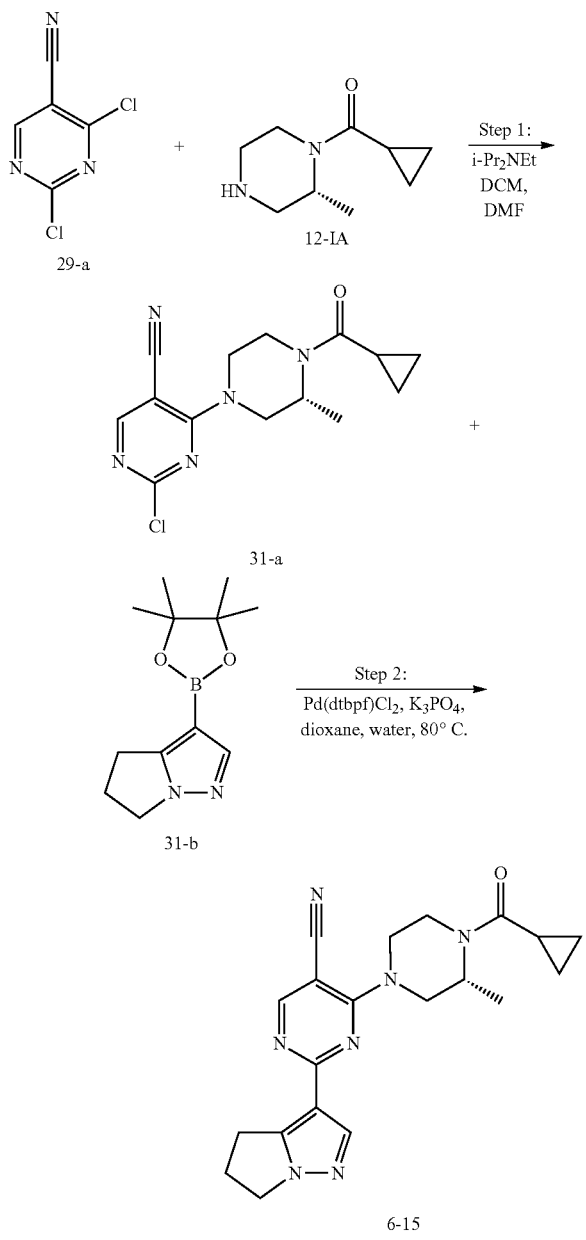

Step 1 (R)-2-Chloro-4-(4-(cyclopropanecarbonyl)-3-methylpiperazin-1-yl)pyrimidine-5-carbonitrile (31-a)

A solution of (R)-cyclopropyl(2-methylpiperazin-1-yl)methanone (12-IA) (850 mg, 5.0 mmol) in dichloromethane (DCM) (5 mL) and treated with N,N-diisopropylethylamine (2.0 mL, 11 mmol) and cooled to 0° C. A solution of 2,4-dichloropyrimidine-5-carbonitrile (29-a) (1.0 g, 5.8 mmol) in DMF (5 mL) was added and the mixture stirred for 10 min. The crude reaction mixture was diluted with DCM and washed with water. The organic layer was dried ($Na_2SO_4$) and concentrated. The residue was purified by chromatography on $SiO_2$ (gradient of 0-100% EtOAc/DCM) to provide undesired byproduct (R)-4-chloro-2-(4-(cyclopropanecarbonyl)-3-methylpiperazin-1-yl)pyrimidine-5-carbonitrile along with desired intermediate (R)-2-chloro-4-(4-(cyclopropanecarbonyl)-3-methylpiperazin-1-yl)pyrimidine-5-carbonitrile (31-a). Desired isomer: $^1$H NMR (600 MHz, DMSO-d$_6$) δ 8.63 (s, 1H), 4.59 (br m, 1H), 4.37 (m, 1H), 4.30 (br m, 1H), 4.13 (br m, 1H), 3.70-3.40 (m, 2H), 3.33 (br m, 1H), 1.92 (m, 1H), 1.25-1.00 (br m, 3H), 0.73 (br, 1H), 0.69 (br, 3H). MS (ESI) Calc'd for ($C_{14}H_{17}ClN_5O$) [M+H]$^+$, 306; found, 306.

Step 2 4-[(3R)-4-(cyclopropylcarbonyl)-3-methylpiperazin-1-yl]-2-(5,6-dihydro-4H-pyrrolo[1,2-b]pyrazol-3-yl)pyrimidine-5-carbonitrile (6-15)

A mixture containing (R)-2-chloro-4-(4-(cyclopropanecarbonyl)-3-methylpiperazin-1-yl)pyrimidine-5-carbonitrile (31-a) (30 mg, 0.098 mmol), 3-(4,4,5,5-tetramethyl-1,3,2-dioxaborolan-2-yl)-5,6-dihydro-4H-pyrrolo[1,2-b]pyrazole (31-b) (commercially available from Synnovator, Inc., Research Triangle Park, NC, USA) (30 mg, 0.13 mmol), 1,1'-bis(di-tert-butylphosphino)ferrocene palladium dichloride (Pd(dtbpf)Cl$_2$) (7 mg, 10 mmol) in dioxane (0.7 mL) was treated with a 1 M solution of $K_3PO_4$ in water (0.2 mL, 0.2 mmol). The reaction mixture was stirred at 80° C. for 3 h. The crude reaction mixture was cooled to RT, filtered and purified by reverse phase chromatography (gradient of MeCN/water with 0.1% TFA) to provide compound 6-15 as the TFA salt. $^1$H NMR (600 MHz, DMSO-d$_6$) δ 8.67 (s, 1H), 8.05 (s, 1H), 4.66 (m, 1H), 4.51 (m, 1H), 4.45 (m, 1H), 4.20 (m, 1H), 4.14 (m, 2H), 3.70-3.40 (br m, 2H), 3.40-3.15 (br m, 1H), 3.12 (m, 2H), 2.60 (m, 2H), 1.98 (m, 1H), 1.25 (m, 2H), 1.08 (br, 1H), 0.77 (br, 1H), 0.74 (br, 3H). MS (ESI) Calc'd for ($C_{20}H_{24}N_{70}$) [M+H]$^+$, 378; found, 378.

Compounds 6-16 and 6-17 found in Table 6 were prepared in a manner analogous to Example 18, Step 4, except that 1,1,1-trifluoro-2-isocyanatoethane and isocyanatocyclobutane, respectively, were used in place of 2-isocyanatopropane.

Compounds 6-18 through 6-23 found in Table 6 were prepared in a manner analogous to Example 19, using the appropriate amine or alcohol nucleophile in place of cyclobutanamine.

Compounds 6-24 and 6-25 through 6-27 found in Table 6 were prepared in a manner similar to Example 28 using the corresponding boronate salts. In many cases, the regioselectivity was poor but the desired compound could be isolated using standard preperative HPLC methods.

Compounds 6-28 and 6-29 found in Table 6 were prepared in a manner analogous to Example 29, using the corresponding boronic esters.

Compound 6-30 found in Table 6 was prepared using a sequence analogous to Example 31, substituting 3-(4,4,5,5-tetramethyl-1,3,2-dioxaborolan-2-yl)-5,6-dihydro-4H-pyrrolo[1,2-b]pyrazole for 1-(difluoromethyl)-4-(4,4,5,5-tetramethyl-1,3,2-dioxaborolan-2-yl)-1H-pyrazole.

TABLE 6

| Compound | Structure | Name | Exact Mass [M + H]+ |
|---|---|---|---|
| 6-1 | 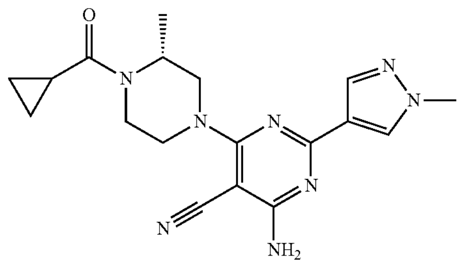 [SMILES: C[C@@H]1CN(c2nc(-c3cnn(C)c3)nc(N)c2C#N)CCN1C(=O)C1CC1] | 4-amino-6-[(3R)-4-(cyclopropylcarbonyl)-3-methylpiperazin-1-yl]-2-(1-methyl-1H-pyrazol-4-yl)pyrimidine-5-carbonitrile | Calc'd 367, found |
| 6-2 | 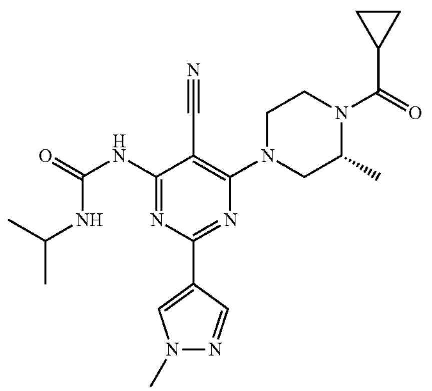 [SMILES: CC(C)NC(=O)Nc1nc(-c2cnn(C)c2)nc(N2CCN(C(=O)C3CC3)[C@H](C)C2)c1C#N] | 1-{5-cyano-6-[(3R)-4-(cyclopropylcarbonyl)-3-methylpiperazin-1-yl]-2-(1-methyl-1H-pyrazol-4-yl)pyrimidin-4-yl}-3-(1-methylethyl)urea | Calc'd 452, found |
| 6-3 | 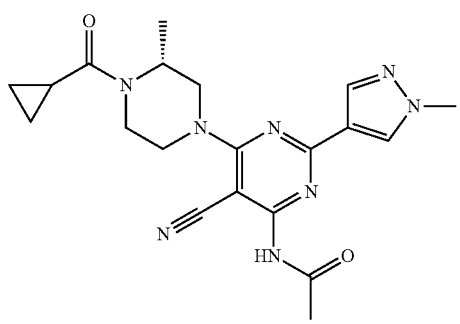 [SMILES: CC(=O)Nc1nc(-c2cnn(C)c2)nc(N2CCN(C(=O)C3CC3)[C@H](C)C2)c1C#N] | N-{5-cyano-6-[(3R)-4-(cyclopropylcarbonyl)-3-methylpiperazin-1-yl]-2-(1-methyl-1H-pyrazol-4-yl)pyrimidin-4-yl}acetamide | Calc'd 409, found |
| 6-4 | 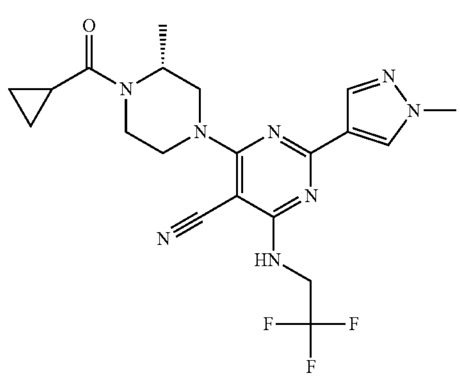 [SMILES: C[C@@H]1CN(c2nc(-c3cnn(C)c3)nc(NCC(F)(F)F)c2C#N)CCN1C(=O)C1CC1] | 4-[(3R)-4-(cyclopropylcarbonyl)-3-methylpiperazin-1-yl]-2-(1-methyl-1H-pyrazol-4-yl)-6-[(2,2,2-trifluoroethyl)amino]pyrimidine-5-carbonitrile | Calc'd 449, found |

TABLE 6-continued

| Compound | Structure | Name | Exact Mass [M + H]+ |
|---|---|---|---|
| 6-5 | 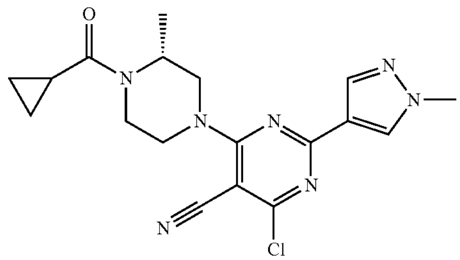 [SMILES: C[C@@H]1CN(c2nc(-c3cnn(C)c3)nc(Cl)c2C#N)CCN1C(=O)C1CC1] | 4-chloro-6-[(3R)-4-(cyclopropylcarbonyl)-3-methylpiperazin-1-yl]-2-(1-methyl-1H-pyrazol-4-yl)pyrimidine-5-carbonitrile | Calc'd 386, found |
| 6-6 | 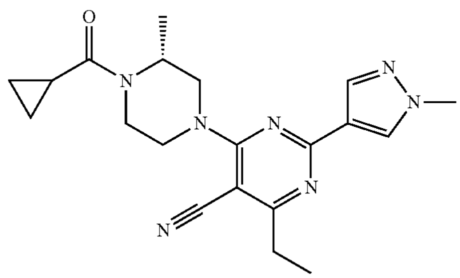 [SMILES: CCc1nc(-c2cnn(C)c2)nc(N2CCN(C(=O)C3CC3)[C@H](C)C2)c1C#N] | 4-[(3R)-4-(cyclopropylcarbonyl)-3-methylpiperazin-1-yl]-6-ethyl-2-(1-methyl-1H-pyrazol-4-yl)pyrimidine-5-carbonitrile | Calc'd 380, found |
| 6-7 | 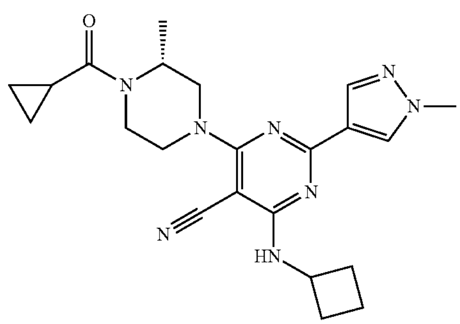 [SMILES: C[C@@H]1CN(c2nc(-c3cnn(C)c3)nc(NC3CCC3)c2C#N)CCN1C(=O)C1CC1] | 4-(cyclobutylamino)-6-[(3R)-4-(cyclopropylcarbonyl)-3-methylpiperazin-1-yl]-2-(1-methyl-1H-pyrazol-4-yl)pyrimidine-5-carbonitrile | Calc'd 421, found |
| 6-8 | 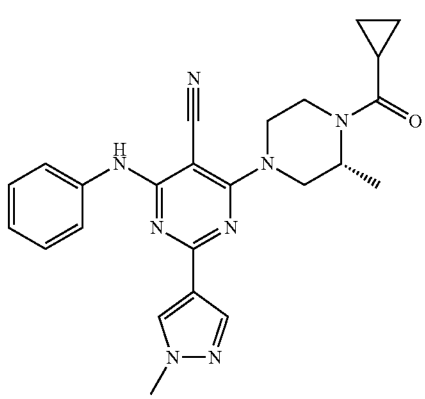 [SMILES: C[C@@H]1CN(c2nc(-c3cnn(C)c3)nc(Nc3ccccc3)c2C#N)CCN1C(=O)C1CC1] | 4-[(3R)-4-(cyclopropylcarbonyl)-3-methylpiperazin-1-yl]-2-(1-methyl-1H-pyrazol-4-yl)-6-(phenylamino)pyrimidine-5-carbonitrile | Calc'd 443, found |

TABLE 6-continued

| Compound | Structure | Name | Exact Mass [M + H]+ |
|---|---|---|---|
| 6-9 | 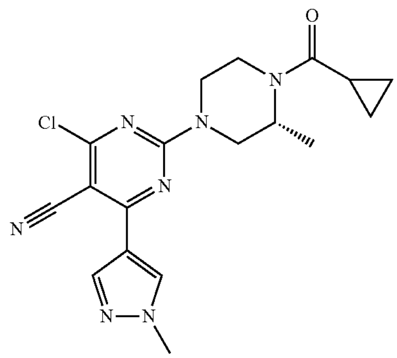 [SMILES: C[C@@H]1CN(c2nc(Cl)c(C#N)c(-c3cnn(C)c3)n2)CCN1C(=O)C1CC1] | 4-chloro-2-[(3R)-4-(cyclopropylcarbonyl)-3-methylpiperazin-1-yl]-6-(1-methyl-1H-pyrazol-4-yl)pyrimidine-5-carbonitrile | Calc'd 386, found |
| 6-10 | 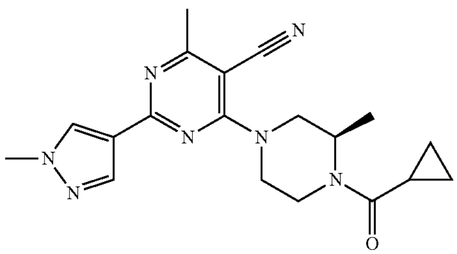 [SMILES: Cc1nc(-c2cnn(C)c2)nc(N2CCN(C(=O)C3CC3)[C@H](C)C2)c1C#N] | 4-[(3R)-4-(cyclopropylcarbonyl)-3-methylpiperazin-1-yl]-6-methyl-2-(1-methyl-1H-pyrazol-4-yl)pyrimidine-5-carbonitrile | Calc'd 366, found |
| 6-11 | 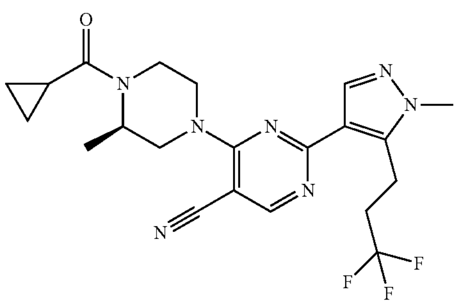 [SMILES: C[C@@H]1CN(c2nc(-c3cnn(C)c3CCC(F)(F)F)ncc2C#N)CCN1C(=O)C1CC1] | 4-[(3R)-4-(cyclopropylcarbonyl)-3-methylpiperazin-1-yl]-2-[1-methyl-5-(3,3,3-trifluoropropyl)-1H-pyrazol-4-yl]pyrimidine-5-carbonitrile | Calc'd 448, found |
| 6-12 | 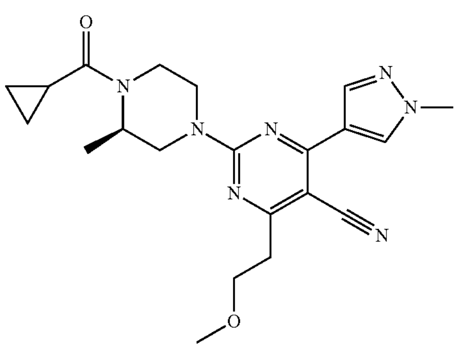 [SMILES: COCCc1nc(N2CCN(C(=O)C3CC3)[C@H](C)C2)nc(-c2cnn(C)c2)c1C#N] | 2-[(3R)-4-(cyclopropylcarbonyl)-3-methylpiperazin-1-yl]-4-(2-methoxyethyl)-6-(1-methyl-1H-pyrazol-4-yl)pyrimidine-5-carbonitrile | Calc'd 410, found |
| 6-13 | 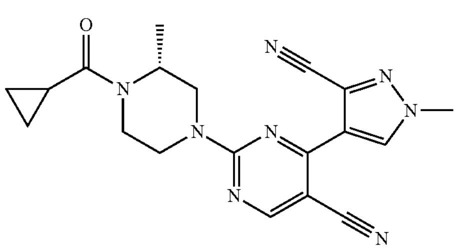 [SMILES: C[C@@H]1CN(c2ncc(C#N)c(-c3cn(C)nc3C#N)n2)CCN1C(=O)C1CC1] | 4-(3-cyano-1-methyl-1H-pyrazol-4-yl)-2-[(3R)-4-(cyclopropylcarbonyl)-3-methylpiperazin-1-yl]pyrimidine-5-carbonitrile | Calc'd 377, found |

TABLE 6-continued

| Compound | Structure | Name | Exact Mass [M + H]+ |
|---|---|---|---|
| 6-14 | 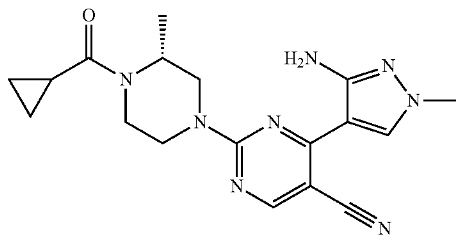 [SMILES: C[C@@H]1CN(c2ncc(C#N)c(-c3cn(C)nc3N)n2)CCN1C(=O)C1CC1] | 4-(3-amino-1-methyl-1H-pyrazol-4-yl)-2-[(3R)-4-(cyclopropylcarbonyl)-3-methylpiperazin-1-yl]pyrimidine-5-carbonitrile | Calc'd 367, found |
| 6-15 | 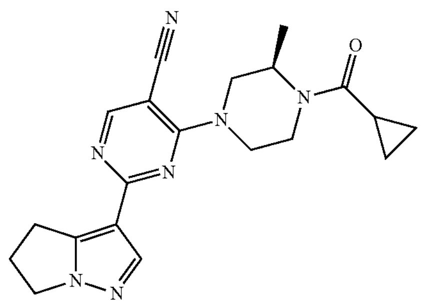 [SMILES: C[C@@H]1CN(c2nc(-c3cnn4c3CCC4)ncc2C#N)CCN1C(=O)C1CC1] | 4-[(3R)-4-(cyclopropylcarbonyl)-3-methylpiperazin-1-yl]-2-(5,6-dihydro-4H-pyrrolo[1,2-b]pyrazol-3-yl)pyrimidine-5-carbonitrile | Calc'd 378, found |
| 6-16 | 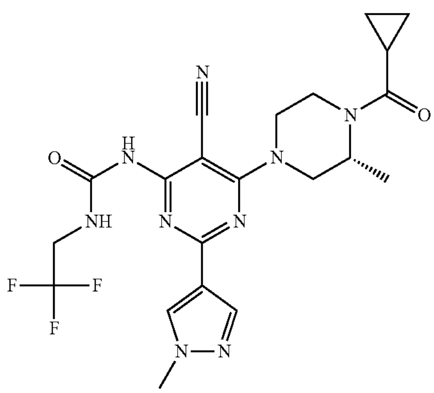 [SMILES: C[C@@H]1CN(c2nc(-c3cnn(C)c3)nc(NC(=O)NCC(F)(F)F)c2C#N)CCN1C(=O)C1CC1] | 1-{5-cyano-6-[(3R)-4-(cyclopropylcarbonyl)-3-methylpiperazin-1-yl]-2-(1-methyl-1H-pyrazol-4-yl)pyrimidin-4-yl}-3-(2,2,2-trifluoroethyl)urea | Calc'd 492, found |
| 6-17 | 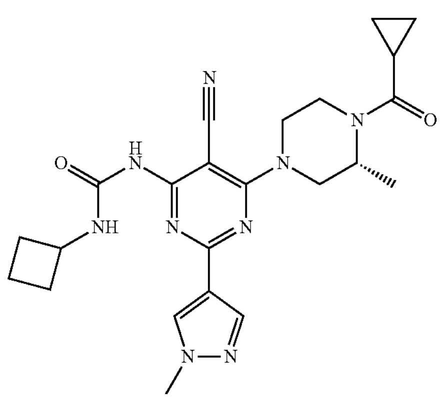 [SMILES: C[C@@H]1CN(c2nc(-c3cnn(C)c3)nc(NC(=O)NC3CCC3)c2C#N)CCN1C(=O)C1CC1] | 1-{5-cyano-6-[(3R)-4-(cyclopropylcarbonyl)-3-methylpiperazin-1-yl]-2-(1-methyl-1H-pyrazol-4-yl)pyrimidin-4-yl}-3-cyclobutylurea | Calc'd 464, found |

TABLE 6-continued

| Compound | Structure | Name | Exact Mass [M + H]+ |
|---|---|---|---|
| 6-18 | 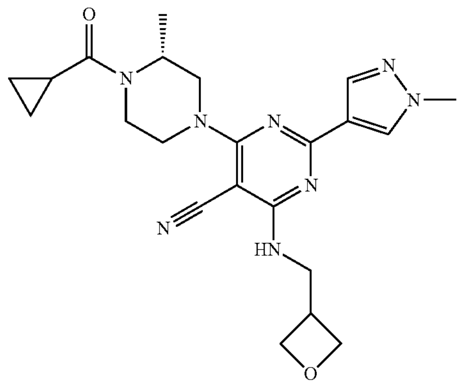 [SMILES: C[C@@H]1CN(c2nc(-c3cnn(C)c3)nc(NCC3COC3)c2C#N)CCN1C(=O)C1CC1] | 4-[(3R)-4-(cyclopropylcarbonyl)-3-methylpiperazin-1-yl]-2-(1-methyl-1H-pyrazol-4-yl)-6-[(oxetan-3-ylmethyl)amino]pyrimidine-5-carbonitrile | Calc'd 437, found |
| 6-19 | 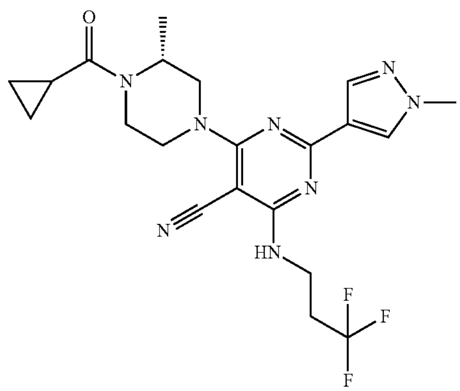 [SMILES: C[C@@H]1CN(c2nc(-c3cnn(C)c3)nc(NCCC(F)(F)F)c2C#N)CCN1C(=O)C1CC1] | 4-[(3R)-4-(cyclopropylcarbonyl)-3-methylpiperazin-1-yl]-2-(1-methyl-1H-pyrazol-4-yl)-6-[(3,3,3-trifluoropropyl)amino]pyrimidine-5-carbonitrile | Calc'd 463, found |
| 6-20 | 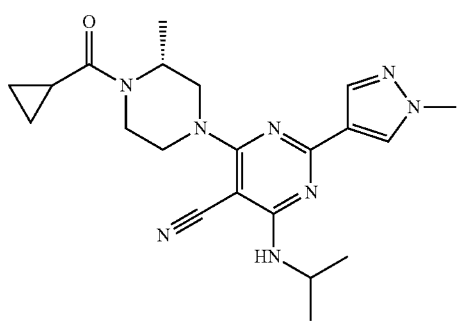 [SMILES: CC(C)Nc1nc(-c2cnn(C)c2)nc(N2CCN(C(=O)C3CC3)[C@H](C)C2)c1C#N] | 4-[(3R)-4-(cyclopropylcarbonyl)-3-methylpiperazin-1-yl]-6-[(1-methylethyl)amino]-2-(1-methyl-1H-pyrazol-4-yl)pyrimidine-5-carbonitrile | Calc'd 409, found |
| 6-21 | 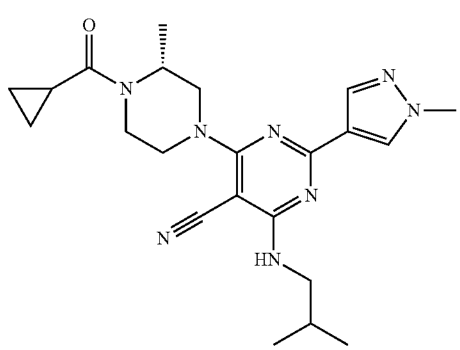 [SMILES: CC(C)CNc1nc(-c2cnn(C)c2)nc(N2CCN(C(=O)C3CC3)[C@H](C)C2)c1C#N] | 4-[(3R)-4-(cyclopropylcarbonyl)-3-methylpiperazin-1-yl]-6-[(2-methylpropyl)amino]-2-(1-methyl-1H-pyrazol-4-yl)pyrimidine-5-carbonitrile | Calc'd 423, found |

TABLE 6-continued

| Compound | Structure | Name | Exact Mass [M + H]+ |
|---|---|---|---|
| 6-22 | 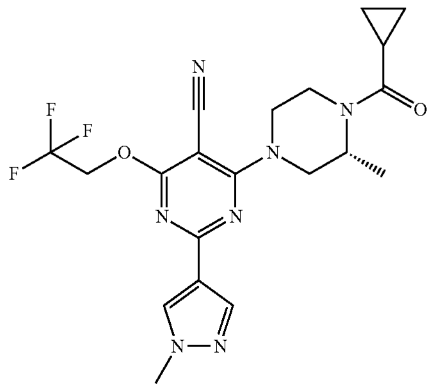 [SMILES: C[C@@H]1CN(c2nc(-c3cnn(C)c3)nc(OCC(F)(F)F)c2C#N)CCN1C(=O)C1CC1] | 4-[(3R)-4-(cyclopropylcarbonyl)-3-methylpiperazin-1-yl]-2-(1-methyl-1H-pyrazol-4-yl)-6-(2,2,2-trifluoroethoxy)pyrimidine-5-carbonitrile | Calc'd 450, found |
| 6-23 | 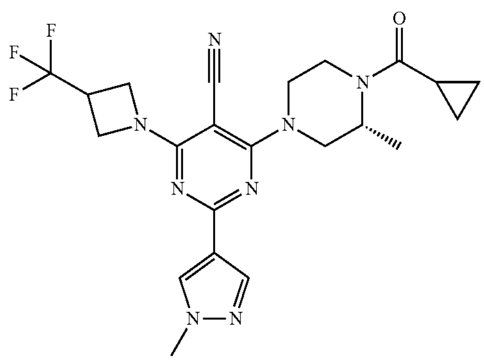 [SMILES: C[C@@H]1CN(c2nc(-c3cnn(C)c3)nc(N3CC(C(F)(F)F)C3)c2C#N)CCN1C(=O)C1CC1] | 4-[(3R)-4-(cyclopropylcarbonyl)-3-methylpiperazin-1-yl]-2-(1-methyl-1H-pyrazol-4-yl)-6-[3-(trifluoromethyl)azetidin-1-yl]pyrimidine-5-carbonitrile | Calc'd 475, found |
| 6-24 | 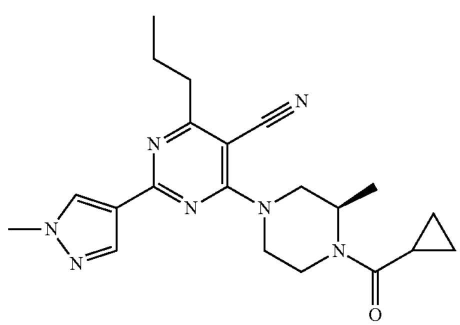 [SMILES: CCCc1nc(-c2cnn(C)c2)nc(N2CCN(C(=O)C3CC3)[C@H](C)C2)c1C#N] | 4-[(3R)-4-(cyclopropylcarbonyl)-3-methylpiperazin-1-yl]-2-(1-methyl-1H-pyrazol-4-yl)-6-propylpyrimidine-5-carbonitrile | Calc'd 394, found |
| 6-25 | 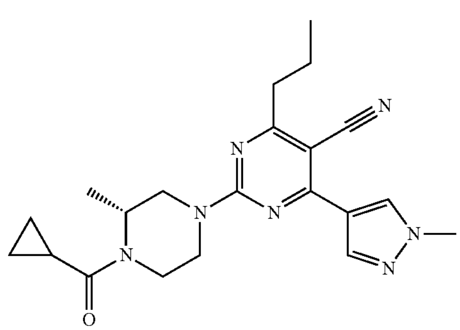 [SMILES: CCCc1nc(N2CCN(C(=O)C3CC3)[C@H](C)C2)nc(-c2cnn(C)c2)c1C#N] | 2-[(3R)-4-(cyclopropylcarbonyl)-3-methylpiperazin-1-yl]-4-(1-methyl-1H-pyrazol-4-yl)-6-propylpyrimidine-5-carbonitrile | Calc'd 394, found |

TABLE 6-continued

| Compound | Structure | Name | Exact Mass [M + H]+ |
|---|---|---|---|
| 6-26 | 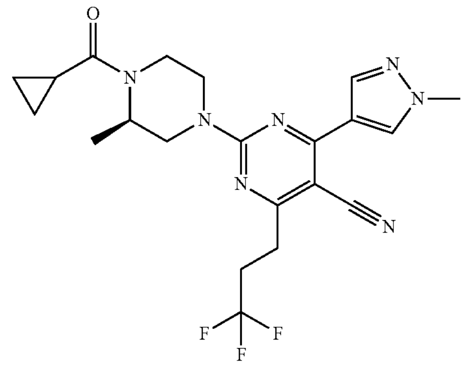 [SMILES: C[C@@H]1CN(c2nc(CCC(F)(F)F)c(C#N)c(-c3cnn(C)c3)n2)CCN1C(=O)C1CC1] | 2-[(3R)-4-(cyclopropylcarbonyl)-3-methylpiperazin-1-yl]-4-(1-methyl-1H-pyrazol-4-yl)-6-(3,3,3-trifluoropropyl)pyrimidine-5-carbonitrile | Calc'd 448, found |
| 6-27 | 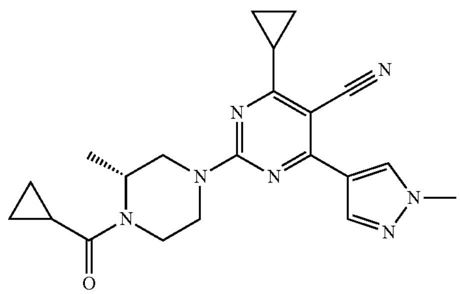 [SMILES: C[C@@H]1CN(c2nc(-c3cnn(C)c3)c(C#N)c(C3CC3)n2)CCN1C(=O)C1CC1] | 4-cyclopropyl-2-[(3R)-4-(cyclopropylcarbonyl)-3-methylpiperazin-1-yl]-6-(1-methyl-1H-pyrazol-4-yl)pyrimidine-5-carbonitrile | Calc'd 392, found |
| 6-28 | 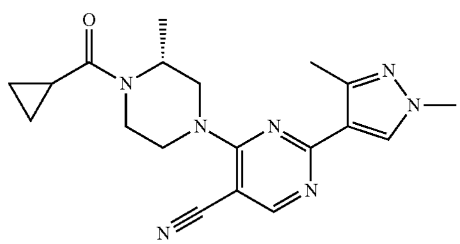 [SMILES: Cc1nn(C)cc1-c1ncc(C#N)c(N2CCN(C(=O)C3CC3)[C@H](C)C2)n1] | 4-[(3R)-4-(cyclopropylcarbonyl)-3-methylpiperazin-1-yl]-2-(1,3-dimethyl-1H-pyrazol-4-yl)pyrimidine-5-carbonitrile | Calc'd 366, found |
| 6-29 | 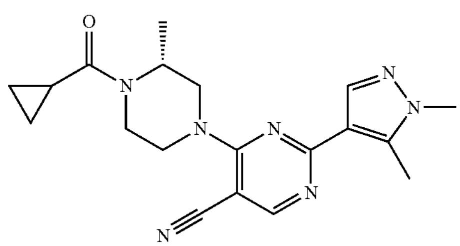 [SMILES: Cc1c(-c2ncc(C#N)c(N3CCN(C(=O)C4CC4)[C@H](C)C3)n2)cnn1C] | 4-[(3R)-4-(cyclopropylcarbonyl)-3-methylpiperazin-1-yl]-2-(1,5-dimethyl-1H-pyrazol-4-yl)pyrimidine-5-carbonitrile | Calc'd 366, found |
| 6-30 | 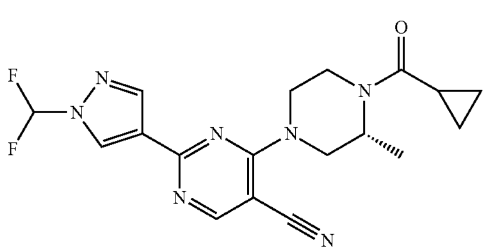 [SMILES: C[C@@H]1CN(c2nc(-c3cnn(C(F)F)c3)ncc2C#N)CCN1C(=O)C1CC1] | 4-[(3R)-4-(cyclopropylcarbonyl)-3-methylpiperazin-1-yl]-2-[1-(difluoromethyl)-1H-pyrazol-4-yl]pyrimidine-5-carbonitrile | Calc'd 388, found |

HTRF PI3K Biochemical Assay to Measure Intrinsic Potency of Compound Inhibitors

The PI3-Kinase biochemical assays were developed to measure the intrinsic potency and compound dependent inhibition of the alpha, beta, delta, and gamma PI3K isoform enzymes. This assay was developed and further optimized from a kit produced by Upstate (Millipore catalog #33-047) (Millipore Sigma, Billerica Mass., USA) and has been configured for high throughput screening (HTS) and structure-activity relationship (SAR) screening. Briefly, this procedure exploits the exquisite specificity and high affinity binding of enzyme reaction substrate phosphatidyl(3,4,5)

triphosphate (PIP3) to the GRP1 pleckstrin homology (PH) domain to generate the signal. In the absence of PIP3, an HTRF (Homogeneous Time-Resolved Fluorescence energy transfer) complex is formed consisting of europium (u)-labeled anti-GST, GST tagged GRP1-PH domain, biotin-PIP3 (biotinylated-PIP3) and streptavidin conjugated APC (Allophycocyanin). The native PIP3 produced by PI3-Kinase activity disrupts in a competitive manner the biotin-PIP3 from the pleckstrin homology (PH) domain, resulting in the loss of energy transfer (HTRF complex) and a decrease in the signal. The format of this assay is the same for all 4 isoforms of PI3K; the differences lie in the concentration of enzyme used to achieve robust assay window. The alpha, beta, and delta assays are run at 0.5, 1, and 0.3 nM enzymes and the gamma assay is run at 5 nM enzyme. The ATP concentration is 100 uM in the alpha, beta, and delta assays and 50 uM adenosine triphosphate (ATP) in the gamma assay. All reactions are run at 5 uM PIP2.

Assay Protocol

Compounds are serially diluted (3-fold in 100% DMSO) across a 384-well polypropylene source plated from column 3 to column 12 and column 13 to column 22, to yield 10 concentration dose response for each test compound. Columns 1, 2, 23 and 24 contain either only DMSO or pharmacological known control inhibitor. Once titrations are made, 2.5 nL of the compounds on 384 well plates are reformatted and transferred by acoustic dispense in quadruplicates to a 1536 assay plate (Greiner) to assay across all four PI3K isoform enzymes.

The PI3-Kinase biochemical assay was optimized using the HTRF kit provided by Upstate (Millipore). The assay kit contains six reagents: 1) 4× Reaction Buffer; 2) native PIP2 (substrate); 3) Stop (EDTA); 4) Detection Mix A (Streptavidin-APC); 5) Detection Mix B (Eu-labeled Anti-GST plus GST-tagged PH-domain); 6) Detection Mix C. In addition, the following items were obtained or purchased; PI3Kinase (catalog #'s alpha 14-602, beta 14-603, gamma 14-558 and delta 14-604 from Upstate Biotechnology now EMD Millipore, Mahopac, N.Y., USA), dithiothreitol (Sigma-Aldrich Corp. (St. Louis, Mo., USA) Catalog #D-5545), Adenosine-5' triphosphate (InVitrogen (Waltham, Mass., USA), Cat#AS001A), native PIP3 (PI(3,4,5)P3, diC8, H$^+$, CELL-SIGNALS, INC., (Columbus, Ohio, USA) Cat #907) DMSO ((Sigma-Aldrich Corp. (St. Louis, Mo., USA) Catalog #472301).

PI3Kinase Reaction Buffer is prepared by dilution the stock 1:4 with de-ionized water. DTT (DL-Dithiothreitol), phosphatidylinositol 4,5-bisphosphate (PIP2) and Biotin-PIP3 were added to 1536 assay plate at a final concentration of 5 mM, 5 mM and 25 nM on the day of use. Enzyme addition and compound pre-incubation are initiated by the addition of 1.25 ul of PI3K (at twice its final concentration) in the 1× reaction buffer to all wells using a BioRaptr™ (Beckman Coulter, Waltham, Mass. USA). Plates are incubated at room temperature for 15 minutes. Reactions are initiated by addition of 1.25 ul of 2× substrate solution (PIP2 and ATP in 1× reaction buffer) using BioRaptr™. Plates are incubated in humidified chamber at room temperature for one hour. Reactions are quenched by addition of 0.625 uL of stop solution to all wells using the BioRaptr™. The quenched reactions are then processed to detect product formation by adding 0.625 uL of Detection Solution to all wells using the BioRaptr™ (Detection mix C, Detection Mix A, and Detection Mix B combined together in an 18:1:1 ratio prepared 2 hours prior to use). Following a one hour incubation in the dark, the HTRF signal is measured on the Envision plate reader set for 330 nm excitation and dual emission detection at 620 nM (Eu) and 665 nM (APC).

Data Analysis

The loss of the HTRF signal is due to the displacement of biotinylated-PIP3 from the PH domain by the PI3K-dependent conversion of PIP2 to PIP3. This loss of signal is nonlinear with respect to both increasing product and time. This non-linear detection will impact accuracy of $IC_{50}$ calculations; therefore, there is a need for a correction factor to obtain more accurate $IC_{50}$ values. This correction is derived from a PIP3 standard curve run in a separate assay plate. All data were calculated using the ratio of acceptor (APC) to donor (Europium) fluorescence in each well of the assay plate. The percent inhibition for each compound concentration was calculated as follows: % inhibition=100× (fluorescence ratio−CtrlB)/(CtrlA−CtrlB) where CtrlA=PI3Kinase reaction+known reference inhibitor and CtrlB=PI3K+DMSO. An $IC_{50}$ was then calculated fitting the % inhibition data to the equation: % (percent) inhibition=min+(Max−min)/1+([inhibitor]/IC50)^n) where min is the % inhibition with inhibitor, max is the signal in DMSO control, and n is the Hill slope.

Biological Data

The following table tabulates the biological data disclosed for the instant invention. The biological data was collected using the methodology described above. For each compound, PI3Kdelta $IC_{50}$ values are listed along with the relative selectivity versus PI3Kalpha, as well as the physical form of the compound dosed in this assay.

The determination of relative selectivity for a given compound is defined as the relative ratio of the (PI3K-alpha$IC_{50}$ value/PI3K-delta $IC_{50}$ value).

| Compound Number | Form Screened | PI3Kdelta IC50 (nM) | Selectivity versus PI3Kalpha |
|---|---|---|---|
| 1-1 | TFA salt | 69 | >10 |
| 1-2 | TFA salt | 51 | >10 |
| 1-3 | TFA salt | 86 | >10 |
| 1-4 | TFA salt | 540 | >10 |
| 1-5 | TFA salt | 220 | >10 |
| 1-6 | TFA salt | 110 | >10 |
| 1-7 | Neutral | 42 | >10 |
| 1-8 | TFA salt | 79 | >10 |
| 1-9 | TFA salt | 90 | >10 |
| 1-10 | TFA salt | 38 | >10 |
| 1-11 | TFA salt | 130 | >10 |
| 1-12 | TFA salt | 410 | >10 |
| 1-13 | TFA salt | 97 | >10 |
| 1-14 | TFA salt | 71 | >10 |
| 1-15 | TFA salt | 27 | >10 |
| 1-16 | Neutral | 31 | >10 |
| 1-17 | TFA salt | 56 | >10 |
| 1-18 | TFA salt | 920 | 8 |
| 1-19 | TFA salt | 290 | >10 |
| 1-20 | TFA salt | 200 | 9 |
| 1-21 | TFA salt | 110 | >10 |
| 1-22 | TFA salt | 950 | 10 |
| 1-23 | TFA salt | 400 | >10 |
| 2-1 | TFA salt | 160 | >10 |
| 2-2 | TFA salt | 1200 | >10 |
| 2-3 | TFA salt | 1400 | 8 |
| 2-4 | TFA salt | 2200 | 5 |
| 2-5 | TFA salt | 190 | >10 |
| 2-6 | TFA salt | 160 | >10 |
| 2-7 | TFA salt | 320 | >10 |
| 2-8 | TFA salt | 270 | >10 |
| 2-9 | TFA salt | 330 | >10 |
| 2-10 | TFA salt | 500 | >10 |
| 2-11 | TFA salt | 1100 | >10 |
| 2-12 | TFA salt | 480 | 10 |
| 2-13 | TFA salt | 470 | >10 |

-continued

| Compound Number | Form Screened | PI3Kdelta IC50 (nM) | Selectivity versus PI3Kalpha |
|---|---|---|---|
| 2-14 | TFA salt | 620 | >10 |
| 2-15 | TFA salt | 650 | >10 |
| 2-16 | TFA salt | 970 | >10 |
| 3-1 | Neutral | 1500 | 8 |
| 3-2 | Neutral | 1600 | 7 |
| 3-3 | TFA salt | 170 | >10 |
| 3-4 | Neutral | 1000 | >10 |
| 4-1 | TFA salt | 110 | >10 |
| 4-2 | Neutral | 260 | >10 |
| 4-3 | Neutral | 370 | >10 |
| 4-4 | Neutral | 1100 | >10 |
| 4-5 | Neutral | 550 | >10 |
| 4-6 | Neutral | 870 | >10 |
| 4-7 | Neutral | 87 | >10 |
| 4-8 | Neutral | 32 | >10 |
| 4-9 | Neutral | 80 | >10 |
| 4-10 | Neutral | 170 | >10 |
| 4-11 | Neutral | 78 | >10 |
| 4-12 | Neutral | 86 | >10 |
| 4-13 | Neutral | 30 | >10 |
| 5-1 | Neutral | 19 | >10 |
| 5-2 | Neutral | 240 | >10 |
| 5-3 | Neutral | 240 | >10 |
| 5-4 | TFA salt | 21 | >10 |
| 5-5 | Neutral | 410 | >10 |
| 5-6 | TFA salt | 190 | >10 |
| 5-7 | TFA salt | 760 | >10 |
| 5-8 | Neutral | 12 | >10 |
| 5-9 | Neutral | 50 | >10 |
| 5-10 | Neutral | 340 | >10 |
| 5-11 | Neutral | 370 | >10 |
| 5-12 | Neutral | 180 | >10 |
| 5-13 | Neutral | 620 | >10 |
| 6-1 | Neutral | 130 | >10 |
| 6-2 | Neutral | 5.6 | >10 |
| 6-3 | Neutral | 480 | >10 |
| 6-4 | Neutral | 8.3 | >10 |
| 6-5 | Neutral | 140 | >10 |
| 6-6 | Neutral | 220 | >10 |
| 6-7 | Neutral | 80 | >10 |
| 6-8 | Neutral | 19 | >10 |
| 6-9 | Neutral | 30 | >10 |
| 6-10 | Neutral | 180 | >10 |
| 6-11 | TFA salt | 160 | >10 |
| 6-12 | TFA salt | 58 | >10 |
| 6-13 | Neutral | 180 | >10 |
| 6-14 | Neutral | 21 | >10 |
| 6-15 | Neutral | 83 | >10 |
| 6-16 | Neutral | 16 | >10 |
| 6-17 | Neutral | 5.0 | >10 |
| 6-18 | Neutral | 49 | >10 |
| 6-19 | Neutral | 9.4 | >10 |
| 6-20 | Neutral | 150 | >10 |
| 6-21 | Neutral | 21 | >10 |
| 6-22 | Neutral | 9.7 | >10 |
| 6-23 | Neutral | 83 | >10 |
| 6-24 | TFA salt | 200 | >10 |
| 6-25 | TFA salt | 10 | >10 |
| 6-26 | TFA salt | 12 | >10 |
| 6-27 | TFA salt | 32 | >10 |
| 6-28 | Neutral | 140 | >10 |
| 6-29 | Neutral | 81 | >10 |
| 6-30 | TFA salt | 330 | >10 |

What is claimed is:

1. A compound or a pharmaceutically acceptable salt, wherein the compound is

4-[(1S,4R)-5-(3-cyanophenyl)-2,5-diazabicyclo[2.2.1]hept-2-yl]-2-(1-methyl-1H-pyrazol-4-yl)pyrimidine-5-carbonitrile;

4-[(1R,4S)-5-(3-fluorophenyl)-2,5-diazabicyclo[2.2.1]hept-2-yl]-2-pyrazolo[1,5-a]pyridin-3-ylpyrimidine-5-carbonitrile;

2-(4,6-dihydropyrrolo[3,4-c]pyrazol-5(1H)-yl)-4-[(1S,4R)-5-(3-fluorophenyl)-2,5-diazabicyclo[2.2.1]hept-2-yl]pyrimidine-5-carbonitrile;

4-{(1S,4R)-5-[6-(difluoromethyl)pyridin-3-yl]-2,5-diazabicyclo[2.2.1]hept-2-yl}-2-(1-methyl-1H-pyrazol-4-yl)pyrimidine-5-carbonitrile;

4-{(1S,4R)-5-[3-(1-hydroxy-1-methylethyl)phenyl]-2,5-diazabicyclo[2.2.1]hept-2-yl}-2-(1-methyl-1H-pyrazol-4-yl)pyrimidine-5-carbonitrile;

2-(1-methyl-1H-pyrazol-4-yl)-4-[(1S,4R)-5-pyridin-3-yl-2,5-diazabicyclo[2.2.1]hept-2-yl]pyrimidine-5-carbonitrile;

4-[(1S,4S)-5-(3-fluorophenyl)-2,5-diazabicyclo[2.2.1]hept-2-yl]-2-(1H-pyrazol-4-yl)pyrimidine-5-carbonitrile;

4-{(1S,4R)-5-[3-(2-fluoroethoxy)phenyl]-2,5-diazabicyclo[2.2.1]hept-2-yl}-2-(1-methyl-1H-pyrazol-4-yl)pyrimidine-5-carbonitrile;

2-(1-methyl-1H-pyrazol-4-yl)-4-{(1S,4R)-5-[3-(1H-pyrrol-1-yl)phenyl]-2,5-diazabicyclo[2.2.1]hept-2-yl}pyrimidine-5-carbonitrile;

2-(1-methyl-1H-pyrazol-4-yl)-4-[(1S,4R)-5-(3-nitrophenyl)-2,5-diazabicyclo[2.2.1]hept-2-yl]pyrimidine-5-carbonitrile;

4-[(1S,4R)-5-(3-cyclopropylphenyl)-2,5-diazabicyclo[2.2.1]hept-2-yl]-2-(1-methyl-1H-pyrazol-4-yl)pyrimidine-5-carbonitrile;

4-{(1S,4R)-5-[3-(1-methylcyclopropyl)phenyl]-2,5-diazabicyclo[2.2.1]hept-2-yl}-2-(1-methyl-1H-pyrazol-4-yl)pyrimidine-5-carbonitrile;

3-{(1R,4S)-5-[5-cyano-2-(1-methyl-1H-pyrazol-4-yl)pyrimidin-4-yl]-2,5-diazabicyclo[2.2.1]hept-2-yl}-N-methylbenzamide;

4-[(1S,4R)-5-(3-methoxyphenyl)-2,5-diazabicyclo[2.2.1]hept-2-yl]-2-(1-methyl-1H-pyrazol-4-yl)pyrimidine-5-carbonitrile;

2-(1-methyl-1H-pyrazol-4-yl)-4-{(1S,4R)-5-[3-(methylsulfonyl)phenyl]-2,5-diazabicyclo[2.2.1]hept-2-yl}pyrimidine-5-carbonitrile;

4-[(1S,4S)-5-(3-fluorophenyl)-2,5-diazabicyclo[2.2.1]hept-2-yl]-2-(1-methyl-H-pyrazol-4-yl)pyrimidine-5-carbonitrile;

4-[(1R,4S)-5-(3-fluorophenyl)-2,5-diazabicyclo[2.2.1]hept-2-yl]-2-(1H-pyrrolo[2,3-b]pyridin-4-yl)pyrimidine-5-carbonitrile;

4-[(1R,4S)-5-(3-fluorophenyl)-2,5-diazabicyclo[2.2.1]hept-2-yl]-2-(1H-pyrrolo[2,3-b]pyridin-5-yl)pyrimidine-5-carbonitrile;

4-[(1R,4S)-5-(3-fluorophenyl)-2,5-diazabicyclo[2.2.1]hept-2-yl]-2-(5-methylpyridin-3-yl)pyrimidine-5-carbonitrile;

4-[(1R,4S)-5-(3-fluorophenyl)-2,5-diazabicyclo[2.2.1]hept-2-yl]-2-(1H-indazol-4-yl)pyrimidine-5-carbonitrile;

4-[(1R,4S)-5-(3-fluorophenyl)-2,5-diazabicyclo[2.2.1]hept-2-yl]-2-isoquinolin-5-ylpyrimidine-5-carbonitrile;

4-[(1S,4R)-5-(3-fluorophenyl)-2,5-diazabicyclo[2.2.1]hept-2-yl]-2-(1,4,6,7-tetrahydro-5H-pyrazolo[4,3-c]pyridin-5-yl)pyrimidine-5-carbonitrile;

4-[(1S,4R)-5-(3-fluorophenyl)-2,5-diazabicyclo[2.2.1]hept-2-yl]-2-morpholin-4-ylpyrimidine-5-carbonitrile;

4-[(1S,4R)-5-(cyclopropylcarbonyl)-2,5-diazabicyclo[2.2.1]hept-2-yl]-2-(1-methyl-1H-pyrazol-4-yl)pyrimidine-5-carbonitrile;

4-[(1S,4R)-5-(cyclopropylsulfonyl)-2,5-diazabicyclo[2.2.1]hept-2-yl]-2-(1-methyl-1H-pyrazol-4-yl)pyrimidine-5-carbonitrile;

4-[(1S,4R)-5-(cyclopropylmethyl)-2,5-diazabicyclo[2.2.1]hept-2-yl]-2-(1-methyl-1H-pyrazol-4-yl)pyrimidine-5-carbonitrile;

(1R,4S)-5-[5-cyano-2-(1-methyl-1H-pyrazol-4-yl)pyrimidin-4-yl]-N-ethyl-2,5-diazabicyclo[2.2.1]heptane-2-carboxamide;

4-[(1S,4R)-5-(2,2-dimethylpropanoyl)-2,5-diazabicyclo[2.2.1]hept-2-yl]-2-(1-methyl-H-pyrazol-4-yl)pyrimidine-5-carbonitrile;

4-[(1S,4R)-5-(3-fluoro-2,2-dimethylpropanoyl)-2,5-diazabicyclo[2.2.1]hept-2-yl]-2-(1-methyl-1H-pyrazol-4-yl)pyrimidine-5-carbonitrile;

4-{(1S,4R)-5-[(3-methyloxetan-3-yl)carbonyl]-2,5-diazabicyclo[2.2.1]hept-2-yl}-2-(1-methyl-1H-pyrazol-4-yl)pyrimidine-5-carbonitrile;

4-[(1S,4R)-5-{[1-(methoxymethyl)cyclopropyl]carbonyl}-2,5-diazabicyclo[2.2.1]hept-2-yl]-2-(1-methyl-1H-pyrazol-4-yl)pyrimidine-5-carbonitrile;

4-[(1S,4R)-5-(cyclobutylcarbonyl)-2,5-diazabicyclo[2.2.1]hept-2-yl]-2-(1-methyl-H-pyrazol-4-yl)pyrimidine-5-carbonitrile;

2-(1-methyl-1H-pyrazol-4-yl)-4-[(1S,4R)-5-(thiophen-2-ylcarbonyl)-2,5-diazabicyclo[2.2.1]hept-2-yl]pyrimidine-5-carbonitrile;

2-(1-methyl-1H-pyrazol-4-yl)-4-[(1S,4R)-5-(1,3-oxazol-4-ylcarbonyl)-2,5-diazabicyclo[2.2.1]hept-2-yl]pyrimidine-5-carbonitrile;

2-(1-methyl-1H-pyrazol-4-yl)-4-[(1S,4R)-5-(oxetan-3-ylacetyl)-2,5-diazabicyclo[2.2.1]hept-2-yl]pyrimidine-5-carbonitrile;

4-{(1S,4R)-5-[(1-methylethyl)sulfonyl]-2,5-diazabicyclo[2.2.1]hept-2-yl}-2-(1-methyl-1H-pyrazol-4-yl)pyrimidine-5-carbonitrile;

2-(1-methyl-1H-pyrazol-4-yl)-4-[(1S,4R)-5-(propylsulfonyl)-2,5-diazabicyclo[2.2.1]hept-2-yl]pyrimidine-5-carbonitrile;

4-[(1S,4R)-5-(cyclopentylsulfonyl)-2,5-diazabicyclo[2.2.1]hept-2-yl]-2-(1-methyl-1H-pyrazol-4-yl)pyrimidine-5-carbonitrile;

4-[(1S,4R)-5-(3-fluoropropyl)-2,5-diazabicyclo[2.2.1]hept-2-yl]-2-(1-methyl-H-pyrazol-4-yl)pyrimidine-5-carbonitrile;

4-[4-(3-fluorophenyl)-3,3-dimethylpiperazin-1-yl]-2-(1-methyl-1H-pyrazol-4-yl)pyrimidine-5-carbonitrile;

4-[4-(3-fluorophenyl)piperazin-1-yl]-2-(1-methyl-1H-pyrazol-4-yl)pyrimidine-5-carbonitrile;

4-[(3R)-4-(3-fluorophenyl)-3-methylpiperazin-1-yl]-2-(1-methyl-1H-pyrazol-4-yl)pyrimidine-5-carbonitrile;

4-[8-(3-fluorophenyl)-3,8-diazabicyclo[3.2.1]oct-3-yl]-2-(1-methyl-1H-pyrazol-4-yl)pyrimidine-5-carbonitrile;

4-[(3R)-4-(cyclopropylcarbonyl)-3-methylpiperazin-1-yl]-2-(1-methyl-1H-pyrazol-4-yl)pyrimidine-5-carbonitrile;

4-[(3R)-3-methyl-4-propanoylpiperazin-1-yl]-2-(1-methyl-1H-pyrazol-4-yl)pyrimidine-5-carbonitrile;

4-[(3R)-4-(cyclobutylcarbonyl)-3-methylpiperazin-1-yl]-2-(1-methyl-1H-pyrazol-4-yl)pyrimidine-5-carbonitrile;

4-{(3R)-3-methyl-4-[(1-methylcyclopropyl)carbonyl]piperazin-1-yl}-2-(1-methyl-1H-pyrazol-4-yl)pyrimidine-5-carbonitrile;

4-{(3R)-4-[(2,2-difluorocyclobutyl)carbonyl]-3-methylpiperazin-1-yl}-2-(1-methyl-1H-pyrazol-4-yl)pyrimidine-5-carbonitrile;

4-[(3R)-4-(cyclopentylcarbonyl)-3-methylpiperazin-1-yl]-2-(1-methyl-1H-pyrazol-4-yl)pyrimidine-5-carbonitrile;

2-(1-methyl-1H-pyrazol-4-yl)-4-[(3R)-3-methyl-4-(spiro[2.4]hept-1-ylcarbonyl)piperazin-1-yl]pyrimidine-5-carbonitrile;

4-[(3R)-3-methyl-4-{[(1R,2R)-2-methylcyclopropyl]carbonyl}piperazin-1-yl]-2-(1-methyl-1H-pyrazol-4-yl)pyrimidine-5-carbonitrile;

4-[(3R)-3-methyl-4-{[(1S,2R)-2-methylcyclopropyl]carbonyl}piperazin-1-yl]-2-(1-methyl-1H-pyrazol-4-yl)pyrimidine-5-carbonitrile;

4-[(3R)-4-(3-fluorophenyl)-3-methylpiperazin-1-yl]-2-(1-methyl-1H-pyrazol-4-yl)pyrimidine-5-carbonitrile;

4-[(3R)-3-methyl-4-(3-nitrophenyl)piperazin-1-yl]-2-(1-methyl-1H-pyrazol-4-yl)pyrimidine-5-carbonitrile;

4-[(3R)-4-(3-cyanophenyl)-3-methylpiperazin-1-yl]-2-(1-methyl-1H-pyrazol-4-yl)pyrimidine-5-carbonitrile;

4-{(3R)-3-methyl-4-[3-(methylsulfonyl)phenyl]piperazin-1-yl}-2-(1-methyl-1H-pyrazol-4-yl)pyrimidine-5-carbonitrile;

3-{2-[(3R)-4-(cyclopropylcarbonyl)-3-methylpiperazin-1-yl]-4-(1-methyl-1H-pyrazol-4-yl)pyrimidin-5-yl}prop-2-yn-1-ol;

2-[(3R)-4-(cyclopropylcarbonyl)-3-methylpiperazin-1-yl]-6-(1-methyl-1H-pyrazol-4-yl)pyrimidine-4-carbonitrile;

6-[(3R)-4-(cyclopropylcarbonyl)-3-methylpiperazin-1-yl]-2-(1-methyl-1H-pyrazol-4-yl)pyrimidine-4-carbonitrile;

2-[(3R)-4-(cyclopropylcarbonyl)-3-methylpiperazin-1-yl]-4-(1-methyl-1H-pyrazol-4-yl)pyrimidine-5-carbonitrile;

2-[(3R)-4-(cyclopropylcarbonyl)-3-methylpiperazin-1-yl]-5-[5-(1-methylethyl)-1,3-oxazol-2-yl]-4-(1-methyl-1H-pyrazol-4-yl)pyrimidine;

4-[(3R)-4-(cyclopropylcarbonyl)-3-(2-methylpropyl)piperazin-1-yl]-2-(1-methyl-H-pyrazol-4-yl)pyrimidine-5-carbonitrile;

4-[(3S)-4-(cyclopropylcarbonyl)-3-(hydroxymethyl)piperazin-1-yl]-2-(1-methyl-1H-pyrazol-4-yl)pyrimidine-5-carbonitrile;

2-[(3R)-4-(cyclopropylcarbonyl)-3-methylpiperazin-1-yl]-5-(3-methylbut-1-yn-1-yl)-4-(1-methyl-1H-pyrazol-4-yl)pyrimidine;

2-[(3R)-4-(cyclopropylcarbonyl)-3-methylpiperazin-1-yl]-5-ethynyl-4-(1-methyl-1H-pyrazol-4-yl)pyrimidine;

2-[(3R)-4-(cyclopropylcarbonyl)-3-methylpiperazin-1-yl]-4-(1-methyl-1H-pyrazol-4-yl)-5-(methylsulfanyl)pyrimidine;

2-[(3R)-4-(cyclopropylcarbonyl)-3-methylpiperazin-1-yl]-5-(difluoromethyl)-4-(1-methyl-1H-pyrazol-4-yl)pyrimidine;

ethyl 2-[(3R)-4-(cyclopropylcarbonyl)-3-methylpiperazin-1-yl]-4-(1-methyl-1H-pyrazol-4-yl)pyrimidine-5-carboxylate;

5-chloro-4-[(3R)-4-(cyclopropylcarbonyl)-3-methylpiperazin-1-yl]-2-(1-methyl-1H-pyrazol-4-yl)pyrimidine;

4-amino-6-[(3R)-4-(cyclopropylcarbonyl)-3-methylpiperazin-1-yl]-2-(1-methyl-1H-pyrazol-4-yl)pyrimidine-5-carbonitrile;

1-{5-cyano-6-[(3R)-4-(cyclopropylcarbonyl)-3-methylpiperazin-1-yl]-2-(1-methyl-1H-pyrazol-4-yl)pyrimidin-4-yl}-3-(1-methylethyl)urea;

N-{5-cyano-6-[(3R)-4-(cyclopropylcarbonyl)-3-methylpiperazin-1-yl]-2-(1-methyl-1H-pyrazol-4-yl)pyrimidin-4-yl}acetamide;

4-[(3R)-4-(cyclopropylcarbonyl)-3-methylpiperazin-1-yl]-2-(1-methyl-1H-pyrazol-4-yl)-6-[(2,2,2-trifluoroethyl)amino]pyrimidine-5-carbonitrile;

4-chloro-6-[(3R)-4-(cyclopropylcarbonyl)-3-methylpiperazin-1-yl]-2-(1-methyl-1H-pyrazol-4-yl)pyrimidine-5-carbonitrile;

4-[(3R)-4-(cyclopropylcarbonyl)-3-methylpiperazin-1-yl]-6-ethyl-2-(1-methyl-1H-pyrazol-4-yl)pyrimidine-5-carbonitrile;

4-(cyclobutylamino)-6-[(3R)-4-(cyclopropylcarbonyl)-3-methylpiperazin-1-yl]-2-(1-methyl-1H-pyrazol-4-yl)pyrimidine-5-carbonitrile;

4-[(3R)-4-(cyclopropylcarbonyl)-3-methylpiperazin-1-yl]-2-(1-methyl-1H-pyrazol-4-yl)-6-(phenylamino)pyrimidine-5-carbonitrile;

4-chloro-2-[(3R)-4-(cyclopropylcarbonyl)-3-methylpiperazin-1-yl]-6-(1-methyl-1H-pyrazol-4-yl)pyrimidine-5-carbonitrile;

4-[(3R)-4-(cyclopropylcarbonyl)-3-methylpiperazin-1-yl]-6-methyl-2-(1-methyl-1H-pyrazol-4-yl)pyrimidine-5-carbonitrile;

4-[(3R)-4-(cyclopropylcarbonyl)-3-methylpiperazin-1-yl]-2-[1-methyl-5-(3,3,3-trifluoropropyl)-1H-pyrazol-4-yl]pyrimidine-5-carbonitrile;

2-[(3R)-4-(cyclopropylcarbonyl)-3-methylpiperazin-1-yl]-4-(2-methoxyethyl)-6-(1-methyl-1H-pyrazol-4-yl)pyrimidine-5-carbonitrile;

4-(3-cyano-1-methyl-1H-pyrazol-4-yl)-2-[(3R)-4-(cyclopropylcarbonyl)-3-methylpiperazin-1-yl]pyrimidine-5-carbonitrile;

4-(3-amino-1-methyl-1H-pyrazol-4-yl)-2-[(3R)-4-(cyclopropylcarbonyl)-3-methylpiperazin-1-yl]pyrimidine-5-carbonitrile;

4-[(3R)-4-(cyclopropylcarbonyl)-3-methylpiperazin-1-yl]-2-(5,6-dihydro-4H-pyrrolo[1,2-b]pyrazol-3-yl)pyrimidine-5-carbonitrile;

1-{5-cyano-6-[(3R)-4-(cyclopropylcarbonyl)-3-methylpiperazin-1-yl]-2-(1-methyl-1H-pyrazol-4-yl)pyrimidin-4-yl}-3-(2,2,2-trifluoroethyl)urea;

1-{5-cyano-6-[(3R)-4-(cyclopropylcarbonyl)-3-methylpiperazin-1-yl]-2-(1-methyl-1H-pyrazol-4-yl)pyrimidin-4-yl}-3-cyclobutylurea;

4-[(3R)-4-(cyclopropylcarbonyl)-3-methylpiperazin-1-yl]-2-(1-methyl-1H-pyrazol-4-yl)-6-[(oxetan-3-ylmethyl)amino]pyrimidine-5-carbonitrile;

4-[(3R)-4-(cyclopropylcarbonyl)-3-methylpiperazin-1-yl]-2-(1-methyl-1H-pyrazol-4-yl)-6-[(3,3,3-trifluoropropyl)amino]pyrimidine-5-carbonitrile;

4-[(3R)-4-(cyclopropylcarbonyl)-3-methylpiperazin-1-yl]-6-[(1-methylethyl)amino]-2-(1-methyl-1H-pyrazol-4-yl)pyrimidine-5-carbonitrile;

4-[(3R)-4-(cyclopropylcarbonyl)-3-methylpiperazin-1-yl]-6-[(2-methylpropyl)amino]-2-(1-methyl-1H-pyrazol-4-yl)pyrimidine-5-carbonitrile;

4-[(3R)-4-(cyclopropylcarbonyl)-3-methylpiperazin-1-yl]-2-(1-methyl-1H-pyrazol-4-yl)-6-(2,2,2-trifluoroethoxy)pyrimidine-5-carbonitrile;

4-[(3R)-4-(cyclopropylcarbonyl)-3-methylpiperazin-1-yl]-2-(1-methyl-1H-pyrazol-4-yl)-6-[3-(trifluoromethyl)azetidin-1-yl]pyrimidine-5-carbonitrile;

4-[(3R)-4-(cyclopropylcarbonyl)-3-methylpiperazin-1-yl]-2-(1-methyl-1H-pyrazol-4-yl)-6-propylpyrimidine-5-carbonitrile;

2-[(3R)-4-(cyclopropylcarbonyl)-3-methylpiperazin-1-yl]-4-(1-methyl-1H-pyrazol-4-yl)-6-propylpyrimidine-5-carbonitrile;

2-[(3R)-4-(cyclopropylcarbonyl)-3-methylpiperazin-1-yl]-4-(1-methyl-1H-pyrazol-4-yl)-6-(3,3,3-trifluoropropyl)pyrimidine-5-carbonitrile;

4-cyclopropyl-2-[(3R)-4-(cyclopropylcarbonyl)-3-methylpiperazin-1-yl]-6-(1-methyl-1H-pyrazol-4-yl)pyrimidine-5-carbonitrile;

4-[(3R)-4-(cyclopropylcarbonyl)-3-methylpiperazin-1-yl]-2-(1,3-dimethyl-1H-pyrazol-4-yl)pyrimidine-5-carbonitrile;

4-[(3R)-4-(cyclopropylcarbonyl)-3-methylpiperazin-1-yl]-2-(1,5-dimethyl-1H-pyrazol-4-yl)pyrimidine-5-carbonitrile; or 4-[(3R)-4-(cyclopropylcarbonyl)-3-methylpiperazin-1-yl]-2-[1-(difluoromethyl)-1H-pyrazol-4-yl]pyrimidine-5-carbonitrile.

2. A pharmaceutical composition comprising an effective amount of a compound according to claim 1, or a pharmaceutically acceptable salt thereof, and a pharmaceutically acceptable carrier.

3. The pharmaceutical composition according to claim 2, further comprising one or more other therapeutic agents.

* * * * *